US009176319B2

(12) United States Patent
Bouma et al.

(10) Patent No.: US 9,176,319 B2
(45) Date of Patent: Nov. 3, 2015

(54) METHODS, ARRANGEMENTS AND APPARATUS FOR UTILIZING A WAVELENGTH-SWEPT LASER USING ANGULAR SCANNING AND DISPERSION PROCEDURES

(75) Inventors: Brett Eugene Bouma, Quincy, MA (US); Reza Motaghiannezam, Glendale, CA (US); Guillermo J. Tearney, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 2004 days.

(21) Appl. No.: 12/052,984

(22) Filed: Mar. 21, 2008

(65) Prior Publication Data

US 2008/0232410 A1 Sep. 25, 2008

Related U.S. Application Data

(60) Provisional application No. 60/896,630, filed on Mar. 23, 2007.

(51) Int. Cl.
*G02B 26/12* (2006.01)
*G01J 3/02* (2006.01)
(Continued)

(52) U.S. Cl.
CPC . *G02B 26/12* (2013.01); *G01J 3/02* (2013.01); *G01J 3/021* (2013.01); *G01J 3/0208* (2013.01);
(Continued)

(58) Field of Classification Search
USPC ......... 356/300, 337–343, 450–521, 121, 122; 362/293; 359/578, 489.19, 486.02, 359/196.1–226.3, 308
See application file for complete search history.

(56) References Cited

U.S. PATENT DOCUMENTS

| 2,339,754 A | 1/1944 | Brace |
| 3,090,753 A | 5/1963 | Matuszak et al. |

(Continued)

FOREIGN PATENT DOCUMENTS

| CN | 1550203 | 12/2004 |
| DE | 4105221 | 9/1991 |

(Continued)

OTHER PUBLICATIONS

International Search Report and Written Opinion dated Feb. 2, 2009 for International Application No. PCT/US2008/071786.

(Continued)

*Primary Examiner* — J Doak
(74) *Attorney, Agent, or Firm* — Andrews Kurth LLP

(57) ABSTRACT

Exemplary systems and methods for filtering an electromagnetic radiation can be provided. For example, at least one first arrangement can be provided which is capable of receiving at least one first electro-magnetic radiation and forwarding at least one second electro-magnetic radiation at different angles with respect to a direction of incidence of the first electro-magnetic radiation. At least one second wavelength dispersion arrangement can be provided which is configured to receive the second electro-magnetic radiation, forward at least one third electro-magnetic radiation to the first arrangement and further receive at least one fourth electro-magnetic radiation. The third electro-magnetic radiation can be based on the second electro-magnetic radiation, and the fourth electro-magnetic radiation can be based on the third electro-magnetic radiation. For example, the second arrangement can be configured to forward the second electro-magnetic radiation at different angles with respect to a direction of incidence of the at least one particular electro-magnetic radiation. Exemplary embodiments of methods can be provided to implement such exemplary techniques.

28 Claims, 21 Drawing Sheets

(51) Int. Cl.

| | | |
|---|---|---|
| *G01J 3/06* | (2006.01) | |
| *G01J 3/10* | (2006.01) | |
| *G01J 3/18* | (2006.01) | |
| *G01J 3/433* | (2006.01) | |
| *G02B 26/00* | (2006.01) | |
| *G01J 3/12* | (2006.01) | |
| *G01N 21/39* | (2006.01) | |
| *H01S 5/14* | (2006.01) | |

(52) U.S. Cl.
CPC ............... *G01J 3/0218* (2013.01); *G01J 3/06* (2013.01); *G01J 3/10* (2013.01); *G01J 3/18* (2013.01); *G01J 3/4338* (2013.01); *G02B 26/002* (2013.01); *G01J 2003/1286* (2013.01); *G01N 21/39* (2013.01); *H01S 5/141* (2013.01); *H01S 5/143* (2013.01); *H01S 5/146* (2013.01)

(56) References Cited

U.S. PATENT DOCUMENTS

| | | |
|---|---|---|
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,030,831 A | 6/1977 | Gowrinathan |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,303,300 A | 12/1981 | Pressiat et al. |
| 4,428,643 A | 1/1984 | Kay |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,639,999 A | 2/1987 | Daniele |
| 4,650,327 A | 3/1987 | Ogi |
| 4,734,578 A | 3/1988 | Horikawa |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefèvre et al. |
| 4,940,328 A | 7/1990 | Hartman |
| 4,965,441 A | 10/1990 | Picard |
| 4,965,599 A | 10/1990 | Roddy et al. |
| 4,966,589 A | 10/1990 | Kaufman |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,197,470 A | 3/1993 | Helfer et al. |

| | | |
|---|---|---|
| 5,202,745 A | 4/1993 | Sorin et al. |
| 5,202,931 A | 4/1993 | Bacus et al. |
| 5,208,651 A | 5/1993 | Buican |
| 5,212,667 A | 5/1993 | Tomlinson et al. |
| 5,214,538 A | 5/1993 | Lobb |
| 5,217,456 A | 6/1993 | Narciso, Jr. |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,251,009 A | 10/1993 | Bruno |
| 5,262,644 A | 11/1993 | Maguire |
| 5,275,594 A | 1/1994 | Baker |
| 5,281,811 A | 1/1994 | Lewis |
| 5,283,795 A | 2/1994 | Fink |
| 5,291,885 A | 3/1994 | Taniji et al. |
| 5,293,872 A | 3/1994 | Alfano et al. |
| 5,293,873 A | 3/1994 | Fang |
| 5,302,025 A | 4/1994 | Kleinerman |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,333,144 A | 7/1994 | Liedenbaum et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,404,415 A | 4/1995 | Mori et al. |
| 5,411,016 A | 5/1995 | Kume et al. |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,483,058 A * | 1/1996 | Leviton .................... 250/231.13 |
| 5,486,701 A | 1/1996 | Norton et al. |
| 5,491,524 A | 2/1996 | Hellmuth et al. |
| 5,491,552 A | 2/1996 | Knuttel |
| 5,522,004 A | 5/1996 | Djupsjobacka et al. |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knuttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab |
| 5,635,830 A | 6/1997 | Itoh |
| 5,649,924 A | 7/1997 | Everett et al. |
| 5,697,373 A | 12/1997 | Richards-Kortum et al. |
| 5,698,397 A | 12/1997 | Zarling et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |
| 5,752,518 A | 5/1998 | McGee et al. |
| 5,784,352 A | 7/1998 | Swanson et al. |
| 5,785,651 A | 7/1998 | Baker et al. |
| 5,795,295 A | 8/1998 | Hellmuth et al. |
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,810,719 A | 9/1998 | Toida |

(56) References Cited

U.S. PATENT DOCUMENTS

| | | |
|---|---|---|
| 5,817,144 A | 10/1998 | Gregory et al. |
| 5,836,877 A | 11/1998 | Zavislan et al. |
| 5,840,023 A | 11/1998 | Oraevsky et al. |
| 5,840,031 A | 11/1998 | Crowley |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | Harris et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | Dimarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochmann et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,268 B1 | 8/2001 | Miller et al. |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang et al. |
| 6,564,087 B1 | 5/2003 | Pitris et al. |
| 6,564,089 B2 | 5/2003 | Izatt et al. |
| 6,567,585 B2 | 5/2003 | Harris et al. |
| 6,583,058 B1 | 6/2003 | Rajendran |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,725,073 B1 | 4/2004 | Motamedi et al. |
| 6,738,144 B1 | 5/2004 | Dogariu et al. |
| 6,741,355 B2 | 5/2004 | Drabarek |
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |

(56) References Cited

U.S. PATENT DOCUMENTS

| | | |
|---|---|---|
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,805,034 B2 | 9/2010 | Kato et al. |
| 2001/0020126 A1 | 9/2001 | Swanson et al. |
| 2001/0036002 A1 | 11/2001 | Tearney et al. |
| 2001/0047137 A1 | 11/2001 | Moreno et al. |
| 2002/0016533 A1 | 2/2002 | Marchitto et al. |
| 2002/0024015 A1 | 2/2002 | Hoffmann et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Roche et al. |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0199769 A1 | 10/2003 | Podoleanu et al. |
| 2003/0216719 A1 | 11/2003 | Debenedictis et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0189999 A1 | 9/2004 | De Groot et al. |
| 2004/0212808 A1 | 10/2004 | Okawa et al. |
| 2004/0239938 A1 | 12/2004 | Izatt et al. |
| 2004/0246490 A1 | 12/2004 | Wang |
| 2004/0246583 A1 | 12/2004 | Mueller et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0004453 A1 | 1/2005 | Tearney et al. |
| 2005/0007647 A1* | 1/2005 | Oh et al. ............ 359/290 |
| 2005/0018133 A1 | 1/2005 | Huang et al. |
| 2005/0018201 A1 | 1/2005 | De Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0197530 A1 | 9/2005 | Wallace et al. |
| 2005/0254061 A1 | 11/2005 | Alphonse |
| 2006/0020172 A1 | 1/2006 | Luerssen et al. |

(56) References Cited

U.S. PATENT DOCUMENTS

| | | |
|---|---|---|
| 2006/0033923 A1 | 2/2006 | Hirasawa et al. |
| 2006/0039004 A1 | 2/2006 | de Boer et al. |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0167363 A1 | 7/2006 | Osypka et al. |
| 2006/0171503 A1 | 8/2006 | O'Hara et al. |
| 2006/0193352 A1 | 8/2006 | Chong |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0038040 A1 | 2/2007 | Cense et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0208225 A1 | 9/2007 | Czaniera et al. |
| 2007/0223006 A1 | 9/2007 | Tearney et al. |
| 2007/0233056 A1 | 10/2007 | Yun |
| 2007/0236700 A1 | 10/2007 | Yun et al. |
| 2007/0258094 A1 | 11/2007 | Izatt et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0021275 A1 | 1/2008 | Tearney et al. |
| 2008/0049220 A1 | 2/2008 | Izzia et al. |
| 2008/0094613 A1 | 4/2008 | de Boer et al. |
| 2008/0094637 A1 | 4/2008 | de Boer et al. |
| 2008/0097225 A1 | 4/2008 | Tearney et al. |
| 2008/0097709 A1 | 4/2008 | de Boer et al. |
| 2008/0100837 A1 | 5/2008 | de Boer et al. |
| 2008/0152353 A1 | 6/2008 | de Boer et al. |
| 2008/0154090 A1 | 6/2008 | Hashimshony |
| 2008/0204762 A1 | 8/2008 | Izatt et al. |
| 2008/0228086 A1 | 9/2008 | Ilegbusi |
| 2008/0265130 A1 | 10/2008 | Colomb et al. |
| 2008/0308730 A1 | 12/2008 | Vizi et al. |
| 2009/0005691 A1 | 1/2009 | Huang |
| 2009/0011948 A1 | 1/2009 | Uniu et al. |
| 2009/0051923 A1 | 2/2009 | Zuluaga |
| 2009/0131801 A1 | 5/2009 | Suter et al. |
| 2009/0192358 A1 | 7/2009 | Jaffer et al. |
| 2009/0196477 A1 | 8/2009 | Cense et al. |
| 2009/0273777 A1 | 11/2009 | Yun et al. |
| 2009/0281390 A1 | 11/2009 | Qiu et al. |
| 2009/0290156 A1 | 11/2009 | Popescu et al. |
| 2010/0086251 A1 | 4/2010 | Xu et al. |
| 2010/0094576 A1 | 4/2010 | de Boer et al. |
| 2010/0150467 A1 | 6/2010 | Zhao et al. |

FOREIGN PATENT DOCUMENTS

| | | |
|---|---|---|
| DE | 4309056 | 9/1994 |
| DE | 19542955 | 5/1997 |
| DE | 10351319 | 6/2005 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 0933096 | 8/1999 |
| EP | 1324051 | 7/2003 |
| EP | 14296799 | 6/2004 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | H08-136345 A | 5/1969 |
| JP | 6073405 | 4/1985 |
| JP | 04-056907 | 2/1992 |
| JP | 20040056907 | 2/1992 |
| JP | 4135550 | 5/1992 |
| JP | 4135551 | 5/1992 |
| JP | 5509417 | 11/1993 |
| JP | 9-230248 | 9/1997 |
| JP | 10-267631 | 10/1998 |
| JP | 2000-046729 | 2/2000 |
| JP | 2000-121961 | 4/2000 |
| JP | 2001-004447 A | 1/2001 |
| JP | 2001-174404 | 6/2001 |
| JP | 2001-174744 | 6/2001 |
| JP | 2001-508340 | 6/2001 |
| JP | 2001-212086 | 8/2001 |
| JP | 2001-525580 | 12/2001 |
| JP | 2002-205434 | 2/2002 |
| JP | 2002-095663 | 4/2002 |
| JP | 2002214127 | 7/2002 |
| JP | 2003-014585 | 1/2003 |
| JP | 2003-504627 | 2/2003 |
| JP | 20030035659 | 2/2003 |
| JP | 2003-512085 | 4/2003 |
| JP | 2003-513278 | 4/2003 |
| JP | 2003-516531 | 5/2003 |
| JP | 2005-062850 | 3/2005 |
| JP | 2005-110208 | 4/2005 |
| JP | 2005195485 | 7/2005 |
| JP | 2007271761 | 10/2007 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 9848846 | 11/1998 |
| WO | 9905487 | 2/1999 |
| WO | 9944089 | 2/1999 |
| WO | 9944089 | 9/1999 |
| WO | 99-45338 | 10/1999 |
| WO | 9957507 | 11/1999 |
| WO | 00-42906 | 7/2000 |
| WO | 0058766 | 10/2000 |
| WO | 0101111 | 1/2001 |
| WO | 0108579 | 2/2001 |
| WO | 0127679 | 4/2001 |
| WO | 0138820 | 5/2001 |
| WO | 0142735 | 6/2001 |
| WO | 0236015 | 5/2002 |
| WO | 0237075 | 5/2002 |
| WO | 0238040 | 5/2002 |
| WO | 02053050 | 7/2002 |
| WO | 02054027 | 7/2002 |
| WO | 02-083003 | 10/2002 |
| WO | 02084263 | 10/2002 |
| WO | 03013624 | 2/2003 |
| WO | 03020119 | 3/2003 |
| WO | 03046495 | 6/2003 |
| WO | 03046636 | 6/2003 |
| WO | 03052478 | 6/2003 |
| WO | 03053226 | 7/2003 |
| WO | 03062802 | 7/2003 |
| WO | 03105678 | 12/2003 |
| WO | 2004034869 | 4/2004 |
| WO | 2004057266 | 7/2004 |
| WO | 2004066824 | 8/2004 |
| WO | 2004088361 | 10/2004 |

(56) References Cited

FOREIGN PATENT DOCUMENTS

| WO | 2004105598 | 12/2004 |
|---|---|---|
| WO | 2005000115 | 1/2005 |
| WO | WO 2005/001401 A2 | 1/2005 |
| WO | 2005047813 | 5/2005 |
| WO | 2005054780 | 6/2005 |
| WO | 2005082225 | 9/2005 |
| WO | 2006004743 | 1/2006 |
| WO | 2006014392 | 2/2006 |
| WO | 2006038876 | 4/2006 |
| WO | 2006039091 | 4/2006 |
| WO | 2006059109 | 6/2006 |
| WO | 2006124860 | 11/2006 |
| WO | 2006130797 | 12/2006 |
| WO | 2007028531 | 3/2007 |
| WO | 2007038787 | 4/2007 |
| WO | 2007028531 | 5/2007 |
| WO | 2007083138 | 7/2007 |

OTHER PUBLICATIONS

Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.

Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) "A CW Tunable Near-infrared (1.085-1.175-um) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.
Liptak David C. et al., (2007) "On the Development of a Confocal Rayleigh-Brillouin Microscope" *American Institute of Physics* vol. 78, 016106.
Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "Increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007, "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. (Oct. 1, "Two-Wavelength Optical Coherence Tomography" Radio physics and Quantum Electronics, Kluwer Academic Publishers-Consultants. vol. 47, No. 10-1.

(56) References Cited

OTHER PUBLICATIONS

International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
International Search Report and Written Opinion dated Jan. 30, 2009 for International Application No. PCT/US2008/057835.
Fox, J. A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littrow Configuration" *Optical Fiber Communication and the National Fiber Optic Engineers Conference* Mar. 29, 2007.
Marc Nikles et al., "Brillouin gain spectrum characterization in single-mode optical fibers", *Journal of Lightwave Technology* 1997, 15 (10): 1842-1851.
Tsuyoshi Sonehara et al., "Forced Brillouin Spectroscopy Using Frequency-Tunable Continuous-Wave Lasers", *Physical Review Letters* 1995, 75 (23): 4234-4237.
Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.
Webb RH et al. "Confocal Scanning Laser Ophthalmoscope", *Applied Optics* 1987, 26 (8): 1492-1499.
Andreas Zumbusch et al. "Three-dimensional vibrational imaging by coherent anti-Stokes Raman scattering", *Physical Review Letters* 1999, 82 (20): 4142-4145.
Katrin Kneipp et al., "Single molecule detection using surface-enhanced Raman scattering (SERS)", *Physical Review Letters* 1997, 78 (9): 1667-1670.
K.J. Koski et al., "Brillouin imaging" *Applied Physics Letters* 87, 2005.
Boas et al., "Diffusing temporal light correlation for burn diagnosis", *SPIE*, 1999, 2979:468-477.

David J. Briers, "Speckle fluctuations and biomedical optics: implications and applications", *Optical Engineering*, 1993, 32(2):277-283.Clark et al., "Tracking Speckle Patterns with Optical Correlation", *SPIE*, 1992, 1772:77-87.
Clark et al., "Tracking Speckle Patterns with Optical Correlation", *SPIE*, 1992, 1772:77-87.
Facchini et al., "An endoscopic system for DSPI", *Optik*, 1993, 95(1):27-30.
Hrabovsky, M., "Theory of speckle dispacement and decorrelation: application in mechanics", *SPIE*, 1998, 3479:345-354.
Sean J. Kirkpatrick et al., "Micromechanical behavior of cortical bone as inferred from laser speckle data", *Journal of Biomedical Materials Research*, 1998, 39(3):373-379.
Sean J. Kirkpatrick et al., "Laser speckle microstrain measurements in vascular tissue", *SPIE*, 1999, 3598:121-129.
Loree et al., "Mechanical Properties of Model Atherosclerotic Lesion Lipid Pools", *Arteriosclerosis and Thrombosis*, 1994, 14(2):230-234.
Podbielska, H. "Interferometric Methods and Biomedical Research", *SPIE*, 1999, 2732:134-141.
Richards-Kortum et al., "Spectral diagnosis of atherosclerosis using an optical fiber laser catheter", *American Heart Journal*, 1989, 118(2):381-391.
Ruth, B. "Blood flow determination by the laser speckle method", *Int J Microcirc: Clin Exp*, 1990, 9:21-45.
Shapo et al., "Intravascular strain imaging: Experiments on an Inhomogeneous Phantom", *IEEE Ultrasonics Symposium* 1996, 2:1177-1180.
Shapo et al., "Ultrasonic displacement and strain imaging of coronary arteries with a catheter array", *IEEE Ultrasonics Symposium* 1995, 2:1511-1514.
Thompson et al., "Imaging in scattering media by use of laser speckle", *Opt. Soc. Am. A.*, 1997, 14(9):2269-2277.
Thompson et al., "Diffusive media characterization with laser speckle", *Applied Optics*, 1997, 36(16):3726-3734.
Tuchin, Valery V., "Coherent Optical Techniques for the Analysis of Tissue Structure and Dynamics," *Journal of Biomedical Optics*, 1999, 4(1):106-124.
M. Wussling et al., "Laser diffraction and speckling studies in skeletal and heart muscle", *Biomed, Biochim, Acta*, 1986, 45(1/2):S 23-S 27.
T. Yoshimura et al., "Statistical properties of dynamic speckles", *J. Opt. Soc. Am A*. 1986, 3(7):1032-1054.
Zimnyakov et al., "Spatial speckle correlometry in applications to tissue structure monitoring", *Applied Optics* 1997, 36(22): 5594-5607.
Zimnyakov et al., "A study of statistical properties of partially developed speckle fields as applied to the diagnosis of structural changes in human skin", *Optics and Spectroscopy*, 1994, 76(5): 747-753.
Zimnyakov et al., "Speckle patterns polarization analysis as an approach to turbid tissue structure monitoring", *SPIE* 1999, 2981:172-180.
Ramasamy Manoharan et al., "Biochemical analysis and mapping of atherosclerotic human artery using FT-IR microspectroscopy", *Atherosclerosis*, May 1993, 181-1930.
N.V. Salunke et al., "Biomechanics of Atherosclerotic Plaque" *Critical Reviews™ in Biomedical Engineering* 1997, 25(3):243-285.
D. Fu et al., "Non-invasive quantitative reconstruction of tissue elasticity using an iterative forward approach", Phys. Med. Biol. 2000 (45): 1495-1509.
S.B. Adams Jr. et al., "The use of polarization sensitive optical coherence tomography and elastography to assess connective tissue", Optical Soc. of American Washington 2002, p. 3.
International Search Report for International Patent application No. PCT/US2005/039740.
International Written Opinion for International Patent application No. PCT/US2005/039740.
International Search Report for International Patent application No. PCT/US2005/030294.
International Written Opinion for International Patent application No. PCT/US2005/043951.
International Search Report for International Patent application No. PCT/US2005/043951.

(56) References Cited

OTHER PUBLICATIONS

Erdelyi et al. "Generation of diffraction-free beams for applications in optical microlithography", J. Vac. Sci. Technol. B 15 (12), Mar./Apr. 1997, pp. 287-292.
International Search Report for International Patent application No. PCT/US2005/023664.
International Written Opinion for International Patent application No. PCT/US2005/023664.
Tearney et al., "Spectrally encoded miniature endoscopy" Optical Society of America; Optical Letters vol. 27, No. 6, Mar. 15, 2002; pp. 412-414.
Yelin et al., "Double-clad Fiber for Endoscopy" Optical Society of America; Optical Letters vol. 29, No. 20, Oct. 16, 2005; pp. 2408-2410.
International Search Report for International Patent application No. PCT/US2001/049704.
International Search Report for International Patent application No. PCT/US2004/039454.
International Written Opinion for International Patent application No. PCT/US2004/039454.
PCT International Preliminary Report on Patentability for International Application No. PCT/US2004/038404 dated Jun. 2, 2006.
Notice of Reasons for Rejection and English translation for Japanese Patent Application No. 2002-538830.
Office Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicine IX, 2005, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics SPIE USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
Office Action dated Dec. 6, 2006 for U.S. Appl. No. 10/997,789.
Elliott, K. H. "The use of commercial CCD cameras as linear detectors in the physics undergraduate teaching laboratory", European Journal of Physics 19, 1998, pp. 107-117.
Lauer, V. "New approach to optical diffraction tomography yielding a vector equation of diffraction tomography and a novel tomographic microscope", Journal of Microscopy vol. 205, Issue 2, 2002, pp. 165-176.
Yu, P. et al. "Imaging of tumor necroses using full-frame optical coherence imaging", Proceedings of SPIE vol. 4956, 2003, pp. 34-41.
Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.
Office Action dated Dec. 18, 2006 for U.S. Appl. No. 10/501,276.
Devesa, Susan S. et al. (1998) "Changing Patterns in the Incidence of Esophegeal and Gastric Carcinoma in the United States." American Cancer Society vol. 83, No. 10 pp. 2049-2053.
Barr, H et al. (2005) "Endoscopic Therapy for Barrett's Oesophaugs" Gut vol. 54:875-884.
Johnston, Mark H.(2005) "Technology Insight: Ablative Techniques for Barrett's Esophagus—Current and Emerging Trends" www.Nature.com/clinicalpractice/gasthep.
Falk, Gary W. et al. (1997) "Surveillance of Patients with Barrett's Esophagus for Dysplasia and Cancer with Ballon Cytology" Gastrorenterology vol. 112, pp. 1787-1797.
Sepchler, Stuart Jon. (1997) "Barrett's Esophagus: Should We Brush off this Balloning Problem?" Gastroenterology vol. 112, pp. 2138-2152.
Froehly, J. et al. (2003) "Multiplexed 3D Imaging Using Wavelength Encoded Spectral Interferometry: A Proof of Principle" Optics Communications vol. 222, pp. 127-136.
Kubba A.K. et al. (1999) "Role of p53 Assessment in Management of Barrett's Esophagus" Digestive Disease and Sciences vol. 44, No. 4. pp. 659-667.
Reid, Brian J. (2001) "p53 and Neoplastic Progression in Barrett's Esophagus" The American Journal of Gastroenterology vol. 96, No. 5, pp. 1321-1323.
Sharma, P. et al.(2003) "Magnification Chromoendoscopy for the Detection of Intestinal Metaplasia and Dysplasia in Barrett's Oesophagus" Gut vol. 52, pp. 24-27.
Kuipers E.J et al. (2005) "Diagnostic and Therapeutic Endoscopy" Journal of Surgical Oncology vol. 92, pp. 203-209.
Georgakoudi, Irene et al. (2001) "Fluorescence, Reflectance, and Light-Scattering Spectroscopy for Evaluating Dysplasia in Patients with Barrett's Esophagus" Gastroenterology vol. 120, pp. 1620-1629.
Adrain, Alyn L. et al. (1997) "High-Resolution Endoluminal Sonography is a Sensitive Modality for the Identification of Barrett's Meaplasia" Gastrointestinal Endoscopy vol. 46, No. 2, pp. 147-151.
Canto, Marcia Irene et al (1999) "Vital Staining and Barrett's Esophagus" Gastrointestinal Endoscopy vol. 49, No. 3, part 2, pp. 12-16.
Evans, John A. et al. (2006) "Optical Coherence Tomography to Identify Intramucosal Carcinoma and High-Grade Dysplasia in Barrett's Esophagus" Clinical Gastroenterology and Hepatology vol. 4, pp. 38-43.
Poneros, John M. et al. (2001) "Diagnosis of Specialized Intestinal Metaplasia by Optical Coherence Tomography" Gastroenterology vol. 120, pp. 7-12.
Ho, W. Y. et al. (2005) "115 KHz Tuning Repetition Rate Ultrahigh-Speed Wavelength-Swept Semiconductor Laser" Optics Letters col. 30, No. 23, pp. 3159-3161.
Brown, Stanley B. et al. (2004) "The Present and Future Role of Photodynamic Therapy in Cancer Treatment" The Lancet Oncology vol. 5, pp. 497-508.
Boogert, Jolanda Van Den et al. (1999) "Endoscopic Ablation Therapy for Barrett's Esophagua with High-Grade Dysplasia: A Review" The American Journal of Gastroenterology vol. 94, No. 5, pp. 1153-1160.
Sampliner, Richard E. et al. (1996) "Reversal of Barrett's Esophagus with Acid Suppression and Multipolar Electrocoagulation: Preliminary Results" Gastrointestinal Endoscopy vol. 44, No. 5, pp. 532-535.
Sampliner, Richard E. (2004) "Endoscopic Ablative Therapy for Barrett's Esophagus: Current Status" Gastrointestinal Endoscopy vol. 59, No. 1, pp. 66-69.
Soetikno, Roy M. et al. (2003) "Endoscopic Mucosal resection" Gastrointestinal Endoscopy vol. 57, No. 4, pp. 567-579.
Ganz, Robert A. et al. (2004) "Complete Ablation of Esophageal Epithelium with a Balloon-based Bipolar Electrode: A Phased Evalu-

(56) References Cited

OTHER PUBLICATIONS ation in the Porcine and in the Human Esophagus" *Gastrointestinal Endoscopy* vol. 60, No. 6, pp. 1002-1010.
Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.
Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.
Vogel, Alfred et al. (2003) "Mechanisms of Pulsed Laser Ablation of Biological Tissues" *American Chemical Society* vol. 103, pp. 577-644.
McKenzie, A. L. (1990) "Physics of Thermal Processes in Laser-Tissue Interaction" *Phys. Med. Biol* vol. 35, No. 9, pp. 1175-1209
Anderson, R. Rox et al. (1983) "Selective Photothermolysis Precise Microsurgery by Selective Absorption of Pulsed Radiation" *Science* vol. 220, No. 4596, pp. 524-527.
Jacques, Steven L. (1993) "Role of Tissue Optics and Pulse Duration on Tissue Effects During High-Power Laser Irradiation" *Applied Optics* vol. 32, No. 13, pp. 2447-2454.
Nahen, Kester et al. (1999) "Investigations on Acosustic On-Line Monitoring of IR Laser Ablation of burned Skin" *Lasers in Surgery and Medicine* vol. 25, pp. 69-78.
Jerath, Maya R. et al. (1993) "Calibrated Real-Time Control of Lesion Size Based on Reflectance Images" *Applied Optics* vol. 32, No. 7, pp. 1200-1209.
Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.
Deckelbaum, Lawrence I. (1994) "Coronary Laser Angioplasty" *Lasers in Surgery and Medicine* vol. 14, pp. 101-110.
Kim, B.M. et al. (1998) "Optical Feedback Signal for Ultrashort Laser Pulse Ablation of Tissue" *Applied Surface Science* vol. 127-129, pp. 857-862.
Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.
Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.
Thomsen, Sharon et al. (1990) "Microscopic Correlates of Macroscopic Optical Property Changes During Thermal Coagulation of Myocardium" *SPIE* vol. 1202, pp. 2-11.
Khan, Misban Huzaira et al. (2005) "Intradermally Focused Infrared Laser Pulses: Thermal Effects at Defined Tissue Depths" *Lasers in Surgery and Medicine* vol. 36, pp. 270-280.
Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.
Nadkarni, Seemantini K. et al (2005) "Charaterization of Atherosclerotic Plaques by Laser Speckle Imaging" *Circulation* vol. 112, pp. 885-892.
Zimnyakov, Dmitry A. et al (2002) "Speckle-Contrast Monitoring of Tissue Thermal Modification" *Applied Optics* vol. 41, No. 28, pp. 5989-5996.
Morelli, J.G., et al (1986) "Tunable Dye Laser (577 nm) Treatment of Port Wine Stains" *Lasers in Surgery and Medicine* vol. 6, pp. 94-99.
French, P.M.W. et al. (1993) "Continuous-wave Mode-Locked $Cr^{4+}$: YAG Laser" *Optics Letters* vol. 18, No. 1, pp. 39-41.
Sennaroglu, Alphan at al. (1995) "Efficient Continuous-Wave Chromium-Doped YAG Laser" *Journal of Optical Society of America* vol. 12, No. 5, pp. 930-937.
Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.
Fernández, Cabrera Delia et al. "Automated detection of retinal layer structures on optical coherence tomography images", *Optics Express* vol. 13, No. 25, Oct. 4, 2005, pp. 10200-10216.
Ishikawa, Hiroshi et al. "Macular Segmentation with optical coherence tomography", Investigative Ophthalmology & Visual Science, vol. 46, No. 6, Jun. 2005, pp. 2012-2017.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., "Applications of Fourier Transform Infrared Imaging Microscopy in Neurotoxicity", Annals New York Academy of Sciences, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-8.
PCT International Search Report and Written Opinion for Application No. PCT/US2007/066017 dated Aug. 30, 2007.

(56) References Cited

OTHER PUBLICATIONS

Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., "Speckle in Optical Coherence Tomography: An Overview", SPIE vol. 3726, pp. 450-461.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—The International Society for Optical Engineering SPIE—vol. 4001, 2000, pp. 92-101.
Lisauskas B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.
Parker K. J. et al., "Techniques for Elastic Imaging: A Review", IEEE Engineering in Medicine and Biology, Nov./Dec. 1996, pp. 52-59.
European Patent Office Search Report for Application No. 05791226.3.
Dubois Arnaud et al., "Ultrahigh-resolution OCT using white-light interference microscopy", Proceedings of SPIE, 2003, vol. 4956, pp. 14-21.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
Fujimoto et al., "High Resolution in Vivo Intra-Arterial Imaging with Optical Coherence Tomography," Official Journal of the British Cardiac Society, vol. 82, pp. 128-133 Heart, 1999.
D. Huang et al., "Optical Coherence Tomography," Science, vol. 254, pp. 1178-1181, Nov. 1991.
Tearney et al., "High-Speed Phase-and Group Delay Scanning with a Grating Based Phase Control Delay Line," Optics Letters, vol. 22, pp. 1811-1813, Dec. 1997.
Rollins, et al., "In Vivo Video Rate Optical Coherence Tomography," Optics Express, vol. 3, pp. 219-229, Sep. 1998.
Saxer, et al., High Speed Fiber-Based Polarization-Sensitive Optical Coherence Tomography of in Vivo Human Skin, Optical Society of America, vol. 25, pp. 1355-1357, Sep. 2000.
Oscar Eduardo Martinez, "3000 Times Grating Compress or with Positive Group Velocity Dispersion," IEEE, vol. QE-23, pp. 59-64, Jan. 1987.
Kulkarni, et al., "Image Enhancement in Optical Coherence Tomography Using Deconvolution," Electronics Letters, vol. 33, pp. 1365-1367, Jul. 1997.
Bashkansky, et al., "Signal Processing for Improving Field Cross-Correlation Function in Optical Coherence Tomography," Optics & Photonics News, vol. 9, pp. 8137-8138, May 1998.
Yung et al., "Phase-Domain Processing of Optical Coherence Tomography Images," Journal of Biomedical Optics, vol. 4, pp. 125-136, Jan. 1999.
Tearney, et al., "In Vivo Endoscopic Optical Biopsy with Optical Coherence Tomography," Science, vol. 276, Jun. 1997.
W. Drexler et al., "In Vivo Ultrahigh-Resolution Optical Coherence Tomography," Optics Letters vol. 24, pp. 1221-1223, Sep. 1999.
Nicusor V. Iftimia et al., "A Portable, Low Coherence Interferometry Based Instrument for Fine Needle Aspiration Biopsy Guidance," Accepted to Review of Scientific Instruments, 2005.
Abbas, G.L., V.W.S. Chan et al., "Local-Oscillator Excess-Noise Suppression for Homodyne and Heterodyne-Detection," Optics Letters, vol. 8, pp. 419-421, Aug. 1983 issue.
Agrawal, G.P., "Population Pulsations and Nondegenerate 4-Wave Mixing in Semiconductor-Lasers and Amplifiers," Journal of the Optical Society of America B-Optical Physics, vol. 5, pp. 147-159, Jan. 1998.
Andretzky, P. et al., "Optical Coherence Tomography by Spectral Radar: Improvement of Signal-to-Noise Ratio," The International Society for Optical Engineering, USA, vol. 3915, 2000.
Ballif, J. et al., "Rapid and Scalable Scans at 21 m/s in optical Low-Coherence Reflectometry," Optics Letters, vol. 22, pp. 757-759, Jun. 1997.
Barfuss H. et al., "Modified Optical Frequency-Domain Reflectometry with High Spatial-Resolution for Components of Integrated Optic Systems," Journal of Lightwave Technology, vol. 7, pp. 3-10, Jan. 1989.
Beaud, P. et al., "Optical Reflectometry with Micrometer Resolution for the Investigation of Integrated Optical-Devices," Ieee Journal of Quantum Electronics, vol. 25, pp. 755-759, Apr. 1989.
Bouma, Brett et al., "Power-Efficient Nonreciprocal Interferometer and Linear-Scanning Fiber-Optic Catheter for Optical Coherence Tomography," Optics Letters, vol. 24, pp. 531-533, Apr. 1999.
Brinkmeyer, E. et al., "Efficient Algorithm for Non-Equidistant Interpolation of Sampled Data," Electronics Letters, vol. 28, p. 693, Mar. 1992.
Brinkmeyer, E. et al., "High-Resolution OCDR in Dispersive Wave-Guides," Electronics Letters, vol. 26, pp. 413-414, Mar. 1990.
Chinn, S.R. et al., "Optical Coherence Tomography Using a Frequency-Tunable Optical Source," Optics Letters, vol. 22, pp. 340-342, Mar. 1997.
Danielson, B.L. et al., "Absolute Optical Ranging Using Low Coherence Interferometry," Applied Optics, vol. 30, p. 2975, Jul. 1991.
Dorrer, C. et al., "Spectral Resolution and Sampling Issues in Fourier-Transform Spectral Interferometry," Journal of the Optical Society of America B-Optical Physics, vol. 17, pp. 1795-1802, Oct. 2000.
Dudley, J.M. et al., "Cross-Correlation Frequency Resolved Optical Gating Analysis of Broadband Continuum Generation in Photonic Crystal Fiber: Simulations and Experiments," Optics Express, vol. 10, p. 1215, Oct. 2002.
Eickhoff, W. et al., "Optical Frequency-Domain Reflectometry in Single-Mode Fiber," Applied Physics Letters, vol. 39, pp. 693-695, 1981.
Fercher, Adolf "Optical Coherence Tomography," Journal of Biomedical Optics, vol. 1, pp. 157-173, Apr. 1996.

(56) References Cited

OTHER PUBLICATIONS

Ferreira, L.A. et al., "Polarization-Insensitive Fiberoptic White-Light Interferometry," *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver," *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.

Golubovic, B. et al., "Optical Frequency-Domain Reflectometry,Using Rapid Wavelength Tuning of a Cr4+:Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., "'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*,vol. 36, pp. 6548-6553, Sep. 1997.

Mitsui, Takahisa, "Dynamic Range of Optical Reflectometry with Spectral Interferometry," *Japanese Journal of Applied Physics Part 1-Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi,Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues by Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic

(56) References Cited

OTHER PUBLICATIONS

Tunable Filter," *IEEE Journal of Selected Topic in Quantum Electronics*, vol. 3, pp. 1087-1096, Aug. 1997.
Yun, S. H. et al., "Interrogation of Fiber Grating Sensor Arrays with a Wavelength-Swept Fiber Laser," *Optics Letters*, vol. 23, pp. 843-845, Jun. 1998.
Yung, K. M., "Phase-Domain Processing of Optical Coherence Tomography Images," *Journal of Biomedical Optics*, vol. 4, pp. 125-136, Jan. 1999.
Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.
Zorabedian, Paul et al., "Tuning Fidelity of Acoustooptically Controlled External Cavity Semiconductor-Lasers," *Journal of Lightwave Technology*, vol. 13, pp. 62-66, Jan. 1995.
Victor S. Y. Lin et al., "A Porous Silicon-Based Optical Interferometric Biosensor," *Science Magazine*, vol. 278, pp. 840-843, Oct. 31, 1997.
De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.
Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.
Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.
Roth, Jonathan E. et al., "Simplified Method for Polarization-Sensitive Optical Coherence Tomography," *Optics Letters*, vol. 26, No. 14, Jul. 15, 2001, pp. 1069-1071.
Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.
Wang, Xueding et al., "Propagation of Polarized Light in Birefringent Turbid Media: Time-Resolved Simulations," Optical Imaging Laboratory, Biomedical Engineering Program, Texas A&M University.
Wong, Brian J.F. et al., "Optical Coherence Tomography of the Rat Cochlea," Journal of *Biomedical Optics*, vol. 5, No. 4, Oct. 2000, pp. 367-370.
Yao, Gang et al., "Propagation of Polarized Light in Turbid Media: Simulated Animation Sequences," *Optics Express*, vol. 7, No. 5, Aug. 28, 2000, pp. 198-203.
Wang, Xiao-Jun et al., "Characterization of Dentin and Enamel by Use of Optical Coherence Tomography," *Applied Optics*, vol. 38, No. 10, Apr. 1, 1999, pp. 2092-2096.
De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.
Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.
Groner, Warren et al., "Orthogonal Polarization Spectral Imaging: A New Method for Study of the Microcirculation," *Nature Medicine Inc.*, vol. 5 No. 10, Oct. 1999, pp. 1209-1213.
De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.
Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.
Lu, Shih-Yau et al., "Homogeneous and Inhomogeneous Jones Matrices," *J. Opt. Soc. Am. A.*, vol. 11, No. 2, Feb. 1994, pp. 766-773.
Bickel, S. William et al., "Stokes Vectors, Mueller Matrices, and Polarized Scattered Light," *Am. J. Phys.*, vol. 53, No. 5, May 1985 pp. 468-478.
Bréhonnet, F. Le Roy et al., "Optical Media and Target Characterization by Mueller Matrix Decomposition," *J. Phys. D: Appl. Phys.* 29, 1996, pp. 34-38.
Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.
De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.
De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.
Everett, M.J. et al., "Birefringence Characterization of Biological Tissue by Use of Optical Coherence Tomography," *Optics Letters*, vol. 23, No. 3, Feb. 1, 1998, pp. 228-230.
Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.
Barakat, Richard, "Statistics of the Stokes Parameters," *J. Opt. Soc. Am. B.*, vol. 4, No. 7, Jul. 1987, pp. 1256-1263.
Schmitt, J.M. et al., "Cross-Polarized Backscatter in Optical Coherence Tomography of Biological Tissue," *Optics Letters*, vol. 23, No. 13, Jul. 1, 1998, pp. 1060-1062.
Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.
Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.
De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.
Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.
Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.
Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.
Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.
Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.
Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.
Tripathi, Renu et al., "Spectral Shaping for Non-Gaussian Source Spectra in Optical Coherence Tomography," *Optics Letters*, vol. 27, No. 6, Mar. 15, 2002, pp. 406-408.
Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.
White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

(56) References Cited

OTHER PUBLICATIONS

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.
Jiao, Shuliang et al., "Optical-Fiber-Based Mueller Optical Coherence Tomography," *Optics Letters*, vol. 28, No. 14, Jul. 15, 2003, pp. 1206-1208.
Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.
Moreau, Julien et al., "Full-Field Birefringence Imaging by Thermal-Light Polarization-Sensitive Optical Coherence Tomography I. Theory," *Applied Optics*, vol. 42, No. 19, Jul. 1, 2003, pp. 3800-3810.
Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.
Morgan, Stephen P. et al., "Surface-Reflection Elimination in Polarization Imaging of Superficial Tissue," *Optics Letters*, vol. 28, No. 2, Jan. 15, 2003, pp. 114-116.
Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.
Park, B. Hyle et al., "Real-Time Multi-Functional Optical Coherence Tomography," *Optics Express*, vol. 11, No. 7, Apr. 7, 2003, pp. 782-793.
Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.
Somervell, A.R.D. et al., "Direct Measurement of Fringe Amplitude and Phase Using a Heterodyne Interferometer Operating in Broadband Light," *Elsevier, Optics Communications*, Oct. 2003.
Stifter, D. et al., "Polarisation-Sensitive Optical Coherence Tomography for Material Characterisation and Strain-Field Mapping," Applied Physics A 76, Materials Science & Processing, Jan. 2003, pp. 947-951.
Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.
Yang, Ying et al., "Observations of Birefringence in Tissues from Optic-Fibre-Based Optical Coherence Tomography," *Measurement Science and Technology*, Nov. 2002, pp. 41-46.
Yun, S.H. et al., "High-Speed Optical Frequency-Domain Imaging," *Optics Express*, vol. 11, No. 22, Nov. 3, 2003, pp. 2953-2963.
Yun, S.H. et al., "High-Speed Spectral-Domain Optical Coherence Tomography at 1.3 µm Wavelength," *Optics Express*, vol. 11, No. 26, Dec. 29, 2003, pp. 3598-3604.
Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.
Pircher, Michael et al., "Three Dimensional Polarization Sensitive OCT of Human Skin In Vivo," 2004, *Optical Society of America*.
Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.
Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.
Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.
Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.
Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.
Park, B. Hyle et al., "Comment on Optical-Fiber-Based Mueller Optical Coherence Tomography," *Optics Letters*, vol. 29, No. 24, Dec. 15, 2004, pp. 2873-2874.
Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.
Pierce, Mark C. et al., "Collagen Denaturation can be Quantified in Burned Human Skin Using Polarization-Sensitive Optical Coherence Tomography," *Elsevier, Burns*, 2004, pp. 511-517.
Pierce, Mark C. et al., "Advances in Optical Coherence Tomography Imaging for Dermatology," *The Society for Investigative Dermatology, Inc.* 2004, pp. 458-463.
Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.
Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125
Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.
Pircher, Michael et al., "Transversal Phase Resolved Polarization Sensitive Optical Coherence Tomography," *Physics in Medicine & Biology*, 2004, pp. 1257-1263.
Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.
Strasswimmer, John et al., "Polarization-Sensitive Optical Coherence Tomographyof Invasive Basal Cell Carcinoma," *Journal of Biomedical Optics*, vol. 9, No. 2, Mar./Apr. 2004, pp. 292-298.
Todorovič, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.
Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.
Acioli, L. H., M. Ulman, et al. (1991). "Femtosecond Temporal Encoding in Barium-Titanate." *Optics Letters* 16(24): 1984-1986.
Aigouy, L., A. Lahrech, et al. (1999). "Polarization effects in apertureless scanning near-field optical microscopy: an experimental study." *Optics Letters* 24(4): 187-189.
Akiba, M., K. P. Chan, et al. (2003). "Full-field optical coherence tomography by two-dimensional heterodyne detection with a pair of CCD cameras." *Optics Letters* 28(10): 816-818.
Akkin, T., D. P. Dave, et al. (2004). "Detection of neural activity using phase-sensitive optical low-coherence reflectometry." *Optics Express* 12(11): 2377-2386.
Akkin, T., D. P. Dave, et al. (2003). "Surface analysis using phase sensitive optical low coherence reflectometry." *Lasers in Surgery and Medicine*: 4-4.
Akkin, T., D. P. Dave, et al. (2003). "Imaging tissue response to electrical and photothermal stimulation with nanometer sensitivity." *Lasers in Surgery and Medicine* 33(4): 219-225.
Akkin, T., T. E. Milner, et al. (2002). "Phase-sensitive measurement of birefringence change as an indication of neural functionality and diseases." *Lasers in Surgery and Medicine*: 6-6.
Andretzky, P., Lindner, M.W., Herrmann, J.M., Schultz, A., Konzog, M., Kiesewetter, F., Haeusler, G. (1999). "Optical coherence

(56) References Cited

OTHER PUBLICATIONS tomography by 'spectral radar': Dynamic range estimation and in vivo measurements of skin." *Proceedings of SPIE—The International Society for Optical Engineering* 3567: pp. 78-87.
Antcliff, R. J., T. J. ffytche, et al. (2000). "Optical coherence tomography of melanocytoma." *American Journal of Ophthalmology* 130(6): 845-7.
Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.
Anvari, B., T. E. Milner, et al. (1995). "Selective Cooling of Biological Tissues—Application For Thermally Mediated Therapeutic Procedures." *Physics in Medicine and Biology* 40(2): 241-252.
Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.
Arend, O., M. Ruffer, et al. (2000). "Macular circulation in patients with diabetes mellitus with and without arterial hypertension." *British Journal of Ophthalmology* 84(12): 1392-1396.
Arimoto, H. and Y. Ohtsuka (1997). "Measurements of the complex degree of spectral coherence by use of a wave-front-folded interferometer." *Optics Letters* 22(13): 958-960.
Azzolini, C., F. Patelli, et al. (2001). "Correlation between optical coherence tomography data and biomicroscopic interpretation of idiopathic macular hole." *American Journal of Ophthalmology* 132(3): 348-55.
Baba, T., K. Ohno-Matsui, et al. (2002). "Optical coherence tomography of choroidal neovascularization in high myopia." *Acta Ophthalmoloqica Scandinavica* 80(1): 82-7.
Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.
Baney, D. M. and W. V. Sorin (1993). "Extended-Range Optical Low-Coherence Reflectometry Using a Recirculating Delay Technique." *Ieee Photonics Technology Letters* 5(9): 1109-1112.
Baney, D. M., B. Szafraniec, et al. (2002). "Coherent optical spectrum analyzer." *Ieee Photonics Technology Letters* 14(3): 355-357.
Barakat, R. (1981). "Bilinear Constraints between Elements of the 4by4 Mueller-Jones Transfer-Matrix of Polarization Theory." *Optics Communications* 38(3): 159-161.
Barakat, R. (1993). "Analytic Proofs of the Arago-Fresnel Laws for the Interference of Polarized-Light." *Journal of the Optical Society of America a-Optics Image Science and Vision* 10(1): 180-185.
Barbastathis, G. and D. J. Brady (1999). "Multidimensional tomographic imaging using volume holography." *Proceedings of the Ieee* 87(12): 2098-2120.
Bardal, S., A. Kamal, et al. (1992). "Photoinduced Birefringence in Optical Fibers—A Comparative-Study of Low-Birefringence and High-Birefringence Fibers." *Optics Letters* 17(6): 411-413.
Barsky, S. H., S. Rosen, et al. (1980). "Nature and Evolution of Port Wine Stains—Computer-Assisted Study." *Journal of Investigative Dermatology* 74(3): 154-157.
Barton, J. K., J. A. Izatt, et al. (1999). "Three-dimensional reconstruction of blood vessels from in vivo color Doppler optical coherence tomography images." *Dermatology* 198(4): 355-361.
Barton, J. K., A. Rollins et al. (2001). "Photothermal coagulation of blood vessels: a comparison of high-speed optical coherence tomography and numerical modelling." *Physics in Medicine and Biology* 46.
Barton, J. K., A. J. Welch, et al. (1998). "Investigating pulsed dye laser-blood vessel interaction with color Doppler optical coherence tomography." *Optics Express* 3.
Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.
Baumgartner, A., S. Dichtl, et al. (2000). "Polarization-sensitive optical coherence tomography of dental structures." *Caries Research* 34(1): 59-69.
Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.
Baumgartner, A., C. K. Hitzenberger, et al. (1998). "Signal and resolution enhancements in dual beam optical coherence tomography of the human eye." *Journal of Biomedical Optics* 3(1): 45-54.
Beaurepaire, E., P. Gleyzes, et at. (1998). *Optical coherence microscopy for the in-depth study of biological structures: System based on a parallel detection scheme*, Proceedings of SPIE—The International Society for Optical Engineering.
Beaurepaire, E., L. Moreaux, et al. (1999). "Combined scanning optical coherence and two-photon-excited fluorescence microscopy." *Optics Letters* 24(14): 969-971.
Bechara, F. G., T. Gambichler, et al. (2004). "Histomorphologic correlation with routine histology and optical coherence tomography." *Skin Research and Technology* 10 (3): 169-173.
Bechmann, M., M. J. Thiel, et al. (2000). "Central corneal thickness determined with optical coherence tomography in various types of glaucoma. [see comments]." *British Journal of Ophthalmology* 84(11): 1233-7.
Bek, T. and M. Kandi (2000). "Quantitative anomaloscopy and optical coherence tomography scanning in central serous chorioretinopathy." *Acta Ophthalmologica Scandinavica* 78(6): 632-7.
Benoit, A. M., K. Naoun, et al. (2001). "Linear dichroism of the retinal nerve fiber layer expressed with Mueller matrices." *Applied Optics* 40(4): 565-569.
Bicout, D., C. Brosseau, et al. (1994). "Depolarization of Multiply Scattered Waves by Spherical Diffusers—Influence of the Size Parameter." *Physical Review* E 49(2): 1767-1770.
Blanchot, L., M. Lebec, et al. (1997). *Low-coherence in depth microscopy for biological tissues imaging: Design of a real time control system*. Proceedings of SPIE—The International Society for Optical Engineering.
Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.
Blumenthal, E. Z., J. M. Williams, et al. (2000). "Reproducibility of nerve fiber layer thickness measurements by use of optical coherence tomography." *Ophthalmology* 107(12): 2278-82.
Boppart, S. A., B. E. Bouma, et al. (1996). "Imaging developing neural morphology using optical coherence tomography." *Journal of Neuroscience Methods* 70.
Boppart, S. A., B. E. Bouma, et al. (1997). "Forward-imaging instruments for optical coherence tomography." *Optics Letters* 22.
Boppart, S. A., B. E. Bouma, et al. (1998). "Intraoperative assessment of microsurgery with three-dimensional optical coherence tomography." *Radiology* 208: 81-86.
Boppart, S. A., J. Herrmann, et al. (1999). "High-resolution optical coherence tomography-guided laser ablation of surgical tissue." *Journal of Surgical Research* 82(2): 275-84.
Bouma, B. E. and J. G. Fujimoto (1996). "Compact Kerr-lens mode-locked resonators." *Optics Letters* 21. 134-136.
Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.
Bouma, B. E., M. Ramaswamy-Paye, et al. (1997). "Compact resonator designs for mode-locked solid-state lasers." *Applied Physics B (Lasers and Optics)* B65. 213-220.
Bouma, B. E. and G. J. Tearney (2002). "Clinical imaging with optical coherence tomography." *Academic Radiology* 9(8): 942-953.
Bouma, B. E., G. J. Tearney, et al. (1996). "Self-phase-modulated Kerr-lens mode-locked Cr:forsterite laser source for optical coherence tomography." *Optics Letters* 21(22): 1839.

(56) References Cited

OTHER PUBLICATIONS

Bouma, B. E., G. J. Tearney, et al. (2000). "High-resolution imaging of the human esophagus and stomach in vivo using optical coherence tomography." *Gastrointestinal Endoscopy* 51(4): 467-474.
Bouma, B. E., G. J. Tearney, et al. (2003). "Evaluation of intracoronary stenting by intravascular optical coherence tomography." *Heart* 89(3): 317-320.
Bourquin, S., V. Monterosso, et al. (2000). "Video-rate optical low-coherence reflectometry based on a linear smart detector array." *Optics Letters* 25(2): 102-104.
Bourquin, S., P. Seitz, et al. (2001). "Optical coherence topography based on a two-dimensional smart detector array." *Optics Letters* 26(8): 512-514.
Bouzid, A., M. A. G. Abushagur, et al. (1995). "Fiber-optic four-detector polarimeter." *Optics Communications* 118(3-4): 329-334.
Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.
Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.
Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.
Brand, S., J. M. Poneros, et al. (2000). "Optical coherence tomography in the gastrointestinal tract." *Endoscopy* 32(10): 796-803.
Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.
Brezinski, M. E., G. J. Tearney, et al. (1996). "Imaging of coronary artery microstructure (in vitro) with optical coherence tomography." *American Journal of Cardiology* 77 (1): 92-93.
Brezinski, M. E., G. J. Tearney, et al. (1996). "Optical coherence tomography for optical biopsy—Properties and demonstration of vascular pathology." *Circulation* 93(6): 1206-1213.
Brezinski, M. E., G. J. Tearney, et al. (1997). "Assessing atherosclerotic plaque morphology: Comparison of optical coherence tomography and high frequency intravascular ultrasound." *Heart* 77(5): 397-403.
Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.
Brosseau, C. and D. Bicout (1994). "Entropy Production in Multiple-Scattering of Light by a Spatially Random Medium." *Physical Review* E 50(6): 4997-5005.
Burgoyne, C. F., D. E. Mercante, et al. (2002). "Change detection in regional and volumetric disc parameters using longitudinal confocal scanning laser tomography." *Ophthalmology* 109(3): 455-66.
Candido, R. and T. J. Allen (2002). "Haemodynamics in microvascular complications in type 1 diabetes." *Diabetes-Metabolism Research and Reviews* 18(4): 286-304.
Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.
Cense, B., N. Nassif, et al. (2004). "Ultrahigh-Resolution High-Speed Retinal Imaging Using Spectral-Domain Optical Coherence Tomography." *Optics Express* 12(11): 2435-2447.
Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.
Chartier, T., A. Hideur, et al. (2001). "Measurement of the elliptical birefringence of single-mode optical fibers." *Applied Optics* 40(30): 5343-5353.
Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.
Chen, Z. P., T. E. Milner, et al. (1997). "Optical Doppler tomographic imaging of fluid flow velocity in highly scattering media." *Optics Letters* 22(1): 64-66.
Chen, Z. P., T. E. Milner, et al. (1997). "Noninvasive imaging of in vivo blood flow velocity using optical Doppler tomography." *Optics Letters* 22(14): 1119-1121.
Chen, Z. P., Y. H. Zhao, et al. (1999). "Optical Doppler tomography." *Ieee Journal of Selected Topics in Quantum Electronics* 5(4): 1134-1142.
Cheong, W. F., S. A. Prahl, et al. (1990). "A Review of the Optical-Properties of Biological Tissues." *Ieee Journal of Quantum Electronics* 26(12): 2166-2185.
Chernikov, S. V., Y. Zhu, et al. (1997). "Supercontinuum self-Q-switched ytterbium fiber laser." *Optics Letters* 22(5): 298-300.
Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.
Choma, M. A., M. V. Sarunic, et al. (2003). "Sensitivity advantage of swept source and Fourier domain optical coherence tomography." *Optics Express* 11(18): 2183-2189.
Choma, M. A., C. H. Yang, et al. (2003). "Instantaneous quadrature low-coherence interferometry with 3×3 fiber-optic couplers." *Optics Letters* 28(22): 2162-2164.
Choplin, N. T. and D. C. Lundy (2001). "The sensitivity and specificity of scanning laser polarimetry in the detection of glaucoma in a clinical setting." *Ophthalmology* 108 (5): 899-904.
Christens Barry, W. A., W. J. Green, et al. (1996). "Spatial mapping of polarized light transmission in the central rabbit cornea." *Experimental Eye Research* 62(6): 651-662.
Chvapil, M., D. P. Speer, et al. (1984). "Identification of the depth of burn injury by collagen stainability." *Plastic & Reconstructive Surgery* 73(3): 438-41.
Cioffi, G. A. (2001). "Three common assumptions about ocular blood flow and glaucoma." *Survey of Ophthalmology* 45: S325-S331.
Coleman, A. L. (1999). "Glaucoma." *Lancet* 354(9192): 1803-10.
Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.
Collaborative Normal-Tension Glaucoma Study Group (1998). "The effectiveness of intraocular pressure reduction in the treatment of normal-tension glaucoma." *Am J Ophthalmol* 126: 498-505.
Collaborative Normal-Tension Glaucoma Study Group (2001). "Natural History of Normal-Tension Glaucoma." *Ophthalmology* 108: 247-253.
Colston, B. W., M. J. Everett, et al. (1998). "Imaging of hard- and soft-tissue structure in the oral cavity by optical coherence tomography." *Applied Optics* 37(16): 3582-3585.
Colston, B. W., U. S. Sathyam, et al. (1998). "Dental OCT." *Optics Express* 3(6): 230-238.
Congdon, N. G., D. S. Friedman, et al. (2003). "Important causes of visual impairment in the world today." *Jama-Journal of the American Medical Association* 290(15): 2057-2060.
Cregan, R. F., B. J. Mangan, et al. (1999). "Single-mode photonic band gap guidance of light in air." *Science* 285(5433): 1537-1539.
DalMolin, M., A. Galtarossa, et al. (1997). "Experimental investigation of linear polarization in high-birefringence single-mode fibers." *Applied Optics* 36(12): 2526-2528.
Danielson, B. L. and C. D. Whittenberg (1987). "Guided-Wave Reflectometry with Micrometer Resolution." *Applied Optics* 26(14): 2836-2842.

(56) References Cited

OTHER PUBLICATIONS

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of precancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo Oct imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation*. Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. *Ocular partial coherence interferometry*. Proceedings of SPIE—The International Society for Optical Engineering (1996).

(56) References Cited

OTHER PUBLICATIONS

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*. Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth-scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review A* 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics* Draft Copy.

(56) References Cited

OTHER PUBLICATIONS

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.
Hale, G. M. and M. R. Querry (1973). "Optical-Constants of Water in 200-Nm to 200-Mum Wavelength Region." *Applied Optics* 12(3): 555-563.
Hammer, D. X., R. D. Ferguson, et al. (2002). "Image stabilization for scanning laser ophthalmoscopy." *Optics Express* 10(26): 1542.
Hara, T., Y. Ooi, et al. (1989). "Transfer Characteristics of the Microchannel Spatial Light-Modulator." *Applied Optics* 28(22): 4781-4786.
Harland, C. C., S. G. Kale, et al. (2000). "Differentiation of common benign pigmented skin lesions from melanoma by high-resolution ultrasound." *British Journal of Dermatology* 143(2): 281-289.
Hartl, I., X. D. Li, et al. (2001). "Ultrahigh-resolution optical coherence tomography using continuum generation in an air-silica microstructure optical fiber." *Optics Letters* 26(9): 608-610.
Hassenstein, A., A. A. Bialasiewicz, et al. (2000). "Optical coherence tomography in uveitis patients." *American Journal of Ophthalmology* 130(5): 669-70.
Hattenhauer, M. G., D. H. Johnson, et al. (1998). "The probability of blindness from open-angle glaucoma. [see comments]." *Ophthalmology* 105(11): 2099-104.
Hausler, G., J. M. Herrmann, et al. (1996). "Observation of light propagation in volume scatterers with 10(11)-fold slow motion." *Optics Letters* 21(14): 1087-1089.
Hazebroek, H. F. and A. A. Holscher (1973). "Interferometric Ellipsometry." *Journal of Physics E-Scientific Instruments* 6(9): 822-826.
Hazebroek, H. F. and W. M. Visser (1983). "Automated Laser Interferometric Ellipsometry and Precision Reflectometry." *Journal of Physics E-Scientific Instruments* 16(7): 654-661.
He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.
Hee, M. R., J. A. Izatt, et al. (1993). "Femtosecond Transillumination Optical Coherence Tomography." *Optics Letters* 18(12): 950-952.
Hee, M. R., J. A. Izatt, et al. (1995). "Optical coherence tomography of the human retina." *Archives of Ophthalmology* 113(3): 325-32.
Hee, M. R., C. A. Puliafito, et al. (1998). "Topography of diabetic macular edema with optical coherence tomography." *Ophthalmology* 105(2): 360-70.
Hee, M. R., C. A. Puliafito, et al. (1995). "Quantitative assessment of macular edema with optical coherence tomography." *Archives of Ophthalmology* 113(8): 1019-29.
Hellmuth, T. and M. Welle (1998). "Simultaneous measurement of dispersion, spectrum, and distance with a fourier transform spectrometer." *Journal of Biomedical Optics* 3(1): 7-11.
Hemenger, R. P. (1989). "Birefringence of a medium of tenuous parallel cylinders." *Applied Optics* 28(18): 4030-4034.
Henry, M. (1981). "Fresnel-Arago Laws for Interference in Polarized-Light—Demonstration Experiment." *American Journal of Physics* 49(7): 690-691.
Herz, P. R., Y. Chen, et al. (2004). "Micromotor endoscope catheter for in vivo, ultrahigh-resolution optical coherence tomography." *Optics Letters* 29(19): 2261-2263.
Hirakawa, H., H. Iijima, et al. (1999). "Optical coherence tomography of cystoid macular edema associated with retinitis pigmentosa." *American Journal of Ophthalmology* 128(2): 185-91.
Hitzenberger, C. K., A. Baumgartner, et al. (1994). "Interferometric Measurement of Corneal Thickness with Micrometer Precision." *American Journal of Ophthalmology* 118(4): 468-476.
Hitzenberger, C. K., A. Baumgartner, et al. (1999). "Dispersion effects in partial coherence interferometry: Implications for intraocular ranging." *Journal of Biomedical Optics* 4(1): 144-151.
Hitzenberger, C. K., A. Baumgartner, et al. (1998). "Dispersion induced multiple signal peak splitting in partial coherence interferometry." *Optics Communications* 154 (4): 179-185.
Hitzenberger, C. K., M. Danner, et al. (1999). "Measurement of the spatial coherence of superluminescent diodes." *Journal of Modern Optics* 46(12): 1763-1774.
Hitzenberger, C. K. and A. F. Fercher (1999). "Differential phase contrast in optical coherence tomography." *Optics Letters* 24(9): 622-624.
Hitzenberger, C. K., M. Sticker, et al. (2001). "Differential phase measurements in low-coherence interferometry without 2 pi ambiguity." *Optics Letters* 26(23): 1864-1866.
Hoeling, B. M., A. D. Fernandez, et al. (2000). "An optical coherence microscope for 3-dimensional imaging in developmental biology." *Optics Express* 6(7): 136-146.
Hoerauf, H., C. Scholz, et al. (2002). "Transscleral optical coherence tomography: a new imaging method for the anterior segment of the eye." *Archives of Ophthalmology* 120(6): 816-9.
Hoffmann, K., M. Happe, et al. (1998). "Optical coherence tomography (OCT) in dermatology." *Journal of Investigative Dermatology* 110(4): 583-583.
Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.
Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.
Holland, A. J. A., H. C. O. Martin, et al. (2002). "Laser Doppler imaging prediction of burn wound outcome in children." *Burns* 28(1): 11-17.
Notate, K. and T. Okugawa (1994). "Optical Information-Processing by Synthesis of the Coherence Function." *Journal of Lightwave Technology* 12(7): 1247-1255.
Hourdakis, C. J. and A. Perris (1995). "A Monte-Carlo Estimation of Tissue Optical-Properties for Use in Laser Dosimetry." *Physics in Medicine and Biology* 40(3): 351-364.
Hu, Z., F. Li, et al. (2000). "Wavelength-tunable narrow-linewidth semiconductor fiber-ring laser." *IEEE Photonics Technology Letters* 12(8): 977-979.
Huang, F., W. Yang, et al. (2001). "Quadrature spectral interferometric detection and pulse shaping." *Optics Letters* 26(6): 382-384.
Huang, X. R. and R. W. Knighton (2002). "Linear birefringence of the retinal nerve fiber layer measured in vitro with a multispectral imaging micropolarimeter." *Journal of Biomedical Optics* 7(2): 199-204.
Huber, R., M. Wojtkowski, et al. (2005). "Amplified, frequency swept lasers for frequency domain reflectometry and OCT imaging: design and scaling principles." *Optics Express* 13(9): 3513-3528.
Hunter, D. G., J. C. Sandruck, et al. (1999). "Mathematical modeling of retinal birefringence scanning." *Journal of the Optical Society of America a-Optics Image Science and Vision* 16(9): 2103-2111.
Hurwitz, H. H. and R. C. Jones (1941). "A new calculus for the treatment of optical systems II. Proof of three general equivalence theorems." *Journal of the Optical Society of America* 31(7): 493-499.
Huttner, B., C. De Barros, et al. (1999). "Polarization-induced pulse spreading in birefringent optical fibers with zero differential group delay." *Optics Letters* 24(6): 370-372.
Huttner, B., B. Gisin, et al. (1999). "Distributed PMD measurement with a polarization-OTDR in optical fibers." *Journal of Lightwave Technology* 17(10): 1843-1848.
Huttner, B., J. Reecht, et al. (1998). "Local birefringence measurements in single-mode fibers with coherent optical frequency-domain reflectometry." *Ieee Photonics Technology Letters* 10(10): 1458-1460.
Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.
Hyde, S. C. W., N. P. Barry, et al. (1995). "Depth-Resolved Holographic Imaging through Scattering Media by Photorefraction." *Optics Letters* 20(11): 1331-1333..

(56) References Cited

OTHER PUBLICATIONS

Iftimia, N. V., B. E. Bouma, et al. (2004). "Adaptive ranging for optical coherence tomography."*Optics Express* 12(17): 4025-4034.
Iida, T., N. Hagimura, et al. (2000). "Evaluation of central serous chorioretinopathy with optical coherence tomography." *American Journal of Ophthalmology* 129(1): 16-20.
Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.
Indebetouw, G. and P. Klysubun (2000). "Imaging through scattering media with depth resolution by use of low-coherence gating in spatiotemporal digital holography." *Optics Letters* 25(4): 212-214.
Ip, M. S., B. J. Baker, et al. (2002). "Anatomical outcomes of surgery for idiopathic macular hole as determined by optical coherence tomography." *Archives of Ophthalmology* 120(1): 29-35.
Ismail, R., V. Tanner, et al. (2002). "Optical coherence tomography imaging of severe commotio retinae and associated macular hole." *British Journal of Ophthalmology* 86(4): 473-4.
Izatt, J. A., M. R. Hee, et al. (1994). "Optical Coherence Microscopy in Scattering Media." *Optics Letters* 19(8): 590-592.
Izatt, J. A., M. R. Hee, et al. (1994). "Micrometer-scale resolution imaging of the anterior eye in vivo with optical coherence tomography." *Archives of Ophthalmology* 112 (12): 1584-9.
Izatt, J. A., M. D. Kulkarni, et al. (1997). "In vivo bidirectional color Doppler flow imaging of picoliter blood volumes using optical coherence tomography." *Optics Letters* 22(18): 1439-1441.
Izatt, J. A., M. D. Kulkarni, et al. (1996). "Optical coherence tomography and microscopy in gastrointestinal tissues." *IEEE Journal of Selected Topics in Quantum Electronics* 2(4): 1017.
Jacques, S. L., J. S. Nelson, et al. (1993). "Pulsed Photothermal Radiometry of Port-Wine-Stain Lesions." *Applied Optics* 32(13): 2439-2446.
Jacques, S. L., J. R. Roman, et al. (2000). "Imaging superficial tissues with polarized light." *Lasers in Surgery and Medicine* 26(2): 119-129.
Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.
Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.
Jang, I. K., G. J. Tearney, et al. (2000). "Comparison of optical coherence tomography and intravascular ultrasound for detection of coronary plaques with large lipid-core in living patients." *Circulation* 102(18): 509-509.
Jeng, J. C., A. Bridgeman, et al. (2003). "Laser Doppler imaging determines need for excision and grafting in advance of clinical judgment: a prospective blinded trial." *Burns* 29(7): 665-670.
Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.
Johnson, C. A., J. L. Keltner, et al. (2002). "Baseline visual field characteristics in the ocular hypertension treatment study." *Ophthalmology* 109(3): 432-7.
Jones, R. C. (1941). "A new calculus for the treatment of optical systems III. The Sohncke theory of optical activity." *Journal of the Optical Society of America* 31 (7): 500-503.
Jones, R. C. (1941). "A new calculus for the treatment of optical systems I. Description and discussion of the calculus." *Journal of the Optical Society of America* 31(7): 488-493.
Jones, R. C. (1942). "A new calculus for the treatment of optical systems. IV." *Journal of the Optical Society of America* 32(8): 486-493.
Jones, R. C. (1947). "A New Calculus for the Treatment of Optical Systems 6. Experimental Determination of the Matrix." *Journal of the Optical Society of America* 37(2): 110-112.
Jones, R. C. (1947). "A New Calculus for the Treatment of Optical Systems .5. A More General Formulation, and Description of Another Calculus." *Journal of the Optical Society of America* 37(2): 107-110.
Jones, R. C. (1948). "A New Calculus for the Treatment of Optical Systems .7. Properties of the N-Matrices." *Journal of the Optical Society of America* 38(8): 671-685.
Jones, R. C. (1956). "New Calculus for the Treatment of Optical Systems .8. Electromagnetic Theory." *Journal of the Optical Society of America* 46(2): 126-131.
Jopson, R. MThe ., L. E. Nelson, et al. (1999). "Measurement of second-order polarization-mode dispersion vectors in optical fibers." *Ieee Photonics Technology Letters* 11 (9): 1153-1155.
Jost, B. M., A. V. Sergienko, et al. (1998). "Spatial correlations of spontaneously down-converted photon pairs detected with a single-photon-sensitive CCD camera." *Optics Express* 3(2): 81-88.
Kaplan, B., E. Compain, et al. (2000). "Phase-modulated Mueller ellipsometry characterization of scattering by latex sphere suspensions." *Applied Optics* 39 (4): 629-636.
Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.
Kasuga, Y., J. Arai, et al. (2000). "Optical coherence tomoghraphy to confirm early closure of macular holes." *American Journal of Ophthalmology* 130(5): 675-6.
Kaufman, T., S. N. Lusthaus, et al. (1990). "Deep Partial Skin Thickness Burns—a Reproducible Animal-Model to Study Burn Wound-Healing." *Burns* 16(1): 13-16.
Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.
Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.
Kesen, M. R., G. L. Spaeth, et al. (2002). "The Heidelberg Retina Tomograph vs clinical impression in the diagnosis of glaucoma." *American Journal of Ophthalmology* 133(5): 613-6.
Kienle, A. and R. Hibst (1995). "A New Optimal Wavelength for Treatment of Port-Wine Stains." *Physics in Medicine and Biology* 40(10): 1559-1576.
Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.
Kim, B. Y. and S. S. Choi (1981). "Analysis and Measurement of Birefringence in Single-Mode Fibers Using the Backscattering Method." *Optics Letters* 6(11): 578-580.
Kimel, S., L. O. Svaasand, et al. (1994). "Differential Vascular-Response to Laser Photothermolysis." *Journal of Investigative Dermatology* 103(5): 693-700.
Kloppenberg, F. W. H., G. Beerthuizen, et al. (2001). "Perfusion of burn wounds assessed by Laser Doppler Imaging is related to burn depth and healing time." *Burns* 27(4): 359-363.
Knighton, R. W. and X. R. Huang (2002). "Analytical methods for scanning laser polarimetry." *Optics Express* 10(21): 1179-1189.
Knighton, R. W., X. R. Huang, et al. (2002). "Analytical model of scanning laser polarimetry for retinal nerve fiber layer assessment." *Investigative Ophthalmology & Visual Science* 43(2): 383-392.
Knuettel, A. R. S., Joseph M.; Shay, M.; Knutson, Jay R. (1994). "Stationary low-coherence light imaging and spectroscopy using a CCD camera." *Proc. SPIE* , vol. 2135: p. 239-250.
Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

(56) References Cited

OTHER PUBLICATIONS

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth—independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jong, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

(56) References Cited

OTHER PUBLICATIONS

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics* Part 1—Regular Papers Short Notes & Review Papers 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, MethodsR, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multifunctional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—A Technique for the Measurement of Field Distributions." *Applied Optics* 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

(56) References Cited

OTHER PUBLICATIONS

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3×3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., E.M.; Taylor, C.M.; Selviah, D.R.; Day, S.E.; Commander, L.G. "Variable-Focus Microlenses as a Potential Technology for Endoscopy."

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter-endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jong, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

(56) References Cited

OTHER PUBLICATIONS

Wang, X. J., T. E. Milner, et al. (1995). "Characterization of Fluid-Flow Velocity by Optical Doppler Tomography." *Optics Letters* 20(11): 1337-1339.
Wang, Y. M., J. S. Nelson, et al. (2003). "Optimal wavelength for ultrahigh-resolution optical coherence tomography." *Optics Express* 11(12): 1411-1417.
Wang, Y. M., Y. H. Zhao, et al. (2003). "Ultrahigh-resolution optical coherence tomography by broadband continuum generation from a photonic crystal fiber." *Optics Letters* 28(3): 182-184.
Watkins, L. R., S. M. Tan, et al. (1999). "Determination of interferometer phase distributions by use of wavelets." *Optics Letters* 24(13): 905-907.
Wetzel, J. (2001). "Optical coherence tomography in dermatology: a review." *Skin Research and Technology* 7(1): 1-9.
Wentworth, R. H. (1989). "Theoretical Noise Performance of Coherence-Multiplexed Interferometric Sensors." *Journal of Lightwave Technology* 7(6): 941-956.
Westphal, V., A. M. Rollins, et al. (2002). "Correction of geometric and refractive image distortions in optical coherence tomography applying Fermat's principle." *Optics Express* 10(9): 397-404.
Westphal, V., S. Yazdanfar, et al. (2002). "Real-time, high velocity-resolution color Doppler optical coherence tomography." *Optics Letters* 27(1): 34-36.
Williams, P. A. (1999). "Rotating-wave-plate Stokes polarimeter for differential group delay measurements of polarization-mode dispersion." *Applied Optics* 38(31): 6508-6515.
Wojtkowski, M., T. Bajraszewski, et al. (2003). "Real-time in vivo imaging by high-speed spectral optical coherence tomography." *Optics Letters* 28(19): 1745-1747.
Wojtkowski, M., A. Kowalczyk, et al. (2002). "Full range complex spectral optical coherence tomography technique in eye imaging." *Optics Letters* 27(16): 1415-1417.
Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.
Yabushita, H. B., B.E.; Houser, S.L.; Aretz, H.T.; Jang, I.; Schlendorf, K.H.; Kauffman, C.R.; Shishkov, M.; Halpern, E.F.; Tearney, G.J. "Measurement of Thin Fibrous Caps in Atherosclerotic Plaques by Optical Coherence Tomography."
Yang, C., A. Wax, et al. (2001). "Phase-dispersion optical tomography." *Optics Letters* 26(10): 686-688.
Yang, C., A. Wax, et al. (2001). "Phase-referenced interferometer with subwavelength and subhertz sensitivity applied to the study of cell membrane dynamics." *Optics Letters* 26(16): 1271-1273.
Yang, C. H., A. Wax, et al. (2001). "Phase-dispersion optical tomography." *Optics Letters* 26(10): 686-688.
Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." Optics Communications 208(4-6): 209-214.
Yang, V. X. D., M. L. Gordon, et al. (2003). "High speed, wide velocity dynamic range Doppler optical coherence tomography (Part I): System design, signal processing, and performance." *Optics Express* 11(7): 794-809.
Yang, V. X. D., M. L. Gordon, et al. (2003). "High speed, wide velocity dynamic range Doppler optical coherence tomography (Part II): Imaging in vivo cardiac dynamics of *Xenopus laevis*." *Optics Express* 11(14): 1650-1658.
Yang, V. X. D., M. L. Gordon, et al. (2003). "High speed, wide velocity dynamic range Doppler optical coherence tomography (Part II): in vivo endoscopic imaging of blood flow in the rat and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-referenced Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13) : 424-431.
Yazdanfar, S., A. M. Rollins, et al. (2000). "Imaging and velocimetry of the human retinal circulation with color Doppler optical coherence tomography." *Optics Letters* 25(19): 1448-1450.
Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.
Yazdanfar, S., A. M. Rollins, et al. (2003). "In vivo imaging of human retinal flow dynamics by color Doppler optical coherence tomography." *Archives of Ophthalmology* 121(2): 235-239.
Yazdanfar, S., C. H. Yang, et al. (2005). "Frequency estimation precision in Doppler optical coherence tomography using the Cramer-Rao lower bound." *Optics Express* 13(2): 410-416.
Yun, S. H., C. Boudoux, et al. (2004). "Extended-cavity semiconductor wavelength-swept laser for biomedical imaging." *Ieee Photonics Technology Letters* 16(1): 293-295.
Yun, S. H., C. Boudoux, et al. (2003). "High-speed wavelength-swept semiconductor laser with a polygon-scanner-based wavelength filter." *Optics Letters* 28(20): 1981-1983.
Yun, S. H., G. J. Tearney, et al. (2004). "Pulsed-source and swept-source spectral-domain optical coherence tomography with reduced motion artifacts." *Optics Express* 12(23) 5614-5624.
Yun, S. H., G. J. Teamey, et al. (2004). "Removing the depth-degeneracy in optical frequency domain imaging with frequency shifting." *Optics Express* 12(20): 4822-4828.
Yun, S. H., G. J. Tearney, et al. (2004). "Motion artifacts in optical coherence tomography with frequency-domain ranging." *Optics Express* 12(13): 2977-2998.
Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.
Zhang, Y., M. Sato, et al. (2001). "Numerical investigations of optimal synthesis of several low coherence sources for resolution improvement." *Optics Communications* 192(3-6): 183-192.
Zhang, Y., M. Sato, et al. (2001). "Resolution improvement in optical coherence tomography by optimal synthesis of light-emitting diodes." *Optics Letters* 26(4): 205-207.
Zhao, Y., Z. Chen, et al. (2002). "Real-time phase-resolved functional optical coherence tomography by use of optical Hilbert transformation." *Optics Letters* 27(2): 98-100.
Zhao, Y. H., Z. P. Chen, et al. (2000). "Doppler standard deviation imaging for clinical monitoring of in vivo human skin blood flow." *Optics Letters* 25(18): 1358-1360.
Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.
Zhou, D., P. R. Prucnal, et al. (1998). "A widely tunable narrow linewidth semiconductor fiber ring laser." *IEEE Photonics Technology Letters* 10(6): 781-783.
Zuluaga, A. F. and R. Richards-Kortum (1999). "Spatially resolved spectral interferometry for determination of subsurface structure." *Optics Letters* 24(8): 519-521.

(56) References Cited

OTHER PUBLICATIONS

Zvyagin, A. V., J. B. FitzGerald, et al. (2000). "Real-time detection technique for Doppler optical coherence tomography." *Optics Letters* 25(22): 1645-1647.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
Poneros er al: "Optical Coherence Tomography of the Biliary Tree During ERCP", Gastrointestinal Endoscopy, Elsevier, NL, vol. 55, No. 1, Jan. 1, 2002, pp. 84-88.
Fu L e tal: double-Clad Photonic Crystal Fiber Coupler for compact Nonlinear Optical Microscopy Imaging, Optics Letters, OSA, Optical Society of America, vol. 31, No. 10, May 15, 2006, pp. 1471-1473.
Japanese language Appeal Decision dated Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP 2008-533712.
R. Haggit et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease," Gut, vol. 45, pp. 798-803.
O'Reich et al., (2000) "Expression of Oestrogen and Progesterone Receptors in Low-Grade Endometrial Strinak Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.
E. Montogomery et al., "Reproducibility of the Diagnosis of Dysplasia in Barrett Esophagus: A Readdirmation," Apr. 2001, Human Pathology, vol. 32, No. 4, pp. 368-378.
H. Geddert et al., "Expression of Cyclin B1 in the Metaplasia—Dysplasia—Carcinoma Sequence of Barrett Esophagus," Jan. 2002, Cancer, vol. 94, No. 1, pp. 212-218.
P. Pfau et al., (2003) "Criteria for the Diagnosis of Dysplasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160nm Continuous Tuning of a MQW Laser in and External Cavity Across the Entire 1.3 μm Communications Window," Electronics Letter, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
Internatioal Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Psychophysics, download on Jun. 23, 2010 for http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Cogerence Tomogrpahy" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Interference" IEEE Journal. Selected Topics in Quantum Electronics 9 (2) 2003, pp. 294-300.
Moiseev et al., "Spectral Self-interfence Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al., "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.

(56) References Cited

OTHER PUBLICATIONS

Hess, S.T. et al. "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
Extended European Search Report mailed Dec. 14, 2010 for EP 10182301.1.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).
E. Betzig et al. "Imaging intracellular Fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).
B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Wide-field Fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy ," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647: 125 (1992).
A.A. Bednov et al., "Investigation of Statistical Properties of Lymph Flow Dynamics Using Speckle-Microscopy," SPIE, 2981: 181-90 (1997).
Feng et al., "Mesoscopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
International Search report dated Apr. 29, 2011 for PCT/US2010/051715.
International Search report dated Sep. 13, 2010 for PCT/US2010/023215.
International Search Report dated Jul. 28, 2011 for PCT/US2010/059534.
European Search Report for European Patent Application No. 1358208.2 mailed on Jul. 11, 2014.

\* cited by examiner

METHODS, ARRANGEMENTS AND APPARATUS FOR UTILIZING A WAVELENGTH-SWEPT LASER USING ANGULAR SCANNING AND DISPERSION PROCEDURES

CROSS-REFERENCE TO RELATED APPLICATION(S)

The present invention claims priority from U.S. Patent Application Ser. No. 60/896,630 filed on Mar. 23, 2007, the entire disclosure of which incorporated herein by reference.

FIELD OF THE INVENTION

The present invention relates generally to methods, arrangement and apparatus for using certain electro-magnetic radiation source, and more particularly to methods, arrangements and apparatus for wavelength tuning and a wavelength-swept laser using exemplary optical wavelength filter systems.

BACKGROUND OF THE INVENTION

Considerable effort has been devoted for developing rapidly and widely tunable wavelength laser sources for optical reflectometry, biomedical imaging, sensor interrogation, and tests and measurements. A narrow line width, wide-range and rapid tuning have been obtained by the use of an intra-cavity narrow band wavelength scanning filter. Mode-hopping-free, single-frequency operation has been demonstrated in an extended-cavity semiconductor laser by using a diffraction grating filter design. Obtaining single-frequency laser operation and ensuring mode-hop-free tuning, however, may use a complicated mechanical apparatus and limit the maximum tuning speed. One of the fastest tuning speeds demonstrated so far has been limited less than 100 nm/s. In certain applications such as biomedical imaging, multiple-longitudinal mode operation, corresponding to an instantaneous line width as large or great than 10 GHz, may be sufficient. Such width may provide a ranging depth of a few millimeters in tissues in optical coherence tomography and a micrometer-level transverse resolution in spectrally-encoded confocal microscopy.

A line width on the order of 10 GHz can be achievable with the use of an intra-cavity tuning element (such as an acousto-optic filter, Fabry-Perot filter, and galvanometer-driven diffraction grating filter). However, the sweep frequency previously demonstrated has been less than 1 kHz limited by finite tuning speeds of the filters. Higher-speed tuning with a repetition rate greater than 25 kHz may be needed for video-rate (>30 frames/s), high-resolution optical imaging in biomedical applications.

A wavelength-swept laser that uses a diffraction grating and polygon scanner has provided high-speed wavelength tuning up to 20,000 nm/ms. While the high-speed polygon based wavelength-swept light source enabled high-speed imaging as fast as 200 frames/s, wavelength tuning rate as fast as 20,000 nm/ms keeping an instantaneous line width narrower than 0.15 nm has already reached to the limit of the polygon based wavelength-swept laser. In addition, a tuning rate of 7000-nm/ms is achieved with 65 mW of power over a wavelength range of 120-nm and with an instantaneous linewidth ~0.07 nm.

Accordingly, for faster tuning and especially for wide wavelength tuning range (~200 nm) and (or) narrow instantaneous line width (~0.07 nm) at fast tuning rate, it may be beneficial to provide a further wavelength scanning filter and laser scheme/procedure and/or overcome at least some of the deficiencies described herein above.

OBJECTS AND SUMMARY OF EXEMPLARY EMBODIMENTS

One of the objectives of the present invention is to overcome certain deficiencies and shortcomings of the prior art arrangements and methods (including those described herein above), and provide exemplary embodiments of arrangements and methods for wavelength tuning and a wavelength-swept laser using exemplary optical wavelength filter systems According to one exemplary embodiment of the present invention, an apparatus and a source arrangement can be provide for light wave filtering which may facilitate high-speed wavelength-swept light with broad spectral tuning range and narrow instantaneous linewidth. In one exemplary embodiment of the present invention, the optical filter can include a diffraction grating (or multiple diffraction gratings or prisms), and an angular scanning element(s) (including, but not limited to, a polygonal mirror, a (multi facets) planar mirror disposed on a rotating shaft, a (multi facets) mirror disposed on a galvonmeter, or an (multi) acousto-optic modulator(s)). An exemplary alignment of the diffraction grating (or multiple diffraction gratings) can facilitate a high-speed wavelength sweeping over a broad tuning range (~120 nm) with narrow instantaneous linewidth (~0.07 nm).

In another exemplary embodiment, the wavelength-swept filter can be combined with a gain medium implementing a wavelength tunable light source. The filter and gain medium may further be incorporated into a laser cavity. For example, a laser can emit a narrow band spectrum with its center wavelength being rapidly swept over a broad wavelength range. The laser resonator may include a unidirectional fiber-optic ring, unidirectional combined fiber and free space optic ring, or a full free space linear cavity with a specially designed semiconductor optical gain medium to minimize the cavity length of the laser.

Indeed, exemplary systems and methods for filtering an electromagnetic radiation can be provided. For example, at least one first arrangement can be provided which is capable of receiving at least one first electro-magnetic radiation and forwarding at least one second electro-magnetic radiation at different angles with respect to a direction of incidence of the first electro-magnetic radiation. At least one second wavelength dispersion arrangement can be provided which is configured to receive the second electro-magnetic radiation, forward at least one third electro-magnetic radiation to the first arrangement and further receive at least one fourth electro-magnetic radiation. The third electro-magnetic radiation can be based on the second electro-magnetic radiation, and the fourth electro-magnetic radiation can be based on the third electro-magnetic radiation.

For example, the first arrangement can be a multi-faceted mirror arrangement. The first electro-magnetic radiation can impact a first facet of the multi-faceted mirror arrangement, and the third electro-magnetic radiation can impact a second facet of the multi-faceted mirror arrangement, with the first and second facets being different from one another. The first arrangement can also be a polygon beam scanning arrangement. T first electro-magnetic radiation can impacts a first facet of the polygon beam scanning arrangement, and the third electro-magnetic radiation can impact a second facet of the polygon beam scanning arrangement, with the first and second facets being different from one another. The polygon beam scanning arrangement is capable of continuously being rotated.

According to another exemplary embodiment of the present invention, the second arrangement can be a defraction grating arrangement, a prism arrangement and/or a grism arrangement. The first and second arrangements may be positioned such that a particular electro-magnetic radiation that is based on the first electro-magnetic radiation may be received by the at least one first arrangement from the second arrangement more that twice. At least one third wavelength dispersion arrangement can be provided which is configured to physically separate one or more components of a particular electro-magnetic radiation based on a frequency of the particular electro-magnetic radiation. The first electro-magnetic radiation can be based on the particular electro-magnetic radiation. In addition, at least one fourth arrangement can be provided which is configured to receive at least some of the one or more components, and modify at least one characteristic of the received one or more components to provide the first electro-magnetic radiation which is associated with one or more further components of the particular electro-magnetic radiation.

Yet another exemplary embodiment of the present invention can be provided. For example, a source arrangement can provide at least one particular electromagnetic radiation. Such exemplary source arrangement can include at least one emitter arrangement configured to provide the at least one electromagnetic radiation. At least one first arrangement may be provided which is capable of receiving the particular electro-magnetic radiation and forwarding at least one first electro-magnetic radiation at different angles with respect to a direction of incidence of the particular electro-magnetic radiation. Further, at least one second wavelength dispersion arrangement can be provided which is configured to receive the at least one first electro-magnetic radiation, forward at least one second electro-magnetic radiation to the first arrangement and further receive at least one third electro-magnetic radiation. The second electro-magnetic radiation can be based on the first electro-magnetic radiation, and the third electro-magnetic radiation can be based on the at least one second electro-magnetic radiation.

The source arrangement can also include at least one laser cavity configured to receive the third electromagnetic radiation. The laser cavity can be a ring laser cavity. The emitter arrangement can be a semiconductor optical amplifier, a laser diode, a super-luminescent diode, a doped optical fiber, a doped laser crystal, a doped laser glass, and/or a laser dye. The particular electromagnetic radiation may have a frequency that is continuously swept in a positive wavelength direction. An optical circulator can also be included in the source arrangement. For example, wavelength ranges of the emitter arrangement can be distinct from one another. The first arrangement can be a multi-faceted mirror arrangement. The particular electro-magnetic radiation can impact a first facet of the multi-faceted mirror arrangement, and the second electro-magnetic radiation can impact a second facet of the multi-faceted mirror arrangement, with the first and second facets being different from one another.

According to still another exemplary embodiment of the present invention, the first arrangement can be a polygon beam scanning arrangement. The particular electro-magnetic radiation can impact a first facet of the polygon beam scanning arrangement, and the second electro-magnetic radiation can impact a second facet of the polygon beam scanning arrangement, with the first and second facets being different from one another. The polygon beam scanning arrangement is capable of continuously being rotated. The second arrangement can be a defraction grating arrangement, a prism arrangement and/or a grism arrangement. The first and second arrangements can be positioned such that a further electro-magnetic radiation that is based on the first electro-magnetic radiation is received by the first arrangement from the second arrangement more that twice.

At least one third wavelength dispersion arrangement can also be provided which is configured to physically separate one or more components of a further electro-magnetic radiation based on a frequency of the particular electro-magnetic radiation. The particular electro-magnetic radiation may be based on the further electro-magnetic radiation. At least one fourth arrangement can also be provided which is configured to receive at least some of the one or more components, and modify at least one characteristic of the received one or more components to provide at least one particular electro-magnetic radiation which is associated with one or more further components of the further electro-magnetic radiation.

In yet another exemplary embodiment of the present invention, an apparatus and source arrangement for filtering an electromagnetic radiation can be provided which may include at least one spectral separating arrangement configured to physically separate one or more components of the electro-magnetic radiation based on a frequency of the electromagnetic radiation. The apparatus and source arrangement may also have at least one continuously rotating optical arrangement, e.g., polygonal scanning mirror and spinning reflector disk scanner, which is configured to receive at least one signal that is associated with the one or more components. Further, the apparatus and source arrangement can include at least one beam selecting arrangement configured to receive the signal.

Other features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which.

Figure 1:
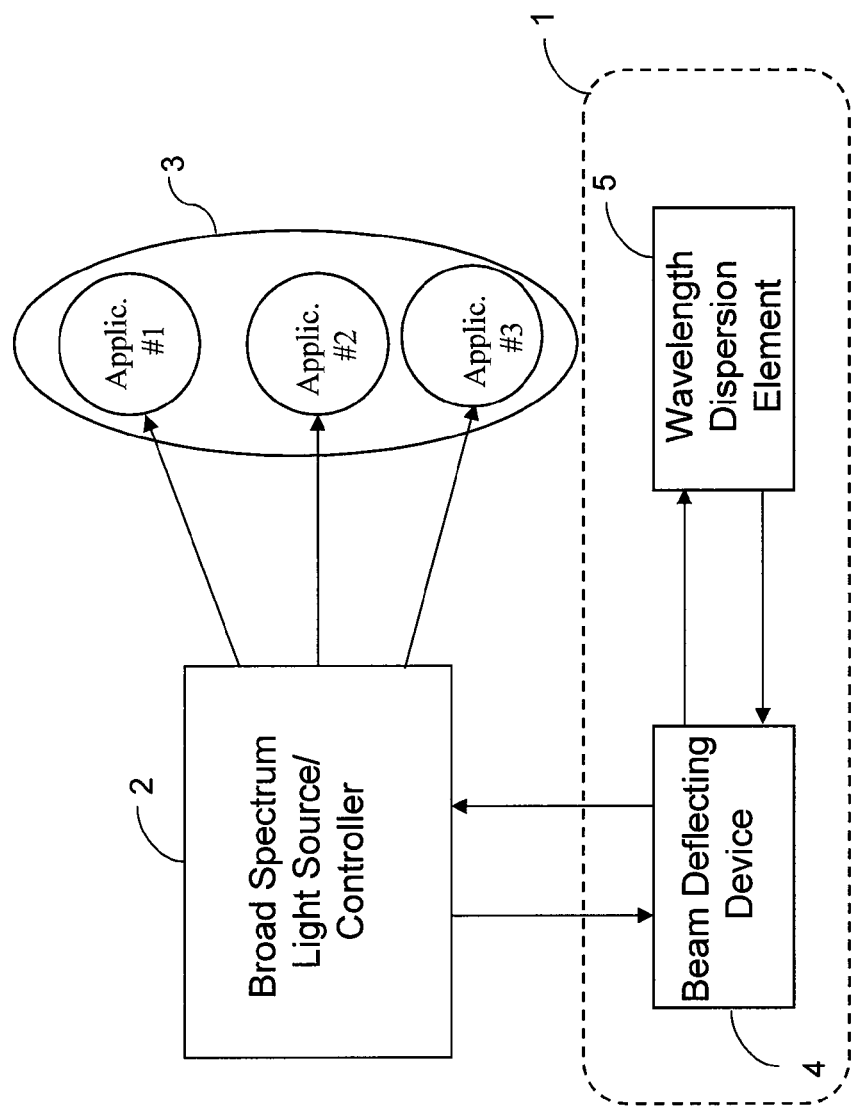
FIG. 1 is a block diagram of a first exemplary embodiment of an optical wavelength filter arrangement/apparatus according to the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

FIG. 1 shows a block diagram of a first exemplary embodiment of an arrangement/apparatus which includes an optical wavelength filter 1 in accordance the present invention. In this first exemplary embodiment, the optical wavelength filter 1 can be used in a variety of different applications, general and non-limiting examples of which are described below. In the example shown in FIG. 1, the filter 1 may be coupled to one or more applications 3 via a light source 2. It should be understood that in certain exemplary applications, the filter 1 can be used with or connected to an application (e.g., one or more of the applications 3) via a device other than a light source (e.g. a passive or active optical element).

In the first exemplary embodiment shown in FIG. 1, a broad spectrum light source and/or controller 2 (hereinafter referred to as "light controller"), may illuminate a beam deflecting device 4 and then be coupled to a wavelength dispersing element 5. The wavelength dispersing element 5 may be coupled to several configurations which shall be described in further detail below in connection with FIGS. 8A-8D, and then retrace the path back to the light controller 2. The light controller 2 can be further coupled to one or more of the applications 3 that are adapted to perform one or more tasks with or for, including but not limited to, optical imaging processes and optical imaging systems, laser machining processes and systems, photolithography and photolithographic systems, laser topography systems, telecommunications processes and systems, etc. The light controller 2 can be one or more of various systems and/or arrangements that are configured to transmit a beam of light having a broad frequency (f) spectrum.

In one exemplary embodiment of the present invention, the beam of light may be a collimated beam of light. The beam of light can include a plurality of wavelengths $\lambda \ldots \lambda n$, within the visible light spectrum (e.g., red, blue, green). Similarly, the beam of light provided by the light controller 2 can also include a plurality of wavelengths $\lambda \ldots \lambda n$ that may be defined outside of the visible spectrum (e.g., ultraviolet, near infrared or infrared). According to another exemplary embodiment of the present invention, the light controller 2 can include a unidirectional light transmission ring, which shall be described in further detail below in connection with FIGS. 8A-8D which shows an exemplary embodiment of a wavelength tuning laser source.

Further, in still another exemplary embodiment of the present invention, the light controller 2 can include a linear resonator system, which shall be described in further detail below in connection with FIGS. 8A-D. In one exemplary embodiment of the present invention, the wavelength dispersing element 5 can include a light dispersion element, which may include but not limited to, a reflection grating, a diffraction grating, prism, or combinations of one or more of these elements. Furthermore, the dispersion element 5 is adapted to direct or steer and/or focus the wavelengths of light to a predetermined position(s) located on a beam deflecting device 4. Moreover, the dispersion element 5 can be controlled to receive and selectively redirect one or more discrete wavelengths of light back to the beam deflecting device and back to the light controller 2. Thereafter, the light controller 2 can selectively direct the received discrete wavelengths of light to any one or more of the applications. The device 4 can be provided in many different ways. For example, the beam deflecting device 4 can be provided from elements including, but not limited to, a polygonal mirror (or several polygon mirrors), a (multi facets) planar mirror disposed on a rotating shaft, a (multi facets) mirror disposed on a galvanometer, or an (multi) acousto-optic modulator(s).

Figure 2A:
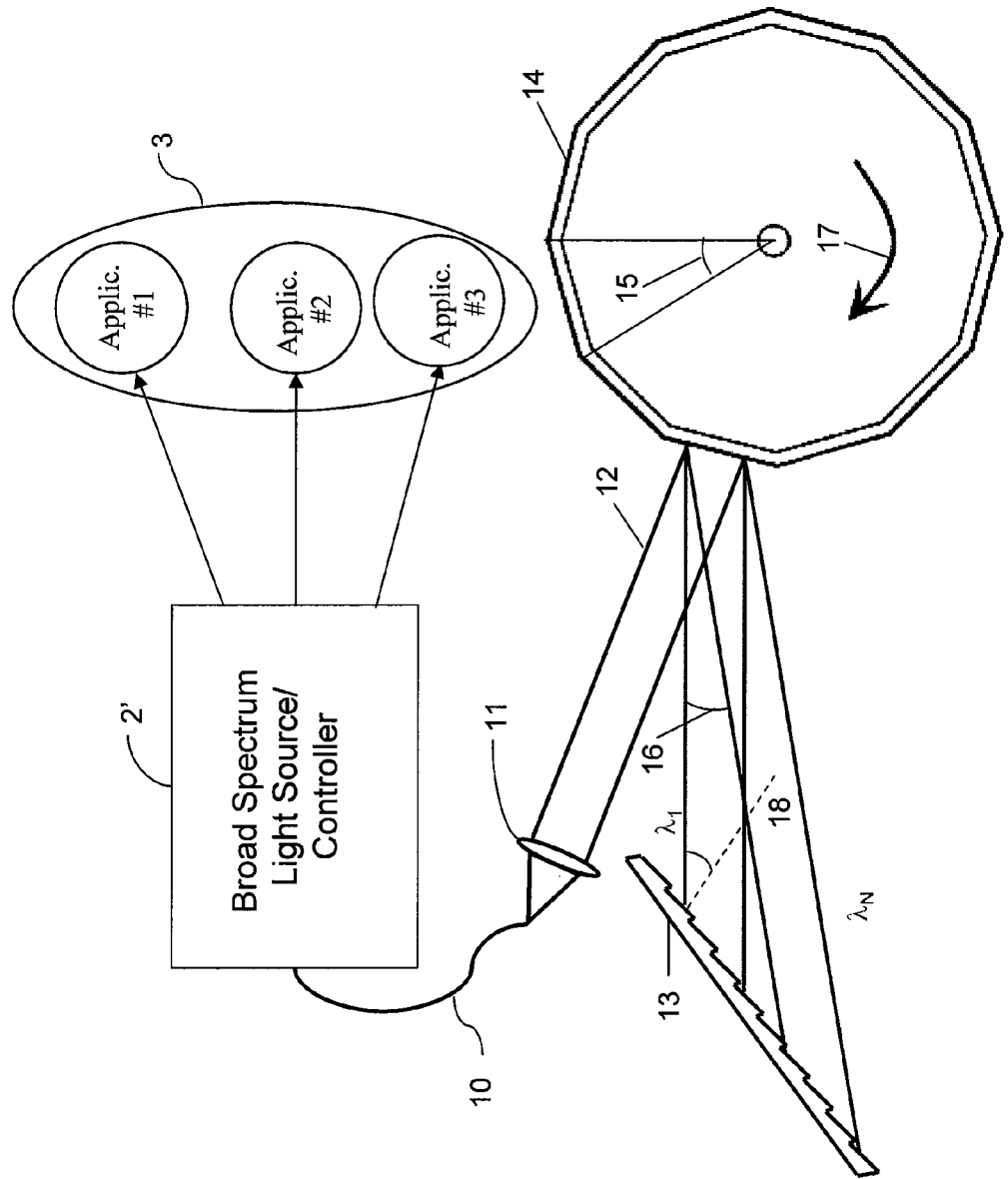
FIG. 2A is an illustration of a second exemplary embodiment of the arrangement/apparatus which includes a diffraction grating and polygon scanner-based wavelength tuning filter according to the present invention.

FIG. 2A shows a diagram of an exemplary embodiment of the arrangement/apparatus which includes the diffraction grating and polygon scanner based wavelength tuning filter in accordance with the present invention. The exemplary optical wavelength filter 1' can be configured as a reflection-type filter which may have substantially identical input and output ports. An input/output optical fiber 10 and a collimating lens 11 can provide an input from a light controller 2' (which may be substantially similar to the light controller 2 described above with reference to FIG. 1) to the optical wavelength filter 1'. The optical wavelength filter can include a collimated input/output beam 12, a diffraction grating 13, and a spinning polygon scanner 14. Light input to the optical wavelength filter is provided as a collimated input beam 12. Wavelength filtered output is retro-reflected as a collimated light output 12. The mirror surface of the polygon arrangement 14 is placed such that the beam of light is reflected with a non-zero angle (rather than directly being reflected back to the light controller 2' from the polygon arrangement's mirror facet 14). To have minimum beam clipping on the polygon facet, the following condition can be met, e.g.:

$$D < L \cos(\psi)$$

where D, L, and ψ are $$\frac{1}{e^2}$$

width of the collimated beam 12 of each wavelength components at the focusing lens 11, facet size, and incident angle, respectively. The sweep angle of the reflected light from the polygon arrangement 14 is double the polygon arrangement's 14 rotation angle 16. The diffraction grating 13 is placed close to the polygon scanner facet (≤2 cm) to decrease beam displacement on the diffraction grating 13. When each partial rotation of the polygon through an angle of $$\theta = \frac{2\pi}{N}$$

(e.g., the facet-to-facet angle 15 of the polygon), where N is the number of mirror facets, the sweep angle 16 of the reflected light is 2θ for a rotation of the angle θ of the polygon arrangement 14. The reflected light from the polygon scanner facet 14 illuminates the diffraction grating 13 at Littrow's angle before retracing the path back to the light controller 2.

As is illustrated in the exemplary embodiment shown in FIG. 2A, a beam deflection device 4 (e.g., which may include a polygon mirror or arrangement 14) is adapted to preferably reflect back only the spectral component within a narrow passband as a function Littrow's angle. The orientation of the incident beam 12 with respect to the normal axis of the polygon facet 14 and a rotation direction 17 of the polygon arrangement 14 can be used to determine the direction of wavelength tuning, e.g., a wavelength up (positive) scan or a wavelength down (negative) scan. The exemplary arrangement shown in FIG. 2A can generate a negative wavelength sweep. It should be understood that although the polygon arrangement 14 is shown in FIG. 2A as having twelve facets, polygon arrangements which have fewer than twelve facets or greater than twelve facets can also be used. While generally not considering practical mechanical limits, based upon conventional manufacturing techniques, a particular number of facets of the polygon arrangement 14 to use in any application may depend on a desired scanning rate and a scanning range for a particular application.

Furthermore, the size of the exemplary polygon arrangement 14 may be selected based on preferences of a particular application, and preferably taking into account certain factors including, but not limited to, manufacturability and weight of the polygon arrangement 14. It should also be understood the diffraction gratings that have different pitch may be provided. In addition, the diffraction grating may provide adjustable parameters which control the tuning range and linewidth. The Gaussian beam 12 can be utilized with a broad optical spectrum incident to the grating from the fiber collimator 11. The exemplary grating equation is expressed as λ=2p sin(α) where λ is the optical wavelength, p is the grating pitch, and α is Littrow angle (or the incident angle (the diffracted angle) of the beam with respect to the normal axis 18 of the grating). FWHM bandwidth of the filter is defined by $$(\delta\lambda)_{FWHM} = \frac{2\sqrt{2\ln(2)}\,\lambda pm\cos(\alpha)}{\pi D},$$

where m is the diffraction order and D is $$\frac{1}{e^2}$$

width of the Gaussian beam at the fiber collimator for double pass.

The filter tuning range can be expressed as Δλ=2pΔα cos (α₀), where α₀ is the Littrow's angle at λ₀ (center wavelength). One of exemplary design parameters of the filter, originated from the multiple facet nature of the polygon mirror, is the free spectral range, which is described in the following. The polygon arrangement 14 may have a facet-to-facet polar angle given by θ=2π/N≈L/R, where L is the facet width, R is the radius of the polygon and the sweep angle 16 of the reflected light is 2θ for a rotation of the angle θ of the polygon arrangement 14. The exemplary polygon arrangement 14 preferably does not retro-reflect more than one spectral component at a given time because the range of Littrow angle is equal to the sweeping angle, i.e. Δα=2θ. The spacing of the multiple spectral components simultaneously reflected, or the free spectral range, can be defined as (Δλ)$_{FSR}$=4pθ cos(α₀).

In an exemplary intra-cavity scanning filter application, the free spectral range of the filter can exceed the spectral range of the gain medium in order to avoid multiple frequency bands (in the case of an inhomogeneously broadened gain medium) or limited tuning range (in the case of a homogeneously broadened gain medium).

The duty cycle of laser tuning by the filter can be, for example, 100% with no excess loss caused by beam clipping if preferable condition ca be met as follows:

$$D < L\cos(\psi) \quad (1)$$

This exemplary equation may be derived from a condition that the beam illuminating polygon facet should be smaller than the facet width at the maximum incident angle of the beam with respect to the normal axis 18 of the polygon facet.

Figure 2B:
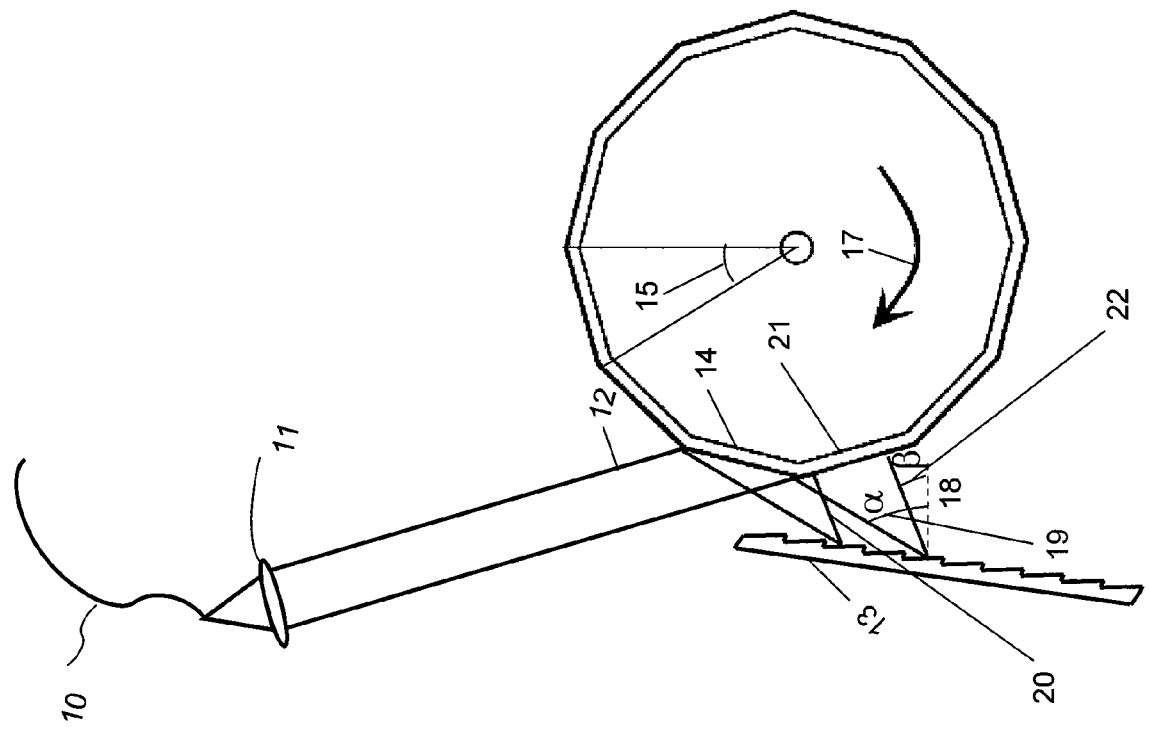
FIG. 2B is an illustration of a third exemplary embodiment of the arrangement/apparatus which includes the diffraction grating and polygon scanner based wavelength tuning filter according to the present invention.

FIG. 2B shows a diagram of a third exemplary embodiment of the arrangement/apparatus which includes the wavelength tunable filter arrangement 1 for decreasing FWHM bandwidth of the filter with the same polygon rotation speed according to the present invention. In this exemplary embodiment, the reflected light from the polygon scanner facet 14 illuminates the diffraction grating 13 at an angle α 19 (not equal to Littrow's angle). The diffracted light 20 at angle β22 from the grating illuminates another polygon facet 21 (which are not necessary the adjacent faces of the polygon facet 14) before retracing the path back to the light controller 2.

The diffraction grating according to the third exemplary embodiment of the present invention is operative to provide one or more features as described above, as well as to convert a diverging beam from the polygon facet 14 into converging angular dispersion after the diffraction grating 13 on the polygon facet 21. Such result may be advantageous for a proper operation of the filter. In addition, the diffraction grating 13 and the incident angle of the optical beam 12 on the polygon facet 14 may provide adjustable parameters, which control the tuning range and linewidth. In this exemplary embodiment, The grating equation can be expressed as $\lambda = p(\sin(\alpha) + \sin(\beta))$ where $\lambda$ is the optical wavelength, p is the grating pitch, and $\alpha$ and $\beta$ are the incident and diffracted angles of the beam with respect to the normal axis 18 of the diffraction grating 13, respectively. From simple geometry, one can find that $\phi = \beta$, where $\phi$ is the angle between the second polygon facet 21 and the diffraction grating. FWHM bandwidth of the filter is defined by $$(\delta\lambda)_{FWHM} = \frac{2\sqrt{\ln(2)}\,\lambda pm\cos(\alpha)}{\pi D}.$$

The filter tuning range can be expressed as $\Delta\lambda = p(\Delta\alpha \cos(\alpha_0) + \Delta\beta \cos(\beta_0))$ where $\alpha_0$ and $\beta_0$ are the incident and diffracted angles at $\lambda_0$ (center wavelength). If the sweeping angle is equal to the range of the incident angle, i.e. $\Delta\alpha = 2\theta$ and the range of diffracted spectrum is equal to the facet angle, i.e. $\Delta\beta = \theta$, the polygon arrangement can retro-reflect one spectral component at a given time. The spacing of the multiple spectral components simultaneously reflected, or the free spectral range, can be defined as $\Delta\lambda = p\theta(2\cos(\alpha_0) + \cos(\beta_0))$.

The duty cycle of laser tuning by the filter can be, for example, 100% with no excess loss caused by beam clipping if preferable conditions are met as follows:

$$D < L\cos(\psi) \quad (2)$$

$$D < L\frac{\cos(\alpha)}{\cos(\beta)} \quad (3)$$

The first equation may be derived from a condition that the beam width illuminating the first polygon facet 14 should be smaller than the facet width. The second equation can be derived from that the diffracted beam width illuminating the second polygon facet 21 should be smaller than the facet width.

Figure 2C:
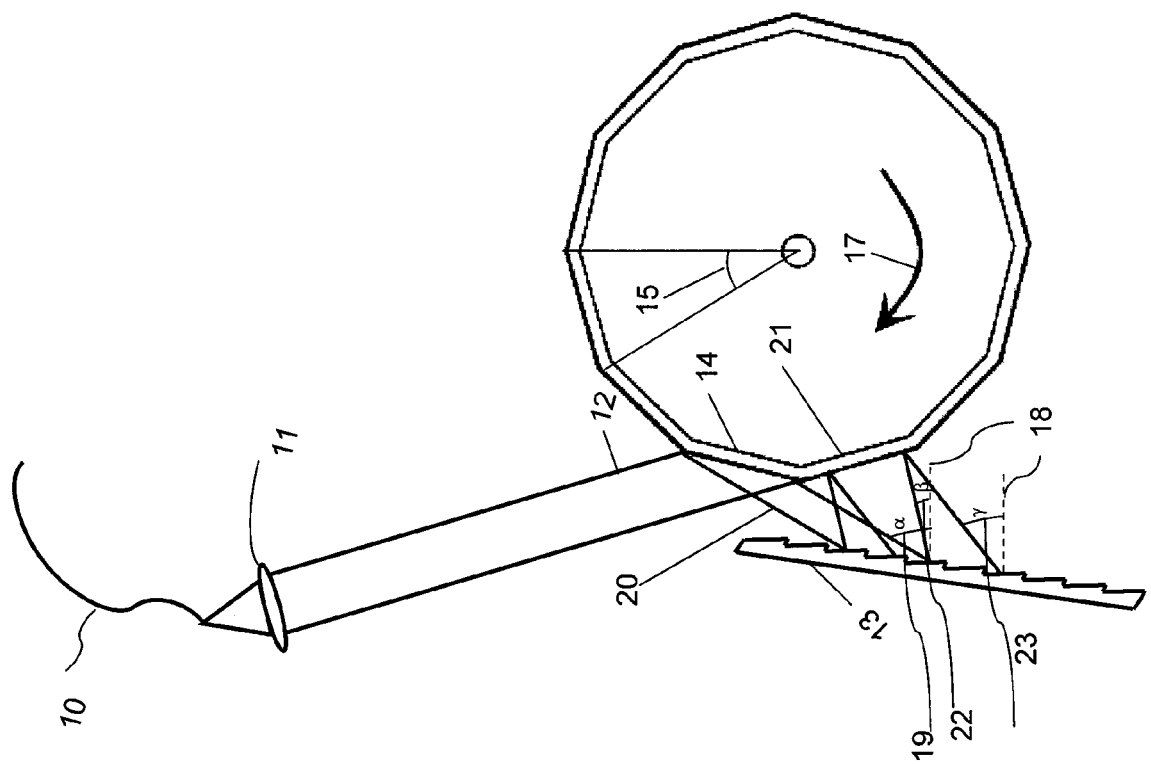
FIG. 2C is an illustration of a fourth exemplary embodiment of the arrangement/apparatus which includes the diffraction grating and polygon scanner according to the present invention.

FIG. 2C shows a diagram of a forth exemplary embodiment of the wavelength tunable filter arrangement 1 for decreasing FWHM bandwidth of the filter with the same polygon rotation speed according to the present invention. In this exemplary embodiment, the reflected light from the polygon scanner facet 14 illuminates the diffraction grating 13 at an angle α19 (not equal to Littrow's angle). The diffracted light 20 at angle β22 from the grating illuminates another polygon facet 21 (preferably the adjacent faces of the polygon facet 14), and can be returned to the grating at Littrow's angle γ23 before retracing the path back to the light controller 2.

The diffraction grating 13 according to the forth exemplary embodiment of the present invention as shown in FIG. 2B is operative to provide one or more features as described above, as well as to convert a diverging beam from the polygon facets 14 and 21 into converging angular dispersion after the diffraction grating 13 on the polygon facet 21. Such result may be advantageous for a proper operation of the filter. In addition, the diffraction grating 13 and the incident angle of the optical beam 12 on the polygon facet 14 may provide adjustable parameters, which control the tuning range and linewidth. In this embodiment, The grating equations can be expressed as $\lambda = p(\sin(\alpha) + \sin(\beta))$ and $\lambda = 2p\sin(\gamma)$, where $\lambda$ is the optical wavelength, p is the grating pitch, and $\alpha$, $\beta$, $\gamma$ are the incident, diffracted, and Littrow angles of the beam with respect to the normal axis 18 of the diffraction grating 13, respectively. From simple geometry, one can find that $2\phi = \gamma \pm \beta$, where $\phi$ is the angle between the second polygon facet 21 and the diffraction grating 13. By eliminating $\beta$ and $\gamma$, the above equations give an expression, quadratic in $\lambda$, that depends only on the incident angle 19 and the angle between the second polygon facet 21 and the diffraction grating 13. The solution is $$\lambda = \frac{p\left\{\sin(\alpha)(1 + 0.5\cos(2\phi)) + \sqrt{\sin^2(\alpha)(1 + 0.5\cos(2\phi))^2 - (\sin^2(\alpha) - \sin^2(2\phi))(1.25 + \cos(2\phi))}\right\}}{(1.25 + \cos(2\phi))} \quad (4)$$

As shown in the equation, the tuning range of the filter is fundamentally limited by the grating pitch, the incident angle 19, and the angle between the second polygon facet and the diffraction grating 13. In addition, it can be shown that the FWHM bandwidth of the filter (instantaneous line-width) is given by $$\delta\lambda = \frac{2p\lambda\sqrt{\ln(2)}\cos(\alpha)}{\pi D\left(1 \pm \frac{0.5\cos(\beta)}{\cos(\gamma)}\right)} \quad (5)$$

Equation (5) shows that the linewidth of this embodiment can be improved by a factor of $$1 + \frac{0.5\cos(\beta)}{\cos(\gamma)}$$

compared to the previous embodiment.

The filter tuning range can be expressed as $\Delta\lambda=p(\Delta\alpha \cos(\alpha_0)+\Delta\beta \cos(\beta_0))$, and $\Delta\lambda=2p\Delta\gamma \cos(\gamma_0)$ where $\alpha_0$, $\beta_0$, and $\gamma_0$ are the incident, diffracted, and Littrow angles at $\lambda_0$ (center wavelength). If the sweeping angle is equal to the range of the incident angle, i.e. $\Delta\alpha=2\theta$ and the range of diffracted spectrum follows the following equality, i.e. $2\theta=\Delta\gamma\pm\Delta\beta$, the polygon arrangement can retro-reflect one spectral component at a given time. The spacing of the multiple spectral components simultaneously reflected, or the free spectral range, can be defined as $$\Delta\lambda = 2\theta p_1 \frac{(\cos\alpha_0 + \cos\beta_0)}{1 \pm \frac{p_1 \cos(\beta_0)}{2p_2 \cos(\gamma_0)}}.$$

The duty cycle of laser tuning by the filter can be, for example, 100% with no excess loss caused by beam clipping if preferable conditions are met as follows:

$$D < L\cos(\psi) \tag{6}$$

$$D < L\frac{\cos(\alpha)}{\cos(\beta)} \tag{7}$$

Equation (6) may be derived from a condition that the beam width illuminating the first polygon facet 14 should be smaller than the facet width. Equation (7) can be derived from that the diffracted beam width illuminating the second polygon facet 21 should be smaller than the facet width.

Figure 2D:
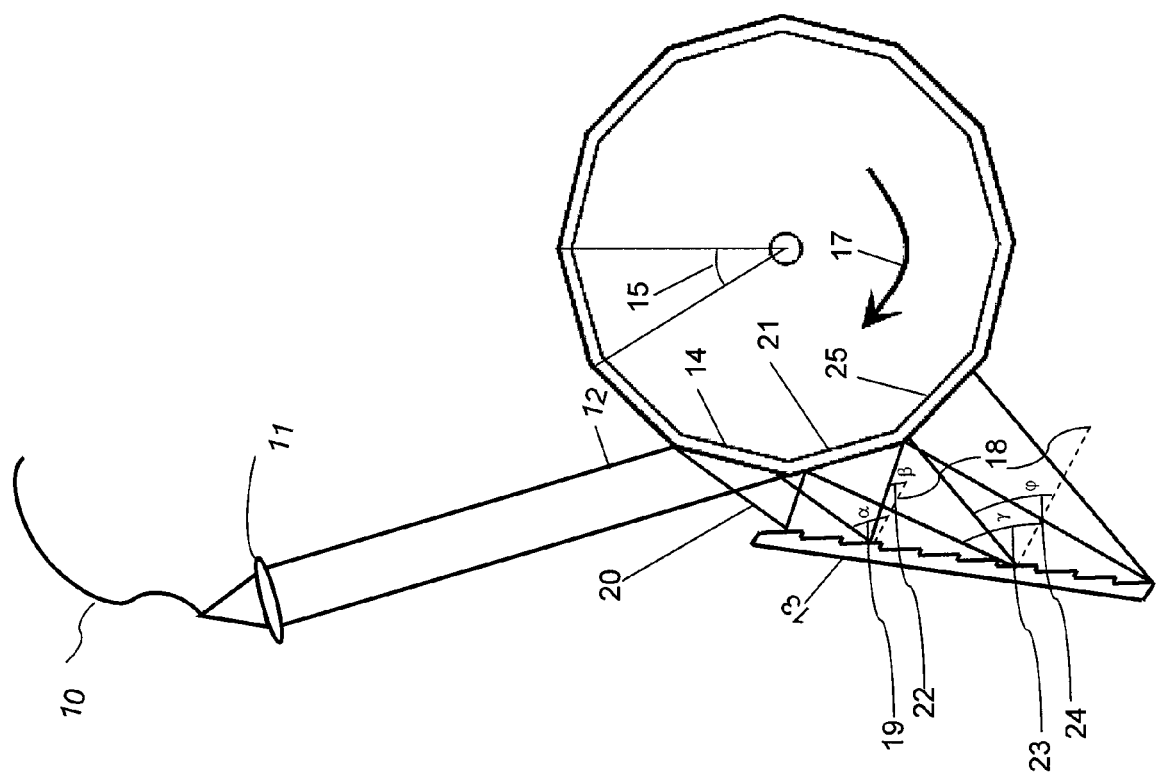
FIG. 2D is an illustration of a fifth exemplary embodiment of the arrangement/apparatus which includes the diffraction grating and polygon scanner according to the present invention.

FIG. 2D shows a diagram of a fifth exemplary embodiment of the arrangement/apparatus which includes the wavelength tunable filter arrangement 1 for decreasing FWHM bandwidth of the filter with the same polygon rotation speed according to the present invention. In this exemplary embodiment, the reflected light from the polygon scanner facet 14 illuminates the diffraction grating 13 at an angle α19 (e.g., may be different from Littrow's angle). The diffracted light 20 at angle β22 from the grating illuminates another polygon facet 21 (not necessary the adjacent faces of the polygon facet 14) and is returned to the grating at an angle γ23 (e.g., may be different from Littrow's angle) and diffracted light at angle ϕ24 illuminates the third polygon facet 25 (not necessary the adjacent faces of the polygon facet 14 and 21) before retracing the path back to the light controller 2.

The diffraction grating according to the fifth exemplary embodiment of the present invention can be operative to provide one or more features as described above, as well as to convert a diverging beam from the polygon facets 14 and 21 into converging angular dispersion after the diffraction grating 13 on the polygon facet 21. Such result may be advantageous for a proper operation of the filter. In addition, the diffraction grating 13 and the incident angle of the optical beam 12 on the polygon facet 14 may provide adjustable parameters, which control the tuning range and linewidth. In this embodiment, The grating equations are expressed as $\lambda=p(\sin(\alpha)+\sin(\beta))$ and $\lambda=p(\sin(\gamma)+\sin(\phi))$, where $\lambda$ is the optical wavelength, p is the grating pitch, and $\alpha$, $\beta$, $\gamma\phi$ are the incident and diffracted angles of the beam with respect to the normal axis 18 of the diffraction grating 13, respectively.

It is possible that $2\phi_1=\gamma+\beta$, where $\phi_1$ is the angle between the second polygon facet 24 and diffraction grating 13. In addition, $\phi_2=\phi$, where $\phi_2$ is the angle between the third polygon facet 25 and diffraction grating 13. By eliminating $\beta$, $\gamma$, and $\phi$, the above equations give an expression, quadratic in $\lambda$, that depends only on the incident angle and the angle between the second polygon and third polygon facets 21 and 25 and diffraction grating 13. The exemplary solution can be as follows:

$$\lambda = \frac{p\left\{\begin{array}{l}\sin(\alpha)(1+0.5\cos(2\phi)) + \\ \sqrt{\sin^2(\alpha)(1+0.5\cos(2\phi))^2 - } \\ (\sin^2(\alpha) - \sin^2(2\phi))(1.25 + \cos(2\phi))\end{array}\right\}}{(1.25 + \cos(2\phi))}$$

As shown in this equation, the tuning range of the filter is fundamentally limited by the grating pitch, the incident angle 19, and the angle between the second polygon facet and the diffraction grating 13. In addition, it can be shown that the FWHM bandwidth of the filter (instantaneous line-width) is given by $$\delta\lambda = \frac{2p\lambda\sqrt{\ln(2)}\cos(\alpha)}{\pi D\left(1 + \frac{\cos(\beta)}{\cos(\gamma)}\right)} \tag{8}$$

Equation (8) shows that the linewidth of this embodiment has been improved by a factor of $$1 + \frac{\cos(\beta)}{\cos(\gamma)}$$

compared to the previous embodiment.

The filter tuning range can be expressed as $\Delta\lambda=p(\Delta\alpha \cos(\alpha_0)+\Delta\beta \cos(\beta_0))$ and $\Delta\lambda=p(\Delta\gamma \cos(\gamma_0)+\Delta\phi \cos(\phi_0))$ where $\alpha_0$, $\beta_0$, $\gamma_0$, and $\phi_0$ are the incident, and diffracted angles at $\lambda_0$ (center wavelength). If the sweeping angle is equal to the range of the incident angle, i.e. $\Delta\alpha=2\theta$ and the range of the first diffracted spectrum follows the following equality, i.e. $2\theta=\Delta\gamma+\Delta\beta$, and the range of the second diffracted spectrum is equal to the facet angle, i.e. $\Delta\phi=\theta$, the polygon arrangement can retro-reflect one spectral component at a given time. The spacing of the multiple spectral components simultaneously reflected, or the free spectral range, can be defined as $$\Delta\lambda = \frac{p\theta\left(\begin{array}{c}\cos(\varphi_0)\cos(\beta_0) + 2\cos(\gamma_0)\cos(\beta_0) + \\ 2\cos(\gamma_0)\cos(\alpha_0)\end{array}\right)}{(\cos(\gamma_0) + \cos(\beta_0))}. \tag{9}$$

The duty cycle of laser tuning by the filter can be, for example, 100% with no excess loss caused by beam clipping if preferable conditions can be met as follows:

$$D < L\cos(\psi) \tag{10}$$

$$D < L\frac{\cos(\alpha)}{\cos(\beta)} \tag{11}$$

$$D < L\frac{\cos(\gamma)}{\cos(\varphi)} \tag{12}$$

Equation (10) may be derived from a condition that the beam width illuminating the first polygon facet 14 should be smaller than the facet width. Equations (12) and (12) can be derived from that the diffracted beam widths illuminating the second and third polygon facets 21 and 25 should be smaller than the facet width. The FWHM bandwidth of the filter can be further decreased by illuminating several diffraction gratings with the same or different pitches.

Figure 3A:
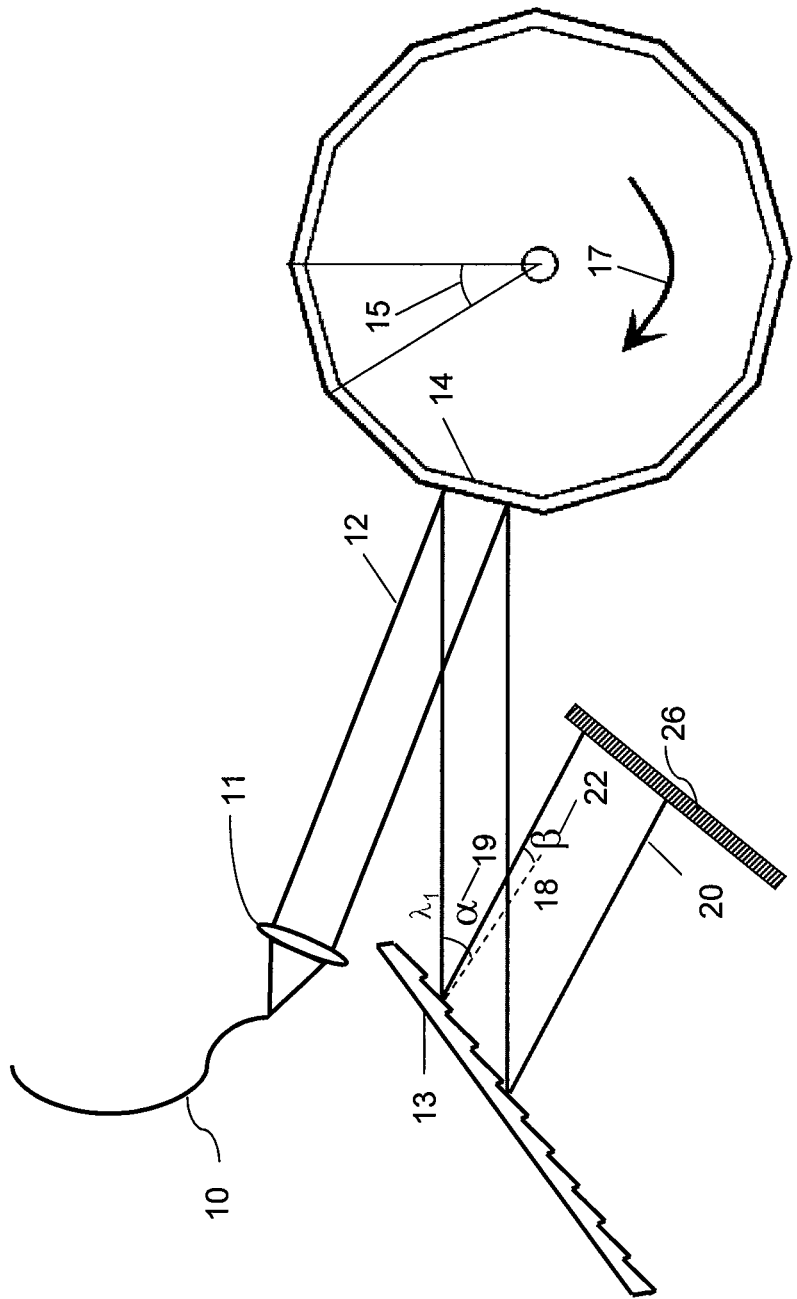
FIG. 3A is an illustration of a sixth exemplary embodiment of the arrangement/apparatus which includes the diffraction grating, a polygon scanner, and a reflector according to the present invention.

FIG. 3A shows a diagram of a sixth exemplary embodiment of the arrangement/apparatus which includes the wavelength tunable filter arrangement 1 with the same polygon rotation speed according to the present invention. In this exemplary embodiment, the reflected light from the polygon scanner facet 14 illuminates the diffraction grating 13 (with grating pitch $p_1$) at an angle $\alpha$ 19 (not equal to Littrow's angle). The diffracted light 20 at angle $\beta$22 from the grating illuminates a reflector 26 before retracing the path back to the light controller 2. It can be shown that the FWHM bandwidth of this filter (instantaneous line-widths) is given by $$\delta\lambda = \frac{2p\lambda\sqrt{\ln(2)}\cos(\alpha)}{\pi D}.$$

Figure 3B:
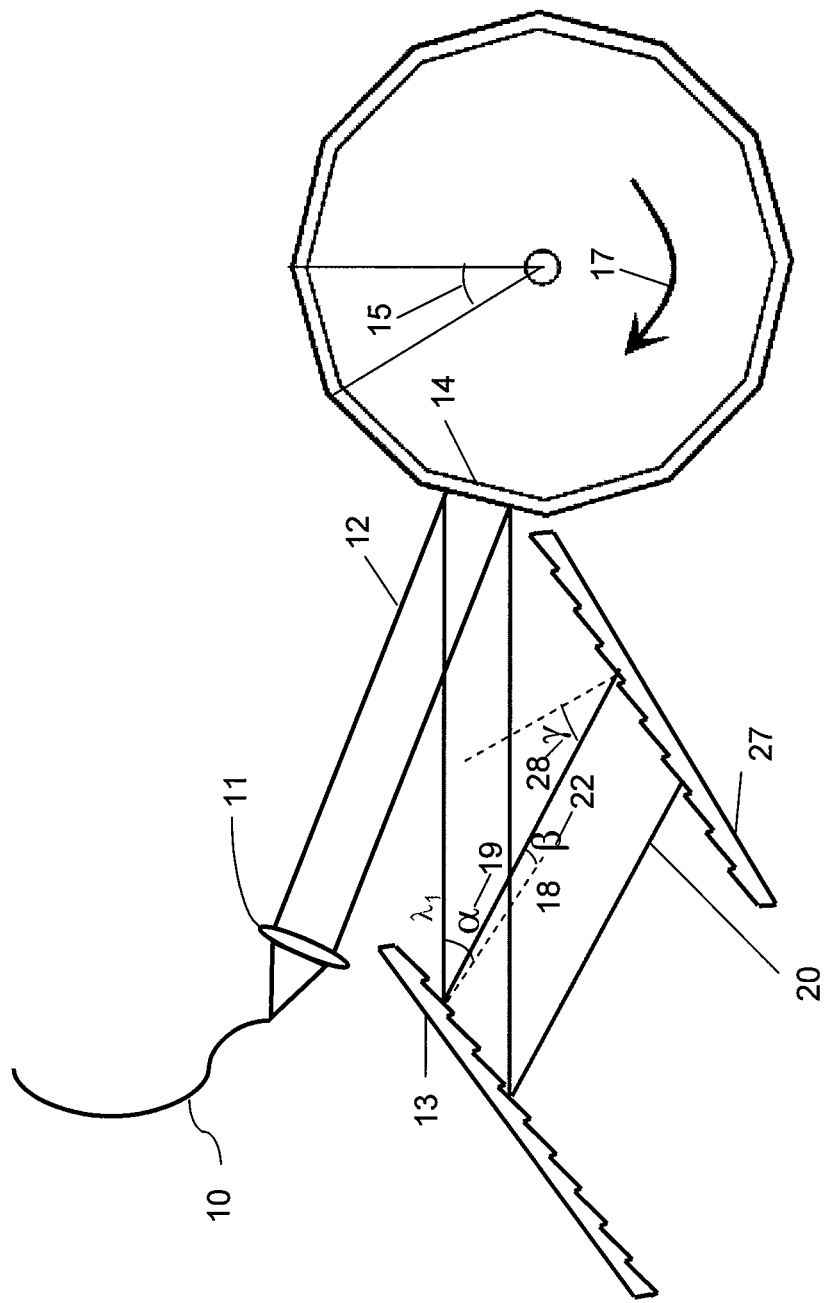
FIG. 3B is an illustration of a seventh exemplary embodiment of the arrangement/apparatus which includes two diffraction gratings and polygon scanner according to the present invention.

FIG. 3B shows a diagram of a seventh exemplary embodiment of the arrangement/apparatus which includes the wavelength tunable filter arrangement 1 with the same polygon rotation speed according to the present invention. In this exemplary embodiment, the reflected light from the polygon scanner facet 14 illuminates the diffraction grating 13 (with grating pitch $p_1$) at an angle $\alpha$19 (not equal to Littrow's angle). The diffracted light 20 at angle $\beta$22 from the grating illuminates other diffraction grating 27 (with grating pitch $p_2$) at Littrow's angle $\gamma$28 before retracing the path back to the light controller 2. It can be shown that the FWHM bandwidth of this filter (instantaneous line-widths) is given by $$\delta\lambda = \frac{2p_1 p_2 \lambda \sqrt{\ln(2)} \cos(\alpha)}{\pi D\left(p_2 + \frac{\cos(\beta)}{2\cos(\gamma)} p_1\right)}.$$

Figure 3C:
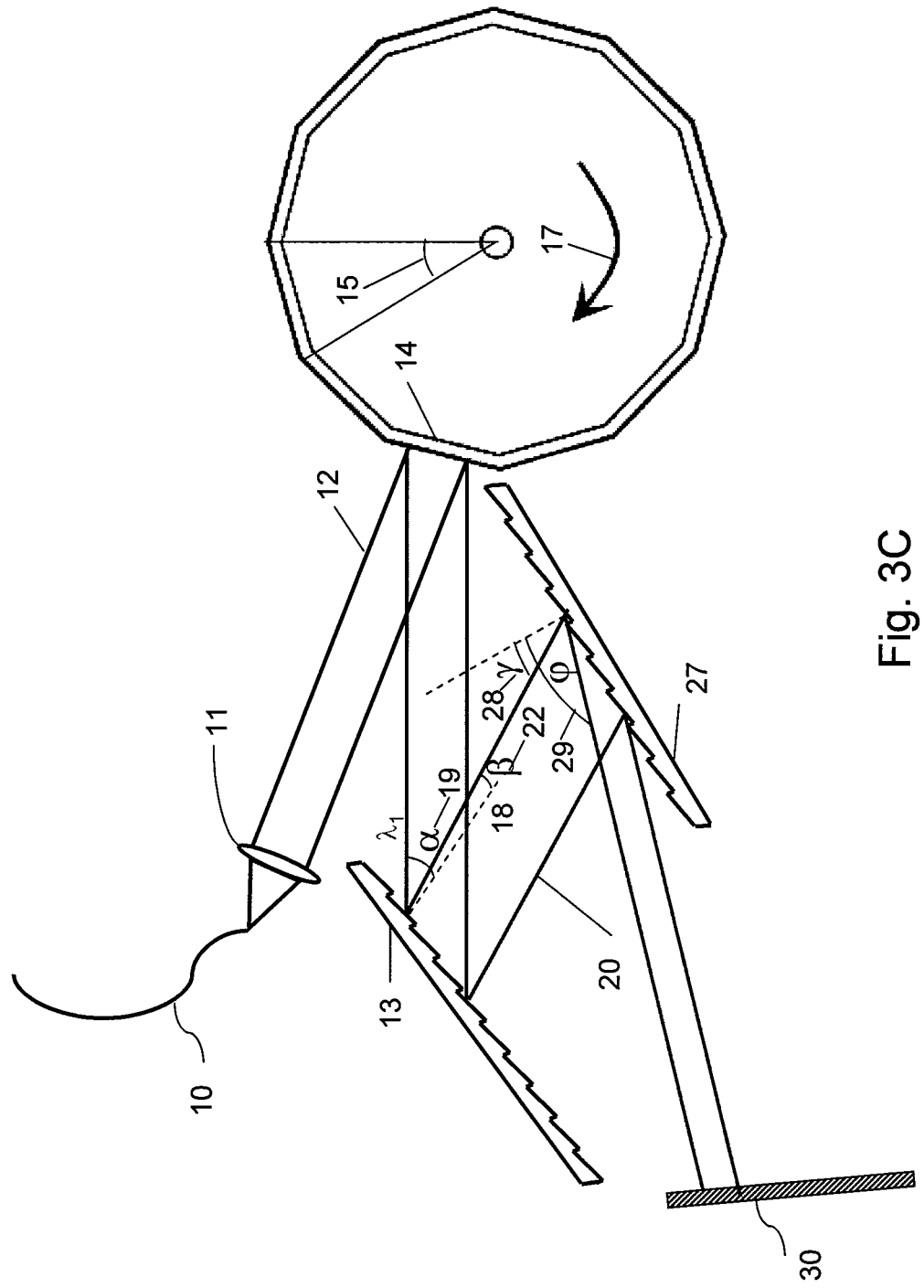
FIG. 3C is an illustration of an eight exemplary embodiment of the arrangement/apparatus which includes multiple diffraction gratings, the reflector and the polygon scanner according to the present invention.

FIG. 3C shows a diagram of an eight exemplary embodiment of the arrangement/apparatus which includes the wavelength tunable filter arrangement 1 with the same polygon rotation speed according to the present invention. In this exemplary embodiment, the reflected light from the polygon scanner facet 14 illuminates the diffraction grating 13 (with grating pitch $p_1$) at an angle $\alpha$19 (not equal to Littrow's angle). The diffracted light 20 at angle $\beta$22 from the grating illuminates other diffraction grating 27 (with grating pitch $p_2$) at an angle $\gamma$28 (not equal to Littrow's angle). The diffracted light at angle $\phi$29 illuminate a reflector 30 before retracing the path back to the light. It can be shown that the FWHM bandwidth of this filter (instantaneous line-widths) is given by $$\delta\lambda = \frac{2p_1 p_2 \lambda \sqrt{\ln(2)} \cos(\alpha)}{\pi D\left(p_2 + \frac{\cos(\beta)}{\cos(\gamma)} p_1\right)}.$$

The FWHM bandwidths of the filter configurations shown in FIGS. 3A-3C can be decreased further by increasing the number of diffraction grating.

Figure 4A:
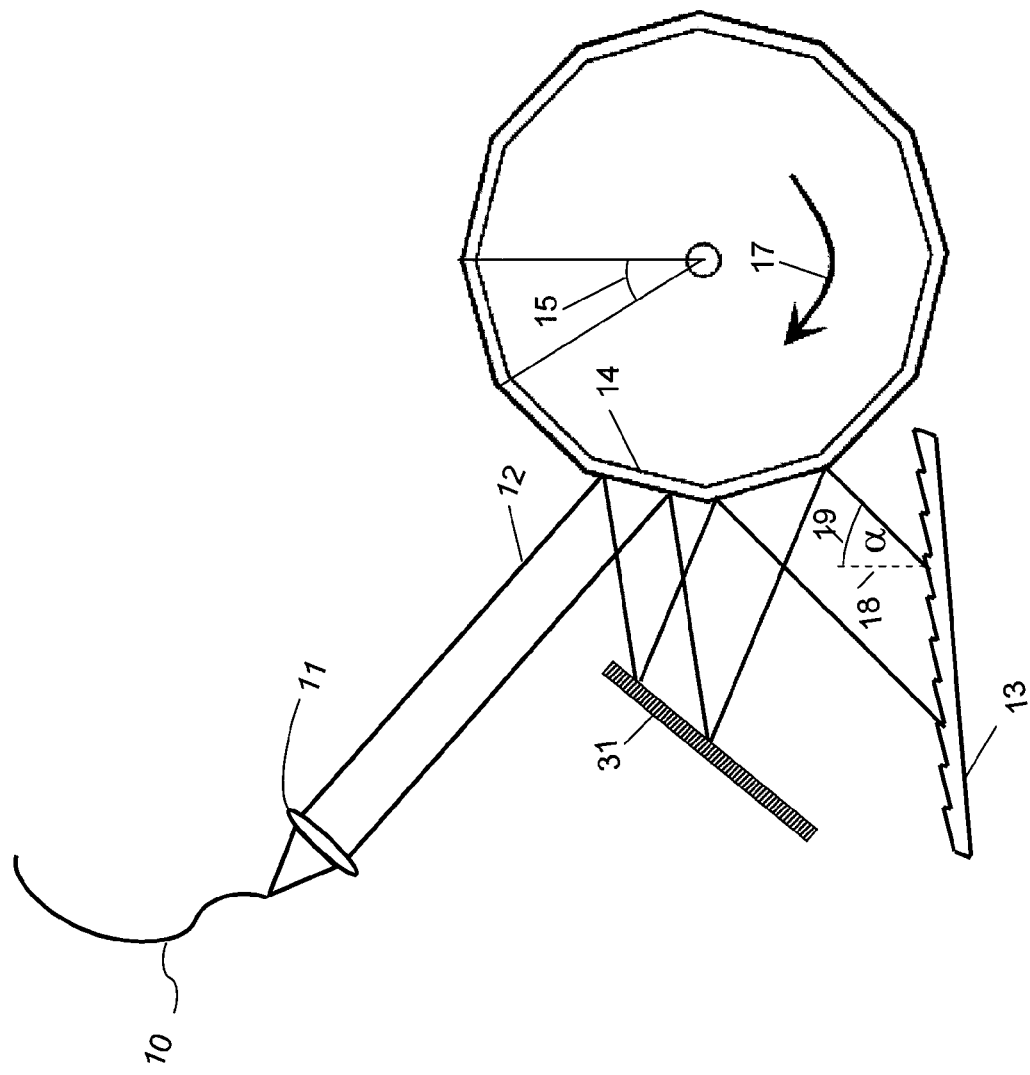
FIG. 4A is an illustration of a ninth exemplary embodiment of the arrangement/apparatus which includes the diffraction grating, the reflector, and the polygon scanner (or in combination with the other exemplary embodiments) according to the present invention.

FIG. 4A shows a diagram of a ninth exemplary embodiment of the arrangement/apparatus which includes the wavelength tunable filter arrangement for doubling the FSR of the filter with the same polygon rotation speed according to the present invention. In this exemplary embodiment, the reflected light from the polygon scanner facet 14 illuminates a reflector (or a folded telescope) and illuminates the other polygon facet and can be coupled to all previous described filter configurations. The sweep angle of the reflected light from the polygon arrangement is quadraple of the polygon rotation angle. When the facet-to-facet angle 15 of the polygon, e.g., angle $\theta$, the sweep angle of the reflected light is $4\theta$ for a rotation of the angle $\theta$ of the polygon arrangement. The reflector can be placed near the polygon scanner facet 14 to decrease beam displacement on the diffraction grating and avoid beam clipping on the second polygon facet.

Figure 4B:
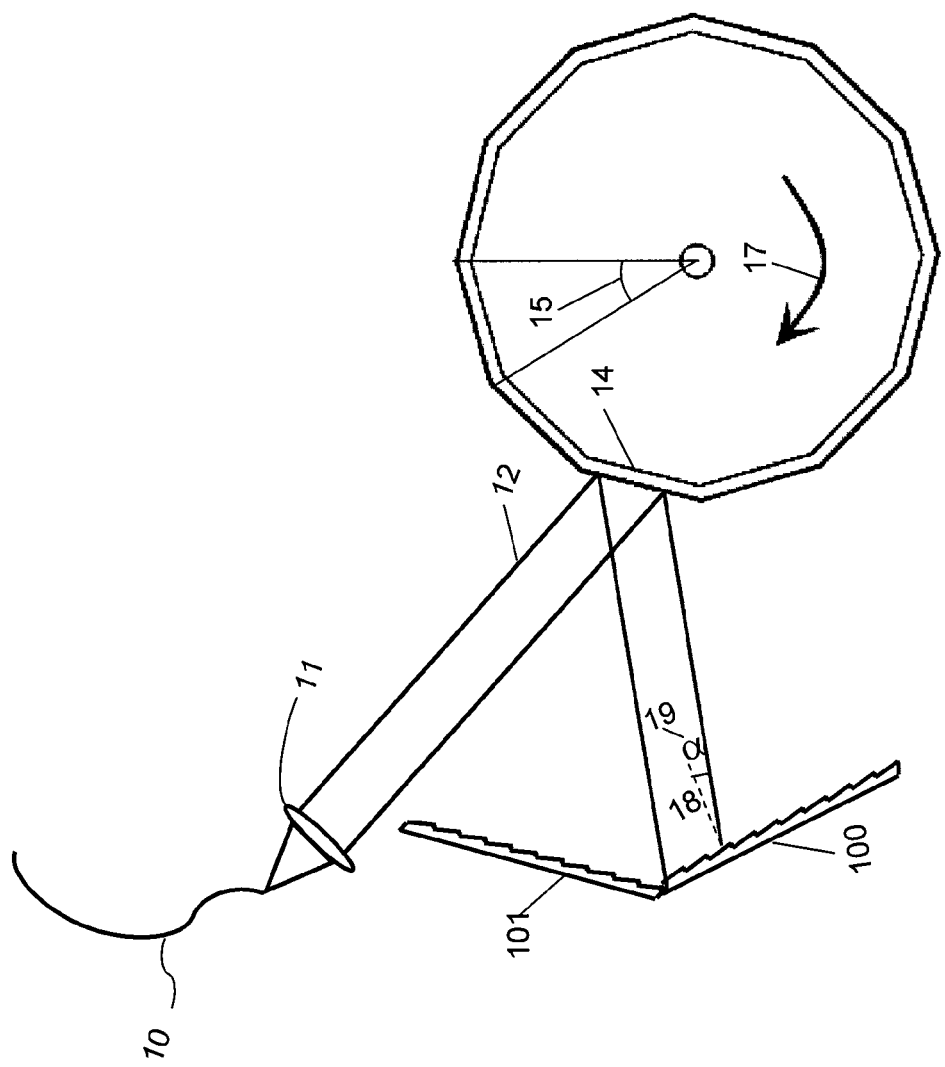
FIG. 4B is an illustration of a tenth exemplary embodiment of the arrangement/apparatus which includes two diffraction gratings and the polygon scanner (or in combination with the other exemplary embodiments) according to the present invention.

FIG. 4B shows a diagram of a tenth exemplary embodiment of the arrangement/apparatus which includes the wavelength tunable filter arrangement 1 for increasing the tuning speed of filter with the same polygon rotation speed and without increasing the number of polygon facets according to the present invention. By placing two (or N) diffraction gratings 100, 101 with the angle $2\theta/N$ between each other, which preferably direct the reflected beam of light from the polygon arrangement back to the polygon arrangement, and to the light controller 2, N wavelength scans from $\lambda_1$ to $\lambda_N$ are achieved for the polygon rotation of the one facet-to-facet angle, $\theta$. In this exemplary embodiment, the filter FSR decreases to $$(\Delta\lambda)_{FSR} = \frac{4p\theta\cos(\alpha_0)}{N}.$$

Figure 5A:
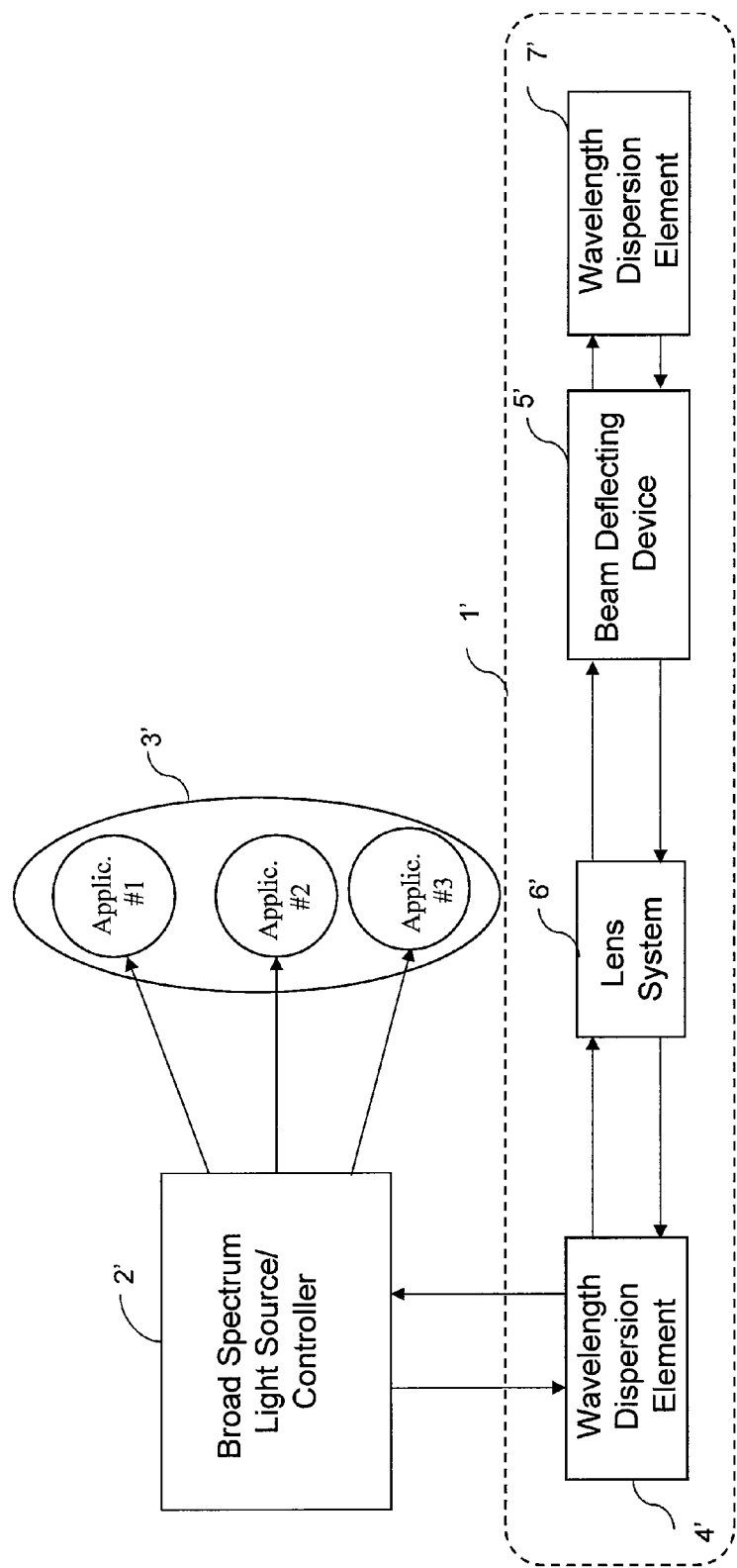
FIG. 5A is a block diagram of an eleventh exemplary embodiment of an optical wavelength filter according to the present invention.

FIG. 5A shows a block diagram of an eleventh exemplary embodiment of the arrangement/apparatus which includes the optical wavelength filter 1' in accordance the present invention. In this exemplary embodiment, the optical wavelength filter 1' can be used in a variety of different applications, general examples of which are described below. In this example, the filter 1' may be coupled to one or more applications 3' via a light source 2'. It should be understood that in certain exemplary applications, the filter 1' can be used with or connected to an application (e.g., one or more of the applications 3') via a device other than a light source (e.g. a passive or active optical element). In this exemplary embodiment as shown in FIG. 5A, a broad spectrum light source and/or controller 2' (hereinafter referred to as "light controller"), may be coupled to a wavelength dispersing element 4'. The light controller 2' can be further coupled to one or more of the applications 3' that are adapted to perform one or more tasks with or for, including but not limited to, optical imaging processes and optical imaging systems, laser machining processes and systems, photolithography and photolithographic systems, laser topography systems, telecommunications processes and systems, etc. The wavelength dispersing element 4' can be coupled to a lens system 6', which is further coupled to a beam deflection device 5' and wavelength dispersing element 7'.

The light controller 2' can be one or more of various systems and/or arrangements that are configured to transmit a beam of light having a broad frequency (f) spectrum. In one exemplary embodiment, the beam of light may be a collimated beam of light. The beam of light can include a plurality of wavelengths $\lambda \ldots \lambda n$, within the visible light spectrum (e.g., red, blue, green). Similarly, the beam of light provided by the light controller 2' can also include a plurality of wavelengths $\lambda \ldots \lambda n$ that may be defined outside of the visible spectrum (e.g., ultraviolet, near infrared or infrared). In one exemplary embodiment of the present invention, the light controller 2' can include a unidirectional light transmission ring, which shall be described in further detail below in connection with FIGS. 8A-D which shows an exemplary embodiment of a wavelength tuning laser source. Further, in another exemplary embodiment of the present invention, the light controller 2' can include a linear resonator system, which shall be described in further detail below in connection with FIGS. 8A-D.

The wavelength dispersing element 4' of the optical wavelength filter 1' can include one or more elements that are specifically adapted to receive the beam of light from the light controller 2', and to conventionally separate the beam of light into a plurality of wavelengths of light having a number of directions. The wavelength dispersing element 4' is further operative to direct portions of light having different wavelengths in equal angular directions or displacements with respect to an optical axis . . . . In one exemplary embodiment of the present invention, the wavelength dispersing element 4' can include a light dispersion element, which may include but not limited to, a reflection grating, a transmission grating, a prism, a diffraction grating, an acousto-optic diffraction cell or combinations of one or more of these elements.

The lens system 6' of the optical wavelength filter 1' can include one or more optical elements adapted to receive the separated wavelengths of light from the wavelength dispersing element. Light at each wavelength propagates along a path which is at an angle with respect to the optical axis 3 . . . . The angle is determined by the wavelength dispersing element 4'. Furthermore, the lens system 6' is adapted to direct or steer and/or focus the wavelengths of light to a predetermined position located on a beam deflection device 5'.

The beam deflection device 5' can be controlled to receive and selectively redirect one or more discrete wavelengths of light to the wavelength dispersing element 7'. The wavelength dispersing element 7 redirect back one or more discrete wavelengths to the beam deflection device 5' and then along the optical axis through the lens system 6' to the wavelength dispersing element 4' and back to the light controller 2'. Thereafter, the light controller 2' can selectively direct the received discrete wavelengths of light to any one or more of the applications. The beam deflecting device 5' can be provided in different ways. For example, the beam deflecting device 5' can be provided from elements including, but not limited to, a polygonal mirror, a planar mirror disposed on a rotating shaft, a mirror disposed on a galvonmeter, or an acousto-optic modulator.

Figure 5B:
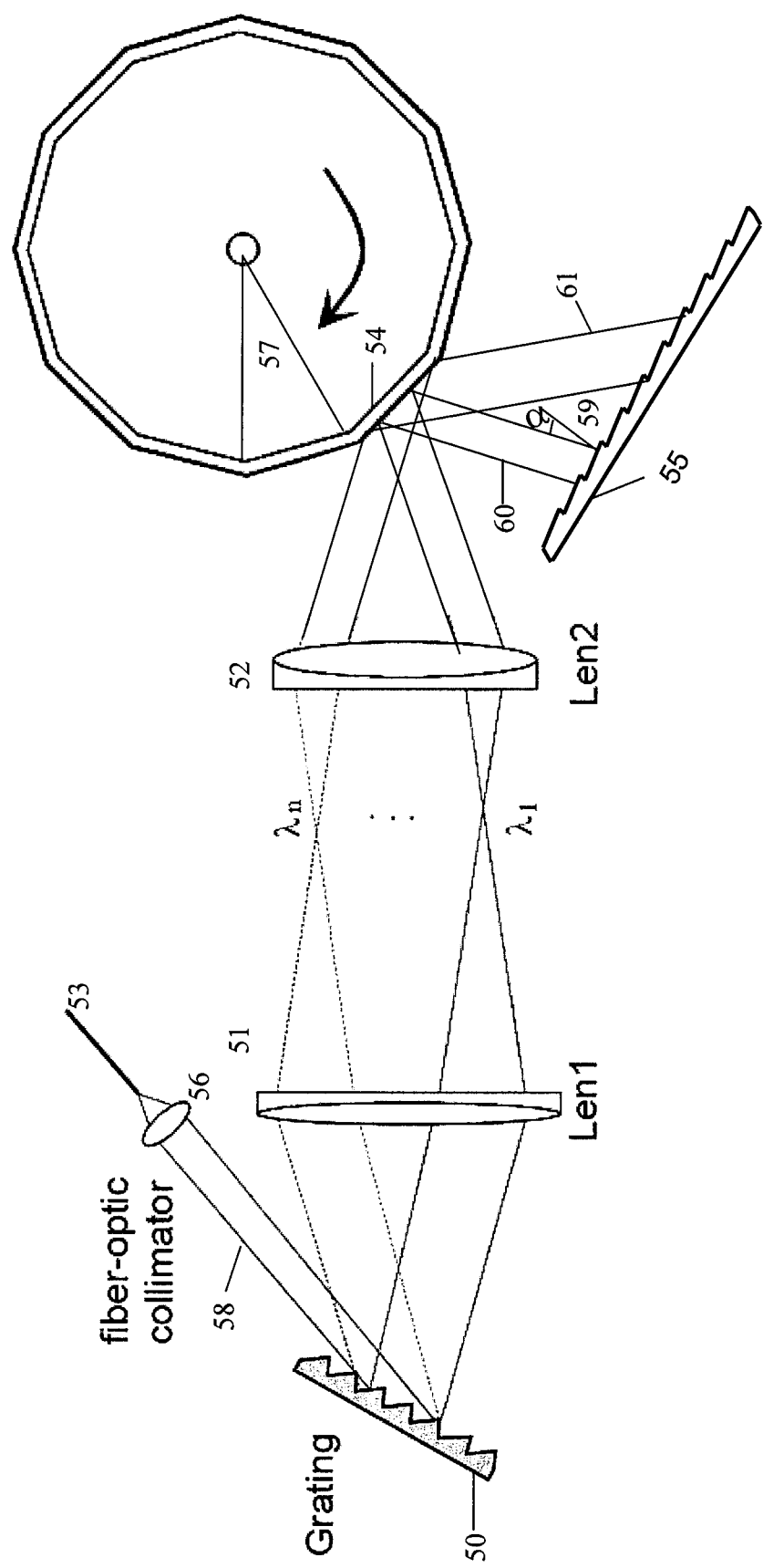
FIG. 5B is an illustration of a twelfth exemplary embodiment of the arrangement/apparatus which includes two diffraction gratings, a telescope, and the polygon scanner according to the present invention.

FIG. 5B shows a schematic diagram of a twelfth exemplary embodiment of the arrangement/apparatus which includes the optical wavelength filter 1'. The exemplary optical wavelength filter 1' can be configured as a reflection-type filter which may have substantially identical input and output ports. An input/output optical fiber 53 and a collimating lens 56 can provide an input from a light controller 2' (which may be substantially similar to the light controller 2 described above with reference to FIG. 5A) to the optical wavelength filter 1'. The optical wavelength filter 1' includes a diffraction grating 50, optical telescoping elements 5' (hereinafter referred to as "telescope 6'" and may possibly be similar to the lens system 6 of FIG. 1A), and a polygon mirror scanner 54. The telescope 6' can include two lenses, e.g., first and second lenses 51, 52 with 4-$f$ configuration.

In this embodiment of the optical wavelength filter 1' shown in FIG. 5B, the mirror surface of the polygon arrangement 54 is placed substantially a distance F2 from lens 22, and the beam of light is reflected with a non-zero angle (rather than directly being reflected back to the telescope from the polygon arrangement's 54 mirror facet). The sweep angle of the reflected light from the polygon arrangement 54 is double the polygon arrangement's 54 rotation angle. When the incident angle difference 90 between λ1 and λN with respect to the polygon arrangement 54 is approximately the same as the facet-to-facet angle 57 of the polygon, e.g., angle θ, the sweep angle 58 of the reflected light is 2θ for a rotation of the angle θ of the polygon arrangement 54. By illuminating a diffraction grating 55 at Littrow angle 59 which preferably direct the reflected beam of light from the polygon arrangement 54 back to the polygon arrangement 54, and to the telescope (e.g., similar to the telescope 6' of FIG. 5B), with the angle θ between each other, twice wavelength scans from λ1 to λN are achieved for the polygon rotation of the one facet-to-facet angle. In addition, the linewidth of this exemplary filter can be improved as compared to the previous polygon scanner filter using telescope and end reflector by illuminating other diffraction grating.

The first lens 51 may be located at a first distance from the wavelength dispensing element 4' (e.g., diffraction grating 50), which can approximately be equal to the focal length F1 of the first lens 51. The second lens 52 may be located at a second distance from the first lens 51, which can be approximately equal to the sum of the focal length F1 of the first lens 51 and the focal length F2 of the second lens 52. Using such exemplary arrangement, the first lens 51 can receive one or more collimated discrete wavelengths of light from the wavelength dispersing element 4', and can effectively perform a Fourier Transform on each one of the collimated one or more discrete wavelengths of light to provide one or more approximately equal converging beams that are projected onto an image plane IP.

The image plane IP can preferably be located between the first lens 51 and the second lens 52 and at a predetermined distance from the first lens 51. According to one exemplary variation of the present invention, such predetermined distance may be defined by the focal length F1 of the first lens 51. After such one or more converging beams are propagated through the image plane IP, these one or more converging beams form equal or corresponding one or more diverging beams that are received by the second lens 52. The second lens 52 is adapted to receive the diverging beams and provide approximately an equal number of collimated beams having predetermined angular displacements with respect to the optical axis. Thus, the second lens 52 can direct or steer the collimated beams to predefined portions of the beam deflection device 5'.

The telescope 6' according to this exemplary embodiment of the present invention can be operative to provide one or more features as described above, as well as to convert a diverging angular dispersion from the grating into converging angular dispersion after the second lens 52. Such result may be advantageous for a proper operation of the filter. In addition, the telescope 6' may provide adjustable parameters which control the tuning range and linewidth and reduce the beam size at the polygon mirror to avoid beam clipping. As is illustrated in the exemplary embodiment of FIG. 5B, a beam deflection device 5' (e.g., which may include a polygon mirror or arrangement 54) is adapted to preferably reflect only the spectral component within a narrow passband as a function of the angle of the front mirror facet of the polygon arrangement 54 with respect to the optic axis 38. The reflected narrow band light illuminates the diffraction grating 55 and diffracted and received by the optical fiber 53.

In this exemplary embodiment, the equations can be expressed as $\lambda = p_1(\sin(\alpha)+\sin(\beta))$ and $\lambda = 2p_2 \sin(\gamma)$, where λ is the optical wavelength, $p_1$ and $p_2$ are the grating pitches, and $\alpha$, $\beta$, $\gamma$ are the incident, diffracted, and Littrow angles of the beam with respect to the normal axes of the diffraction gratings 50, 55, respectively.

It can be shown that the FWHM bandwidth of the filter (instantaneous line-width) may be provided by $$\delta\lambda = \frac{2p_1p_2\lambda\sqrt{\ln(2)}\cos(\alpha)}{\pi D\left(p_2 + \frac{0.5\cos(\beta)}{\cos(\gamma)}p_1\right)} \quad (13)$$

Equation (13) shows that the linewidth of this embodiment has been improved by a factor of $$1 + \frac{0.5\cos(\beta)}{\cos(\gamma)}\frac{p_1}{p_2}$$

compared to the previous embodiment.

The tuning range of the filter may be limited by the finite numerical aperture of the first lens 51. The acceptance angle of the first lens 51 without beam clipping may be defined by $\Delta\beta = (D_1 - W\cos\beta_0/\cos\alpha)/F_1$ where D1 and F1 are the diameter and focal length of the first lens 51. Such formulation relates to the filter tuning range via the filter tuning range can be expressed as $$\Delta\lambda = \frac{F_2 p_1 \Delta\beta'}{F_1}\cos(\beta_0),$$

and $\Delta\lambda = 2p_2\Delta\gamma\cos(\gamma_0) = \Delta\gamma\sqrt{4p_2^2 - \lambda_0^2}$ where $\alpha_0$, $\beta_0$, and $\gamma_0$ are the incident, diffracted, and Littrow angles at $\lambda_0$ (center wavelength). One of exemplary design parameters of the filter, originated from the multiple facet nature of the polygon mirror, is the free spectral range, which is described in the following. A spectral component after propagating through the first lens 51 and the second lens 52 may have a beam propagation axis at an angle $\beta'$ with respect to the optic axis 38, e.g., $\beta' = -(\beta - \beta_0) \cdot (F_1/F_2)$, where $F_1$ and $F_2$ are the focal lengths of the first lens 51 and the second lens 52, respectively.

The polygon arrangement 54 may have a facet-to-facet polar angle given by $\theta = 2\pi/N \approx L/R$, where L is the facet width, R is the radius of the polygon and N is the number of facets. If the range of $\beta'$ of incident spectrum is greater than the facet angle, i.e. $\Delta\beta' = \Delta\beta \cdot (F_1/F_2) > \theta$, the polygon arrangement 24 can retro-reflect more than one spectral component at a given time. If the sweeping angle is equal to the range of the incident angle, i.e. $\Delta\beta' = 2\theta$ and the range of diffracted spectrum follows the following equality, i.e. $2\theta = \Delta\gamma$, the polygon arrangement can retro-reflect one spectral component at a given time. The spacing of the multiple spectral components simultaneously reflected, or the free spectral range, can be defined as $\Delta\lambda = 2\theta\sqrt{4p_2^2 - \lambda_0^2}$, when $$\frac{F_2}{F_1} = \frac{\sqrt{4p_2^2 - \lambda_0^2}}{p_1\cos(\beta_0)}.$$

The duty cycle of laser tuning by the filter can be, for example, 100% with no excess loss caused by beam clipping if two preferable conditions can be met as follows:

$$W < \frac{\cos\alpha F_1}{\cos\beta F_2}L \text{ and } W < \frac{\cos\alpha}{\cos\beta_0}(F_2 - S)\cdot\theta \quad (14)$$

The first equation may be derived from a condition that the beam width after the second lens 52 should be smaller than the facet width. The second equation can be derived from that the two beams at the lowest 60 and highest wavelengths 61 of the tuning range, respectively, which should not overlap each other at the polygon arrangement 54. S in equation (14) denotes the distance between the second lens 52 and the front mirror of the polygon arrangement 54.

Figure 5C:
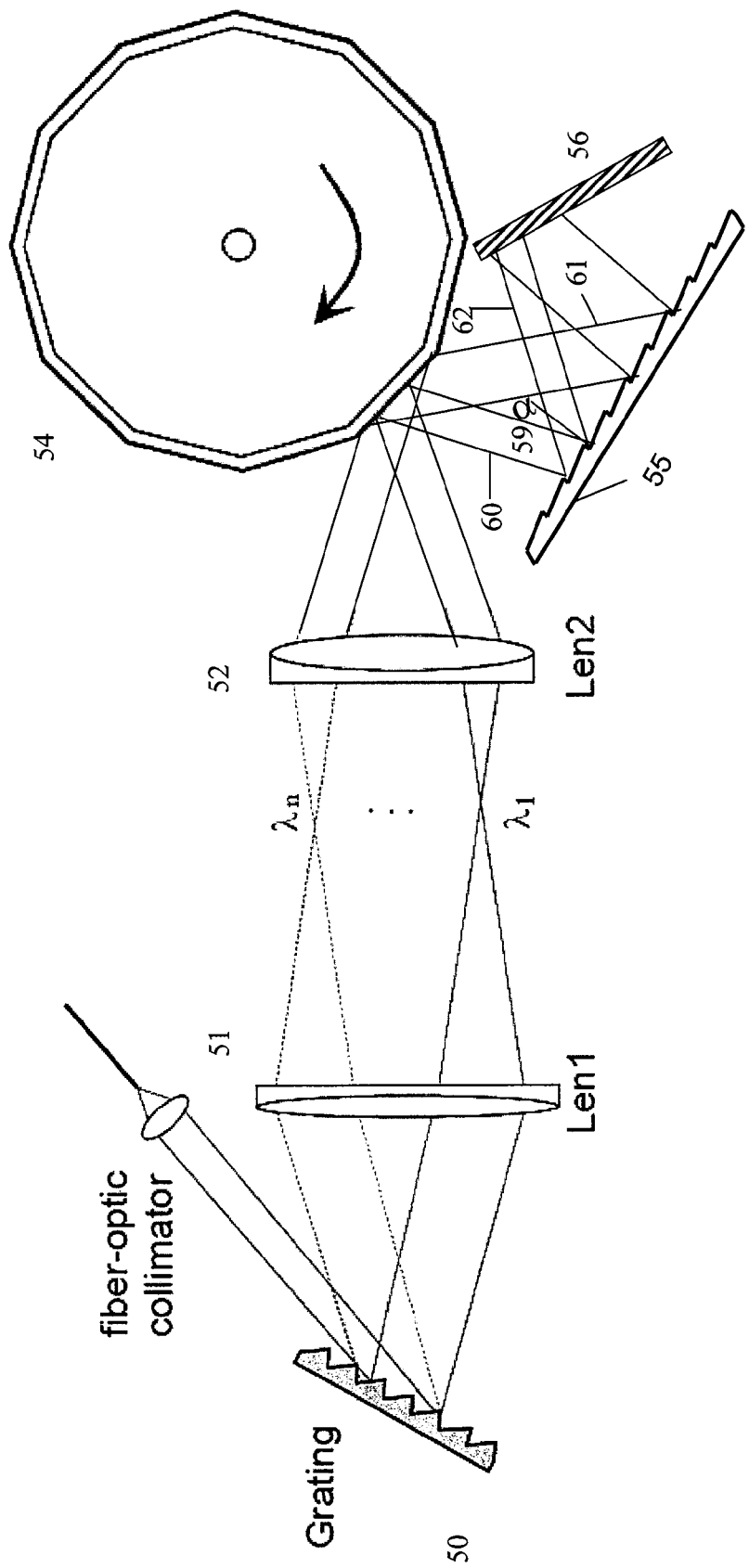
FIG. 5C is an illustration of a thirteenth exemplary embodiment of the arrangement/apparatus which includes two diffraction gratings, the telescope, the reflector and the polygon scanner according to the present invention.

FIG. 5C shows a schematic diagram of a thirteenth exemplary embodiment of the arrangement/apparatus which includes the optical wavelength filter 1'. In this exemplary embodiment, a diffraction grating 55 is illuminated at an angle 61 (not equal to Littrow angle). The diffracted light 62 at angle $\beta$ from the grating illuminates a reflector 56 before retracing the path back to the light controller 2. It can be shown that the FWHM bandwidth of this filter (instantaneous line-widths) is given by $$\delta\lambda = \frac{2p_1p_2\lambda\sqrt{\ln(2)}\cos(\alpha)}{\pi D\left(p_2 + \frac{\cos(\beta)}{\cos(\gamma)}p_1\right)}.$$

Figure 5D:
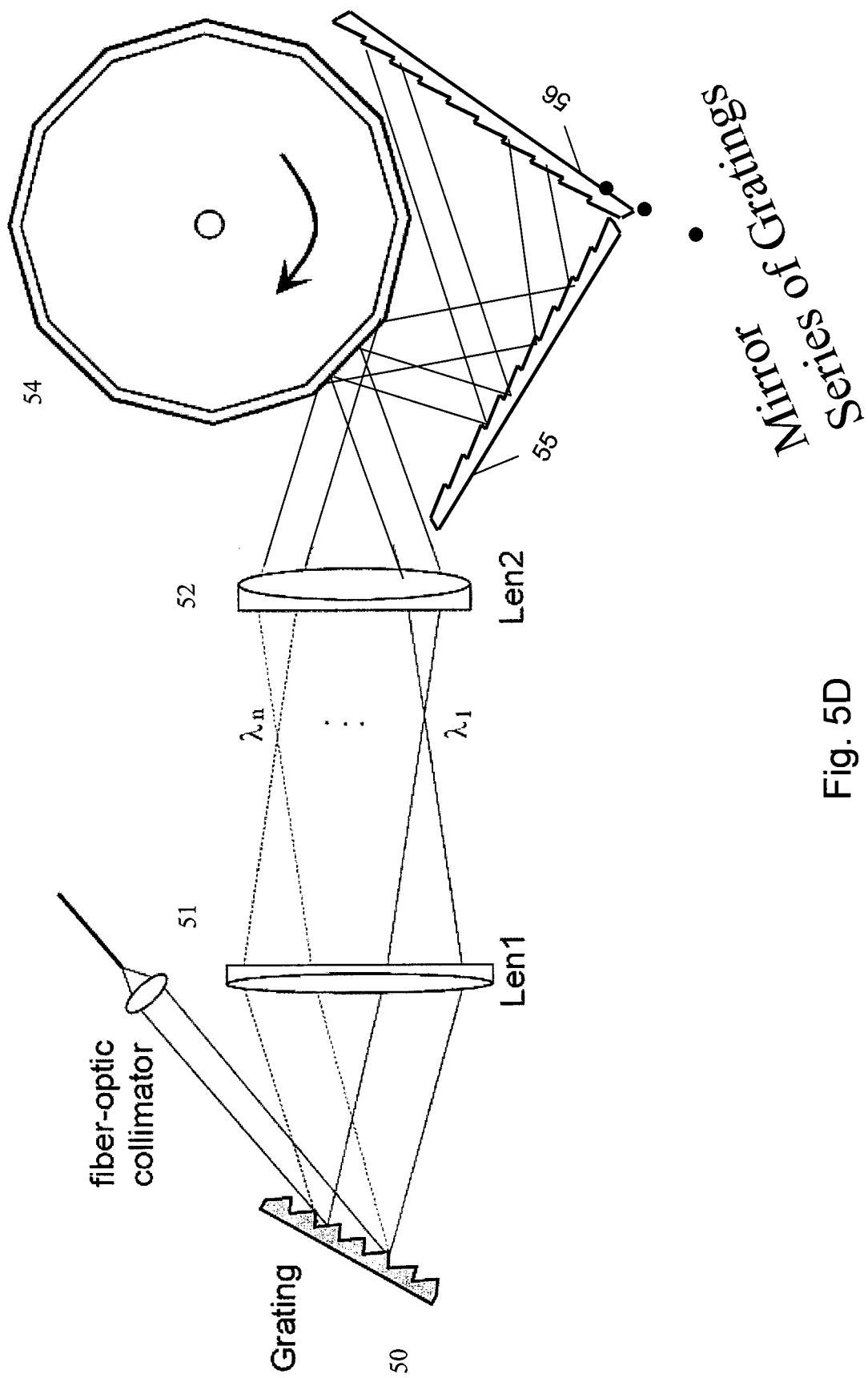
FIG. 5D is an illustration of a fourteenth exemplary embodiment of the arrangement/apparatus which includes three diffraction gratings, the telescope and the polygon scanner according to the present invention.

FIG. 5D shows a schematic diagram of a fourteenth exemplary embodiment of the arrangement/apparatus which includes the optical wavelength filter 1'. In this exemplary embodiment, reflector 56 is replaced in the previous embodiment with several gratings to narrow the instantaneous line-width of the filter.

Figure 6A:
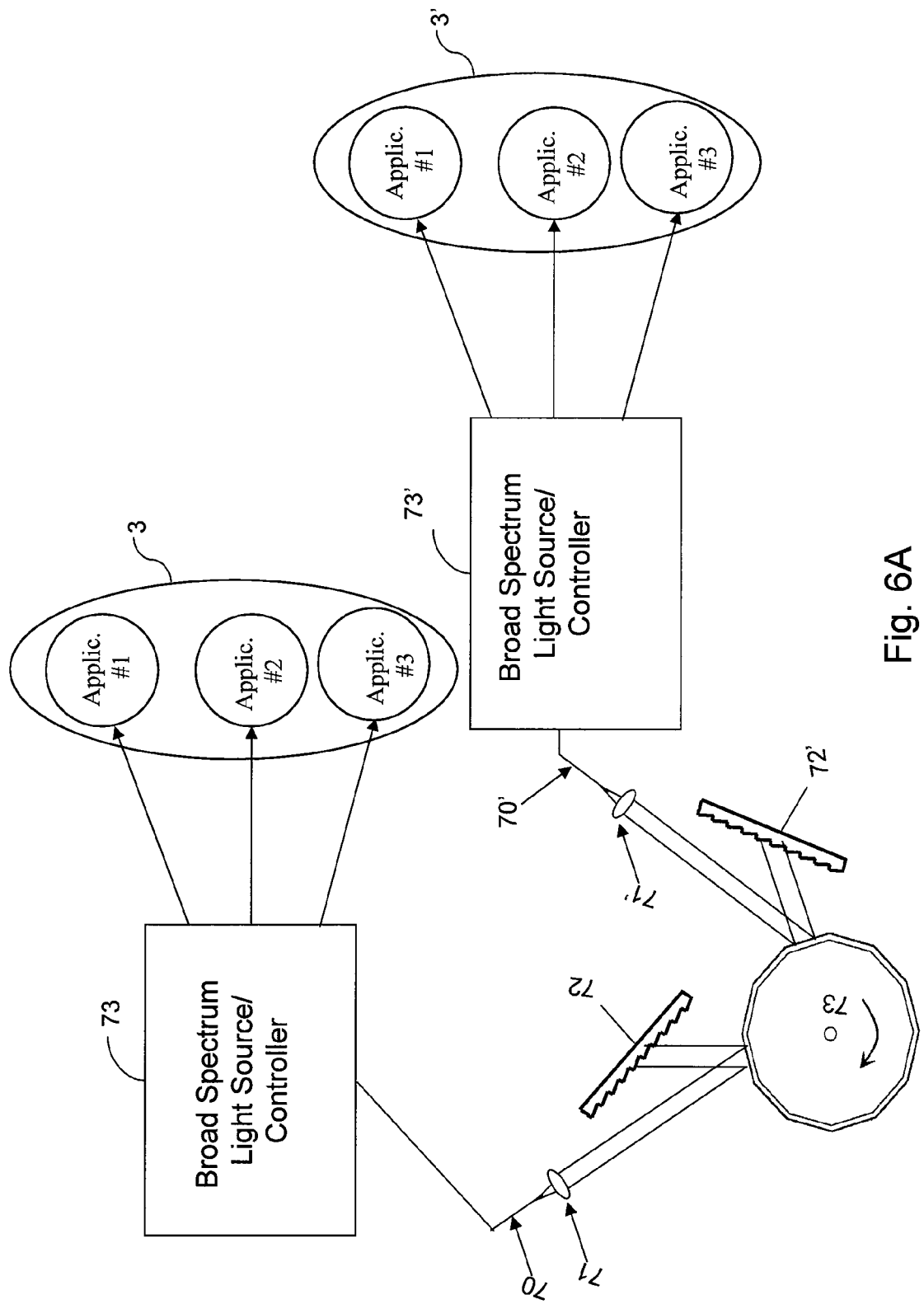
FIG. 6A is an illustration of a fifteenth exemplary embodiment of the arrangement/apparatus which includes the diffraction grating and the polygon scanner based wavelength tuning filter using two (or N) gain mediums according to the present invention.

FIG. 6A shows a fifteenth exemplary embodiment of the arrangement/apparatus of the present invention which provides a polygon tuning filter accommodating two light inputs and outputs. For example, in order to support two or more inputs and outputs of this filter, two or more sets of optical arrangements, each respective set including an input/output fiber 70, 70', a collimating lens 71, 71', a diffraction gratings (or previous described filter configurations) 72, 72', may share the same polygon arrangement 73. Because the scanning mirror of the polygon arrangement 73 is structurally isotropic about the rotation axis, certain optical arrangements that can deliver the beams of light to the polygon arrangement 73 can be accommodated from any directions. Since both sets of optical arrangement in the embodiment of FIG. 6A, utilize the same polygon scanner, their respective scanning optical transmission spectra are synchronized. It should be understood that the embodiment of FIG. 6A can be extended to include multiple (e.g., greater than 2) optical arrangements each having its own input and output optical channel.

One exemplary application of the above-described exemplary polygon tuning filter according to the tenth embodiment of the present invention may be a wide band wavelength scanning light source. In FIG. 6A which shows a fifteenth exemplary embodiment of the present invention, a first broadband light source 74 provides a light signal which may have a wavelength $\lambda 1$ to $\lambda i$, and a second broadband light source 74' provides another light signal having a wavelength $\lambda i\text{-}j$ to $\lambda N$. When the two optical arrangements supporting the wavelengths $\lambda 1$ to $\lambda i$ and the wavelengths $\lambda i\text{-}j$ to $\lambda N$, respectively, are synchronized to output approximately the same wavelength at the same instance, such exemplary arrangement may become a wide band wavelength scanning light source with linear scan rate from λ1 to λN. Since the FSR of the polygon scanning filter can be adjusted to be 350 nm or wider without any optical performance degradation, two or more broadband light sources with different center wavelengths can be combined with this filter to provide linear scanning light source over 350 nm tuning bandwidth. It should be understood that the embodiment of FIG. 6A can be extended to include multiple (e.g., >2) optical arrangements and multiple (e.g., >2) broadband light sources.

The exemplary embodiment of the arrangement/apparatus shown in FIG. 6A can also be configured so that the wavelength tuning bands of each optical arrangement and broadband light source are discontinuous. In such a configuration, the tuning bands can be swept in a continuous or discontinuous sequential manner or be swept simultaneously.

Figure 6B:
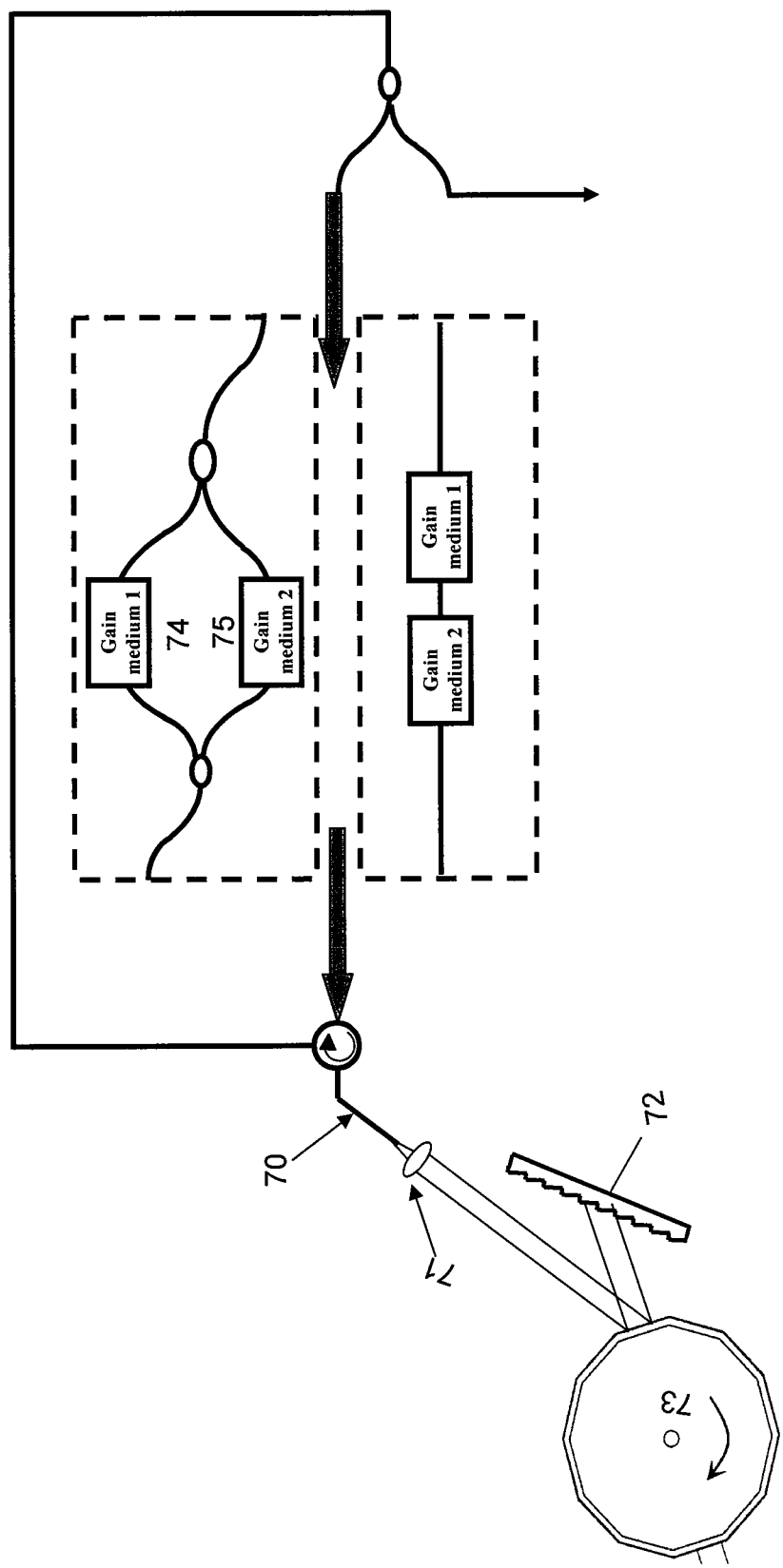
FIG. 6B is an illustration of a sixteenth exemplary embodiment of the arrangement/apparatus which includes the diffraction grating and the polygon scanner based wavelength tuning filter using two (or N) gain mediums in series or parallel according to the present invention.

FIG. 6B shows a sixteenth exemplary embodiment of the present invention of the arrangement/apparatus for increasing the filter FSR by combination of two or more gain media 74 and 75 (parallel or serial) whose gain spectra are distinct. This exemplary arrangement/approach has advantage compared to the twelfth exemplary embodiment because there is less preference for multiple (e.g., ≥2) optical arrangements and synchronizing the wavelength sweep of the independent resonators.

Figure 7:
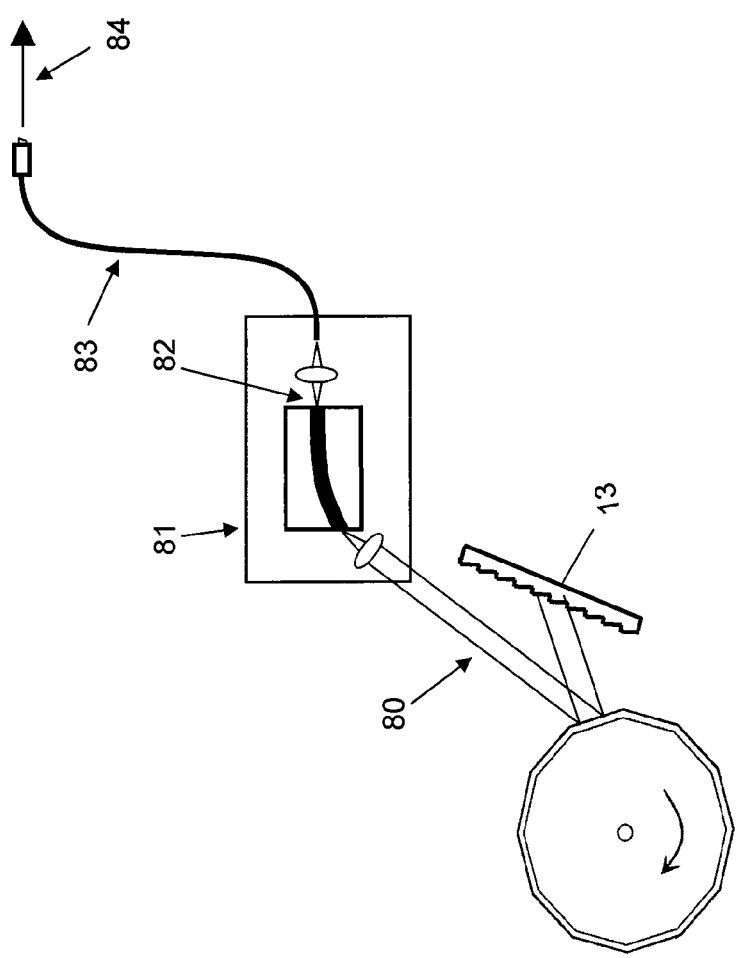
FIG. 7 is an illustration of a seventeenth exemplary embodiment of the arrangement/apparatus which includes a short linear cavity laser using the diffraction grating and the polygon scanner based wavelength tuning filter according to the present invention.

FIG. 7 shows an exemplary embodiment of the arrangement/apparatus which includes the wavelength-swept laser using the grating and polygon scanner filter. Collimated light output 80 from a semiconductor optical amplifier (SOA) 81 is directly coupled into the grating and polygon scanner filter. A small portion of the light from the reflection facet side of the SOA 82 can be coupled into the single mode fiber 83 providing output of the laser 84.

A frequency downshift in the optical spectrum of the intracavity laser light may arise as the light passes through the SOA gain medium, as a result of an intraband four-wave mixing phenomenon. In the presence of the frequency downshift, greater output power can be generated by operating the wavelength scanning filter in the positive wavelength sweep direction. Since the combined action of self-frequency shift and positive tuning allows higher output to be obtained and enables the laser to be operated at higher tuning speed, the positive wavelength scan may be the preferable operation. The output power can be decreased and the instantaneous linewidth can be broadened with an increasing tuning speed. A short cavity length may be desired to reduce the sensitivity of the output power and instantaneous linewidth to the tuning speed.

With a short length wavelength scanning filter based on the grating and polygon scanner filter and direct free-space coupling between the gain medium and the optical wavelength filter, the total cavity round trip length can be shorter than 20 cm, which is advantageous for reducing the sensitivity of the output power and instantaneous linewidth to the tuning speed.

Figure 8A:
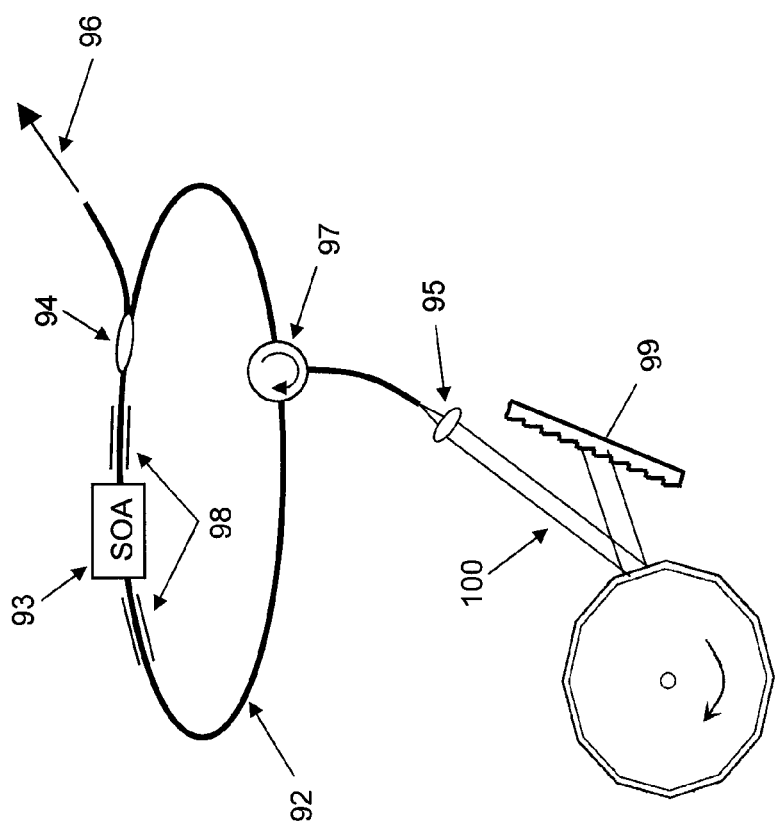
FIG. 8A is an illustration of an eighteenth exemplary embodiment of the arrangement/apparatus which includes a fiber ring laser using the diffraction grating and the polygon scanner based wavelength tuning filter according to the present invention.

FIG. 8A shows another embodiment of the arrangement/apparatus which includes the wavelength-swept laser using the grating and polygon scanner filter. Fiber ring cavity 92 can be coupled to the grating and polygon scanner filter via collimating lens 95. For the applications where the high speed tuning is not essential so that the relatively long cavity length can be allowed, fiber ring cavity with a conventional dual port SOA 93 can be an optional configuration.

Figure 8B:
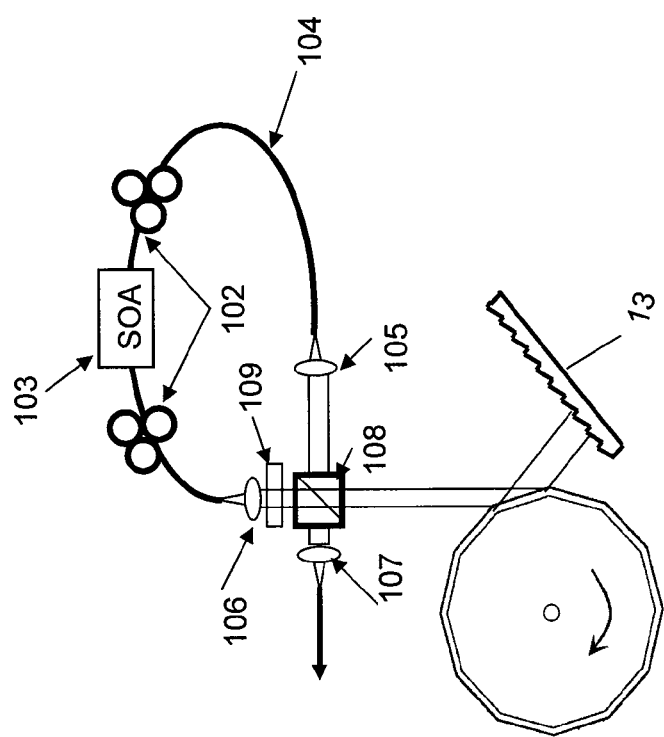
FIG. 8B is an illustration of a nineteenth exemplary embodiment of the arrangement/apparatus which includes a combined fiber and free space ring laser using the diffraction grating and polygon scanner based wavelength tuning filter according to the present invention.

FIG. 8B shows another embodiment of the arrangement/apparatus which includes the wavelength-swept laser using the grating and polygon scanner filter. Fiber and free space ring cavity can be coupled to the grating and polygon scanner filter via collimating lens 106, beam cube splitter 108, and optical isolator 109. For the applications where the high speed tuning is essential so that the short cavity length can be important, combination of fiber and free space ring cavity with a conventional dual port SOA 103 can be an optional configuration.

Figure 8C:
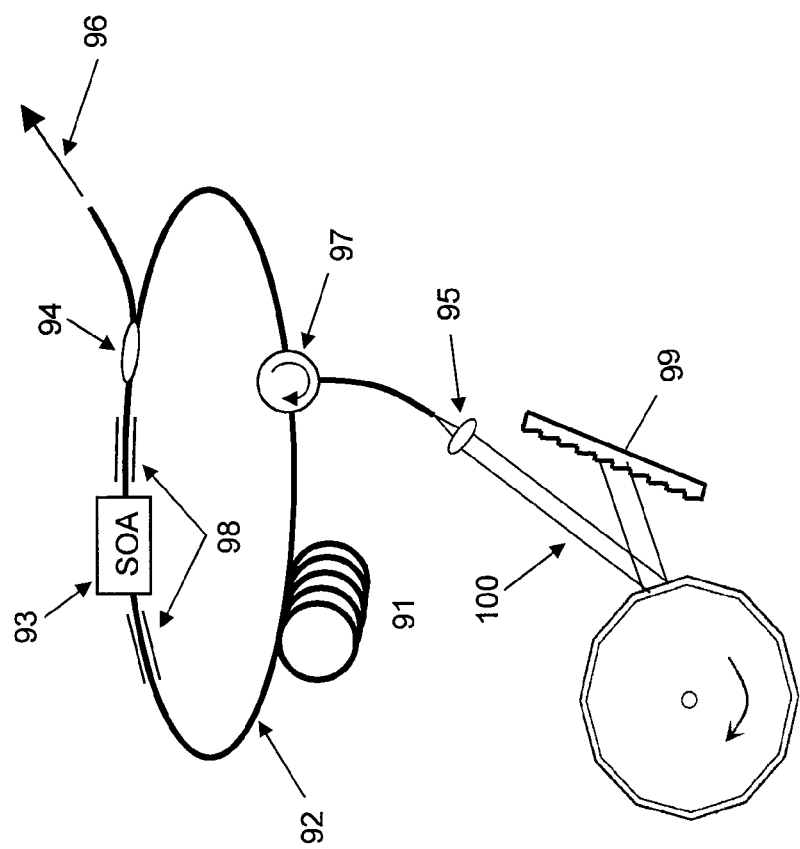
FIG. 8C is an illustration of a twentieth exemplary embodiment of the arrangement/apparatus which includes a resonant cavity fiber ring laser using the diffraction grating and the polygon scanner based wavelength tuning filter according to the present invention.

FIG. 8C shows an exemplary embodiment of the arrangement/apparatus which includes a fiber ring wavelength swept-laser with long cavity length. Increasing the cavity length so that the laser light can become resonant after a round trip of the cavity is another way to reduce the sensitivity of the output power and instantaneous linewidth to the tuning speed. Additional length of fiber 91, whose length depends on the tuning repetition rate, in the ring cavity 92 enables resonant tuning. Cavity length variation of the laser cavity with the grating and polygon scanner filter may be smaller than that of the polygon scanner based laser, therefore better resonant may be obtainable.

Figure 8D:
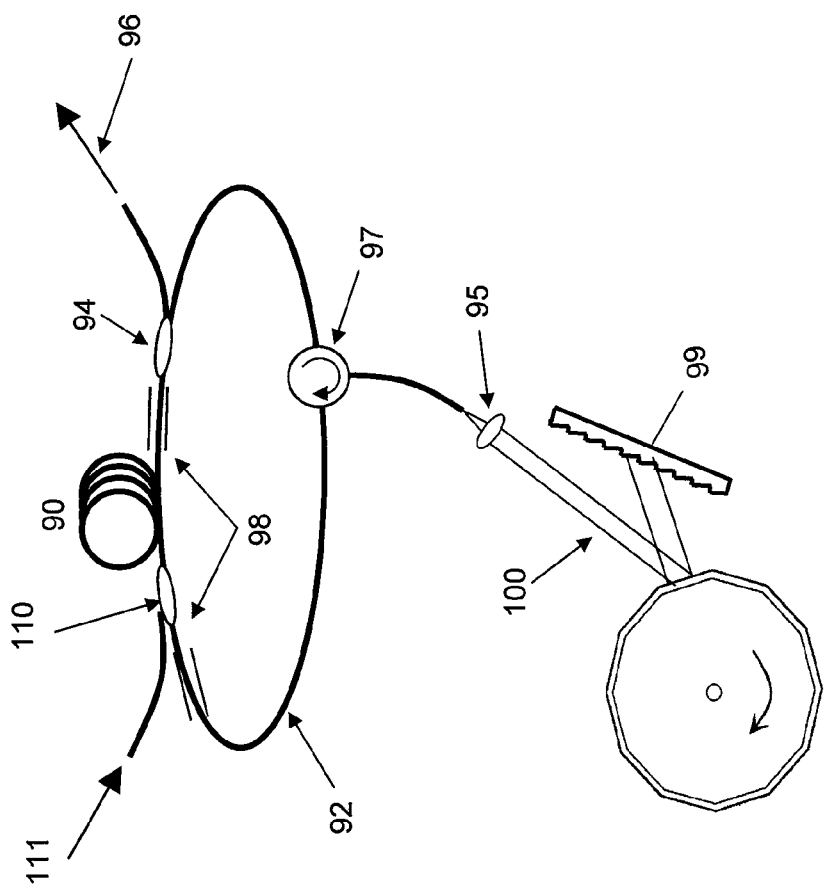
FIG. 8D is an illustration of a twenty-first exemplary embodiment of the arrangement/apparatus which includes the resonant cavity fiber Raman ring laser using the diffraction grating and the polygon scanner based wavelength tuning filter according to the present invention.

FIG. 8D shows an exemplary embodiment of the resonant cavity fiber Raman ring laser using the grating and polygon scanner filter. Since long length of optical fiber 90 is needed for resonant wavelength tuning, Raman gain can be induced in the long length of fiber 90 with proper pump light 111 supplied through a WDM coupler 110. Special type of fiber can be used as a long length fiber 90 in the cavity to enhance the Raman gain efficiency. Since the Raman gain wavelength band is determined by the wavelength band of the pump light, wavelength swept-laser with arbitrary wavelength tuning band may be obtained as far as the pump light with proper wavelength band is available.

Further, depending on the pump light power and the Raman gain efficiency in the fiber, high power wavelength-swept laser may be implemented. Pump light for the Raman gain can be also provided in backward direction to the laser light and both forward and backward pumps can be used simultaneously to obtain higher gain. The pump light is not limited to the light with a single wavelength component. To obtain a broad bandwidth Raman gain, a multiple wavelength pump light can be preferably utilized. This scheme can be further expanded to achieve a laser tuning range beyond the filter free spectral range by using multiple Raman pump light staggered in wavelength, whose gain bandwidth is broader than the free spectral range of the filter, that are progressively cycled on and off.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus for filtering an electromagnetic radiation, comprising:
   at least one first arrangement configured to receive at least one first electro-magnetic radiation and forward at least one second electro-magnetic radiation at different angles with respect to a direction of incidence of the at least one first electro-magnetic radiation; and
   at least one wavelength dispersion second arrangement configured to receive the at least one second electro-magnetic radiation, intentionally forward at least one third electro-magnetic radiation to the at least one first arrangement and further receive at least one fourth electro-magnetic radiation, wherein the at least one third electro-magnetic radiation is a return radiation from the at least one wavelength dispersion second arrangement based on the at least one second electro-magnetic radiation, and wherein the at least one fourth electro-magnetic radiation is a direct reflection of the at least one third electro-magnetic radiation from the at least one first arrangement.

2. The apparatus according to claim 1, wherein the at least one first arrangement is a multi-faceted mirror arrangement.

3. The apparatus according to claim 2, wherein the at least one first electro-magnetic radiation is intentionally caused to impact a first facet of the multi-faceted mirror arrangement, and the at least one third electro-magnetic radiation impacts a second facet of the multi-faceted mirror arrangement, the first and second facets being different from one another.

4. The apparatus according to claim 1, wherein the at least one first arrangement is a polygon beam scanning arrangement.

5. The apparatus according to claim 4, wherein the at least one first electro-magnetic radiation impacts a first facet of the polygon beam scanning arrangement, and the at least one third electro-magnetic radiation impacts a second facet of the polygon beam scanning arrangement, the first and second facets being different from one another.

6. The apparatus according to claim 5, wherein the polygon beam scanning arrangement is capable of being continuously rotated.

7. The apparatus according to claim 1, wherein the at least one second arrangement is at least one of a prism arrangement or a grism arrangement.

8. The apparatus according to claim 1, wherein the first and second arrangements are positioned such that a further electro-magnetic radiation that is based on the first electro-magnetic radiation is received by the at least one first arrangement from the at least one second arrangement more that twice.

9. The apparatus according to claim 1, further comprising:
   at least one wavelength dispersion third arrangement configured to physically separate one or more components of a further electro-magnetic radiation based on a frequency of the further electro-magnetic radiation, wherein the at least one first electro-magnetic radiation is based on the further electro-magnetic radiation.

10. The apparatus according to claim 9, further comprising:
    at least one fourth arrangement which is configured to receive at least some of the one or more components, and modify at least one characteristic of the received one or more components to provide the at least one first electro-magnetic radiation which is associated with one or more further components of the further electro-magnetic radiation.

11. A source arrangement for providing at least one particular electromagnetic radiation, comprising:
    at least one emitter arrangement configured to provide the at least one particular electromagnetic radiation;
    at least one first arrangement configured to receive the at least one particular electro-magnetic radiation and forward at least one first electro-magnetic radiation at different angles with respect to a direction of incidence of the at least one particular electro-magnetic radiation; and
    at least one wavelength dispersion second arrangement configured to receive the at least one first electro-magnetic radiation, forward at least one second electro-magnetic radiation to the at least one first arrangement and further receive at least one third electro-magnetic radiation, wherein the at least one second electro-magnetic radiation is a return radiation from the at least one wavelength dispersion second arrangement based on the at least one first electro-magnetic radiation, and wherein the at least one third electro-magnetic radiation is a direct reflection of the at least one second electro-magnetic radiation from the at least one first arrangement.

12. The source arrangement according to claim 11, further comprising at least one laser cavity receiving the at least one third electromagnetic radiation.

13. The source arrangement according to claim 12, wherein the laser cavity is a ring laser cavity.

14. The source arrangement according to claim 11, wherein the at least one emitter arrangement is at least one of a semiconductor optical amplifier, a laser diode, a superluminescent diode, a doped optical fiber, a doped laser crystal, a doped laser glass, or a laser dye.

15. The source arrangement according to claim 11, wherein the at least one particular electromagnetic radiation has a frequency that is continuously swept in a positive wavelength direction.

16. The source arrangement according to claim 11, further comprising an optical circulator.

17. The source arrangement according to claim 11, wherein wavelength ranges of the at least one particular electromagnetic radiation provided by the at least one emitter arrangement are distinct from one another.

18. The source arrangement according to claim 11, wherein the at least one first arrangement is a multi-faceted mirror arrangement.

19. The source arrangement according to claim 16, wherein the at least one particular electro-magnetic radiation impacts a first facet of the multi-faceted mirror arrangement, and the at least one second electro-magnetic radiation impacts a second facet of the multi-faceted mirror arrangement, the first and second facets being different from one another.

20. The source arrangement according to claim 11, wherein the at least one first arrangement is a polygon beam scanning arrangement.

21. The source arrangement according to claim 20, wherein the at least one particular electro-magnetic radiation impacts a first facet of the polygon beam scanning arrangement, and the at least one second electro-magnetic radiation impacts a second facet of the polygon beam scanning arrangement, the first and second facets being different from one another.

22. The source arrangement according to claim 19, wherein the polygon beam scanning arrangement is capable of being continuously rotated.

23. The source arrangement according to claim 11, wherein the at least one second arrangement is at least one of a prism arrangement or a grism arrangement.

24. The source arrangement according to claim 11, wherein the first and second arrangements are positioned such that a further electro-magnetic radiation that is based on the first electro-magnetic radiation is received by the at least one first arrangement from the at least one second arrangement more that twice.

25. The source arrangement according to claim 11, further comprising:
at least one wavelength dispersion third arrangement configured to physically separate one or more components of a further electro-magnetic radiation based on a frequency of the particular electro-magnetic radiation, wherein the at least one particular electro-magnetic radiation is based on the further electro-magnetic radiation.

26. The source arrangement according to claim 25, further comprising:
at least one fourth arrangement which is configured to receive at least some of the one or more components, and modify at least one characteristic of the received one or more components to provide at least one particular electro-magnetic radiation which is associated with one or more further components of the further electro-magnetic radiation.

27. A method for filtering an electromagnetic radiation, comprising:
receiving at least one first electro-magnetic radiation and forwarding at least one second electro-magnetic radiation at different angles with respect to a direction of incidence of the at least one first electro-magnetic radiation; and
receiving the at least one second electro-magnetic radiation, intentionally forwarding at least one third electro-magnetic radiation to the at least one first arrangement and further receiving at least one fourth electro-magnetic radiation,
wherein the at least one third electro-magnetic radiation is a return radiation from the at least one wavelength dispersion second arrangement based on the at least one second electro-magnetic radiation, and wherein the at least one fourth electro-magnetic radiation is a direct reflection of the at least one third electro-magnetic radiation from the at least one first arrangement.

28. A method for providing at least one particular electro-magnetic radiation, comprising:
providing the at least one electromagnetic radiation using at least one emitter arrangement;
receiving the at least one particular electro-magnetic radiation and intentionally forwarding at least one first electro-magnetic radiation at different angles with respect to a direction of incidence of the at least one particular electro-magnetic radiation; and
receiving the at least one first electro-magnetic radiation, forwarding at least one second electro-magnetic radiation to the at least one first arrangement and further receiving at least one third electro-magnetic radiation using at least one second wavelength dispersion arrangement,
wherein the at least one second electro-magnetic radiation is a return radiation from the at least one wavelength dispersion second arrangement based on the at least one first electro-magnetic radiation, and wherein the at least one third electro-magnetic radiation is a direct reflection of the at least one second electro-magnetic radiation from the at least one first arrangement.

* * * * *

UNITED STATES PATENT AND TRADEMARK OFFICE
CERTIFICATE OF CORRECTION

PATENT NO. : 9,176,319 B2
APPLICATION NO. : 12/052984
DATED : November 3, 2015
INVENTOR(S) : Brett Eugene Bouma et al.

Page 1 of 1

It is certified that error appears in the above-identified patent and that said Letters Patent is hereby corrected as shown below:

Column 1, line 13, after the "CROSS-REFERENCE TO RELATED APPLICATION(S)", please add the following paragraph as follows:

STATEMENT REGARDING FEDERALLY SPONSORED RESEARCH
This invention was made with Government support under Grant Number HL076398 awarded by the National Institutes of Health. The Government has certain rights in this invention.

Signed and Sealed this
Sixteenth Day of February, 2016

Michelle K. Lee
*Director of the United States Patent and Trademark Office*